(12) United States Patent
Butler et al.

(10) Patent No.: US 8,536,164 B2
(45) Date of Patent: Sep. 17, 2013

(54) FUSED PYRIDINE COMPOUNDS AS CASEIN KINASE INHIBITORS

(75) Inventors: Todd W. Butler, Salem, CT (US); Ramalakshmi Y. Chandrasekaran, Gales Ferry, CT (US); Scot R. Mente, Mystic, CT (US); Chakrapani Subramanyam, South Glastonbury, CT (US); Travis T. Wager, New London, CT (US)

(73) Assignee: Pfizer Inc., New York, NY (US)

( * ) Notice: Subject to any disclaimer, the term of this patent is extended or adjusted under 35 U.S.C. 154(b) by 106 days.

(21) Appl. No.: 13/323,883

(22) Filed: Dec. 13, 2011

(65) Prior Publication Data

US 2012/0157440 A1 Jun. 21, 2012

Related U.S. Application Data

(60) Provisional application No. 61/425,213, filed on Dec. 20, 2010.

(51) Int. Cl.

| | |
|---|---|
| *A61K 31/4355* | (2006.01) |
| *A61K 31/437* | (2006.01) |
| *A61K 31/506* | (2006.01) |
| *A61K 31/435* | (2006.01) |
| *C07D 471/04* | (2006.01) |
| *C07D 498/04* | (2006.01) |
| *C07D 401/04* | (2006.01) |
| *A61P 25/24* | (2006.01) |

(52) U.S. Cl.
USPC ........ 514/211.1; 514/302; 514/300; 514/256; 546/113; 546/115; 546/183; 540/552

(58) Field of Classification Search
USPC ...... 514/211.1, 302, 300, 256, 299; 546/115, 546/113, 183; 540/552
See application file for complete search history.

(56) References Cited

U.S. PATENT DOCUMENTS 6,908,930 B2 * 6/2005 Liang et al. .................. 514/300

FOREIGN PATENT DOCUMENTS

| EP | 0151962 | 1/1985 |
|---|---|---|
| EP | 2308866 | 4/2011 |
| WO | WO 2007002293 | 1/2007 |
| WO | WO 2011051858 | 5/2011 |

OTHER PUBLICATIONS

Bamborough, P., et al., Assessment of chemical Coverage of Kinome space and Its Implications for Kinase Drug Discovery, *J. Med. Chem.* vol. 51, 7898-7914 (2008).
Meng, Q., et al., Entrainment of disrupted circadian behavior through inhibition of casein kinase 1 (CK1) enzymes, *PNAS*, vol. 107, No. 34, 15240-15245 (2010).
Peifer, C., et al., 3, 4-Diaryl-isoxazoles and—imidazoles as Potent Dual Inhibitors of p38α Mitogen Activated Protein Kinase and Casein Kinase 1 delta, *J. Med. Chem,*, vol. 52, 7618-7630 (2009).
Perez, D., et al., Protein Kinases CK1 and CK2 as New Targets for Neurodegenerative Diseases, *Medicinal Research Reviews*, vol. 31, No. 6, 924-954 (2010).
Walton, K., et al., Selective Inhibiton of Casein Kinase 1epsilon Minimally Alters Circadian Clock Period, *The Journal of Pharmacology and Experimental Therapeutics*, vol. 330, No. 2, 430-439 (2009).
Antle and Silver, Orchestrating time: arrangements of the brain circadian clock, *Trends in Neurosciences*, vol. 28, No. 3, 145-151 (2005).
Arvanitis, A., et al., Imidazo[4,5-b]pyridines as Corticotropin releasing Factor Receptor Ligands, *Bioorganic & Medicinal Chemistry Letters*, vol. 13, 125-128 (2003).
Barnard and Nolan, When Clocks Go Bad: Neurobehavioural Consequences of Disrupted Circadian Timing, *PLoS Genetics*, vol. 4, No. 5, 1-8 (2008).
Finnin and Morgan, Transdermal Penetration Enhancers: Application, Limitations, and Potential, *Journal of Pharmaceutical Sciences*, vol. 88, No. 10, 955-958 (1999).
Flotow, H., et al., Phosphate Groups as Substrate Determinants for Casein Kinase I Action, *The Journal of Biological Chemistry*, vol. 265, No. 24, 14264-14269 (1990).
Greene, T.W., Protective Groups in Organic Chemistry, John Wiley & Sons, 1981.
Green, T.W., Protective Groups in Organic Chemistry, John Wiley & Sons, 1991.
Greene, T.W. and Wuts, PG.M., Protective Groups in Organic Chemistry, John Wiley & Sons, 1999.
Hoover, John E., Remington's Pharmaceutical Sciences, Mach Publishing Co., Easton, Pennsylvania, 1975.
Ismail, M., et al., Synthesis of Benzyloxybromobenzonitriles, *Synthetic Communications*, vol. 34, No. 5, 751-758 (2004).

(Continued)

*Primary Examiner* — Niloofar Rahmani
(74) *Attorney, Agent, or Firm* — Feng Shao

(57) ABSTRACT

Compounds and pharmaceutically acceptable salts of the compounds are disclosed, wherein the compounds have the structure of Formula I:

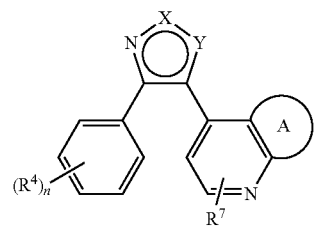

and pharmaceutically acceptable salts thereof, wherein X, Y, A, $R^4$, n, and $R^7$ are as defined in the specification. Corresponding pharmaceutical compositions, methods of treatment, methods of synthesis, and intermediates are also disclosed.

10 Claims, No Drawings

(56) References Cited

OTHER PUBLICATIONS

Kibbe, et al., Eds., Handbook of Pharmaceutical Excipients ($3^{rd}$ Ed.), American Pharmaceutical Association, Washington, 1999.

Ko and Takahashi, Molecular components of the mammalian circadian clock, *Human Molecular Genetics*, vol. 15, No. 2, 271-277 (2006).

Liberman, et al., Eds., Pharmaceutical Dosage Forms, Marcel Decker, New York, N.Y., 1980.

Lowrey, P, et al., Positional Syntenic Cloning and Functional characterization of the Mammalian Circadian Mutation tau, *Science*, vol. 288, 483-491 (2000).

Mitsunobu, O, The Use of Diethyl Azodicarboxylate and Triphenylphosphine in Synthesis and Transformation of Natural Products, *Synthesis*, 1-28 (1981).

Miyaura, N., and Suzuki, A., Palladium-Catalyzed Cross-Coupling Reactions of Organoboron Compounds, *Chem. Rev.*, vol. 95, 2457-2483 (1995).

Murry, J., et al., Synthesis of α-Amido Ketones via Organic Catalysis: Thiazolium-Catalyzed Cross-Coupling of Aldehydes with Acylimines, *J. Am. Chem. Soc.*, vol. 123, 9696-9697 (2001).

Sisko, J., et al., α-Tosylbenzyl Isocyanide, *Organic Syntheses*, vol. 10, 692 (2004).

Suzuki, A, Recent advances in the cross-coupling reactions of organoboron derivatives with organic electrophiles, 1995-1998, *Journal of Organometallic Chemistry*, vol. 576, 147-168 (1999).

Compendium of Organic Synthetic Methods, vol. I-VI (published by Wiley-Interscience)) (2006).

\* cited by examiner

FUSED PYRIDINE COMPOUNDS AS CASEIN KINASE INHIBITORS

This application claims the benefit of priority to U.S. Provisional Patent Application Ser. No. 61/425,213 filed Dec. 20, 2010, the disclosure of which is hereby incorporated by reference in its entirety.

FIELD OF THE INVENTION

This invention relates generally to pharmaceutical agents useful in the treatment and/or prevention of diseases and disorders associated with the central nervous system. More particularly, the present invention comprises compounds for the treatment of a patient suffering from a disease or disorder ameliorated by inhibition of casein kinase I delta (CK1δ) or CK1 epsilon (CK1ε) activity through the administration of a series of substituted fused pyridine compounds. More specifically the invention relates to aryl substituted 5-membered heteroaryls substituted with optionally substituted (2,3-fusedpyridin-4-yls) and related analogs which are inhibitors of human CK1δ or CK1ε phosphorylation.

BACKGROUND OF THE INVENTION

The circadian clock links our daily cycles of sleep and activity to the external environment. Deregulation of the clock is implicated in a number of human disorders, including depression, seasonal affective disorder, and metabolic disorders. Circadian rhythms are controlled in mammals by the master clock located in the suprachiasmatic nucleus of the hypothalamus (Antle and Silver, Trends Neurosci 28: 145-151). At the cellular level, the molecular events behind clock cycling are described by the regular increase and decrease in mRNAs and proteins that define feedback loops, resulting in approximately 24 hour cycles. The suprachiasmatic nucleus is primarily regulated, or entrained, directly by light via the retinohypothalamic tract. The cycling outputs of the suprachiasmatic nucleus, not fully identified, regulate multiple downstream rhythms, such as those in sleep and awakening, body temperature, and hormone secretion (Ko and Takahashi, Hum Mol Gen 15: R271-R277.). Furthermore, diseases such as depression, seasonal affective disorder, and metabolic disorders, may have a circadian origin (Barnard and Nolan, PLoS Genet. 2008 May; 4(5): e1000040).

Phosphorylation of circadian clock proteins is an essential element in controlling the cyclical rhythm of the clock. CK1ε and CK1δ are closely related Ser-Thr protein kinases that serve as key clock regulators as demonstrated by mammalian mutations in each that dramatically alter the circadian period. (Lowrey et al., Science 288: 483-492). Therefore, inhibitors of CK1δ/ε have utility in treating circadian disorders. Thus it is an object of this invention to provide compounds of Formula I that are inhibitors of CK1δ or CK1ε. This object and other objects of this invention become apparent from the detailed discussion of the invention that follows.

SUMMARY OF THE INVENTION

The invention is directed to compounds having the structure of Formula I:

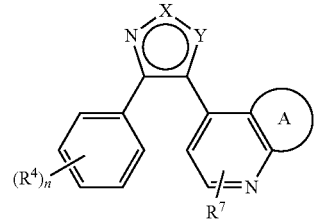

wherein X and Y are independently =N—, —NR$^1$—, CR$^1$, or —S—, provided that at least one of X and Y is CR$^1$;

Ring A is a 4- to 7-membered cycloalkyl or heterocycloalkyl or a 5- to 6-membered heteroaryl, wherein up to 2 carbon atoms are replaced with a heteroatom selected from =N—, —NR$^2$—, —O—, —S and any remaining carbon atom may be substituted with R$^3$ as valency allows;

Each R$^1$ is independently H, C$_{1-4}$alkyl, C$_{3-6}$cycloalkyl, —CF$_3$, —(CH$_2$)$_{1-3}$CF$_3$, 4- to 10-membered heterocycloalkyl, wherein said heterocycloalkyl may be substituted with up to two substituents independently selected from halogen, OH, oxo, cyano, C$_{1-6}$alkyl, or C$_{1-6}$alkyl-O—C$_{1-6}$alkyl;

Each R$^2$ is independently H, C$_{1-6}$alkyl, C$_{4-10}$-bicycloalkyl, —(CH$_2$)$_t$—CN, —SO$_2$C$_{1-6}$alkyl, —SO$_2$(CH$_2$)$_t$C$_{3-6}$cycloalkyl, —C$_{1-6}$alkyl-O—C$_{1-6}$alkyl, —C$_{1-6}$alkyl-C(O)O—C$_{1-6}$alkyl, —C$_{3-6}$cycloalkyl-C(O)O—C$_{1-6}$alkyl, —C(O)—(O)$_u$—C$_{1-6}$alkyl, —C(O)—C$_{1-6}$alkyl-O—C$_{1-6}$alkyl, —C(O)—(O)$_u$—(CH$_2$)$_t$—(C$_{6-10}$aryl), —(CH$_2$)$_t$—(C$_{6-10}$aryl), —C(O)—(O)$_u$—(CH$_2$)$_t$-(5- to 10-membered heteroaryl), —(CH$_2$)$_t$—C(O)—NR$^5$R$^6$, —(CH$_2$)$_t$-(5- to 10-membered heteroaryl), —C(O)—(O)$_u$—(CH$_2$)$_t$-(3- to 10-membered heterocycloalkyl), —(CH$_2$)$_t$-(4- to 10-membered heterocycloalkyl), —C(O)—(O)$_u$—(CH$_2$)$_t$-(3- to 10-membered cycloalkyl), or —(CH$_2$)$_t$-(3- to 10-membered cycloalkyl), wherein said aryl, heteroaryl, cycloalkyl, and heterocycloalkyl of R$^2$ may be substituted with up to two substituents independently selected from halogen, OH, cyano, C$_{1-6}$alkyl, C(O)—O—C$_{1-3}$alkyl, or C$_{1-6}$alkyl-O—C$_{1-6}$alkyl, and wherein any alkyl, cycloalkyl, and heterocycloalkyl of R$^2$ may be further substituted with oxo where valency allows;

Each R$^3$ is independently absent, C$_{1-3}$alkyl, halogen, oxo, —NR$^5$R$^6$, or —OR$^5$;

Each R$^4$ is independently halogen, —CF$_3$, C$_{1-3}$alkyl, —(CH$_2$)$_t$—C$_{3-4}$cycloalkyl, —(CH$_2$)$_t$—O—C$_{1-3}$alkyl, —(CH$_2$)$_t$-cyano, or —(CH$_2$)$_t$-hydroxy;

Each R$^5$ is independently H or C$_{1-6}$alkyl;

Each R$^6$ is independently H or C$_{1-6}$alkyl;

R$^7$ is H, halogen, or C$_{1-3}$alkyl;

n is 0, 1, or 2;

Each t is independently 0, 1 or 2;

Each u is independently 0 or 1;

and pharmaceutically acceptable salts thereof.

This invention also includes pharmaceutically acceptable salts, hydrates, solvates, isomers, crystalline and non-crystalline forms, isomorphs, polymorphs, and metabolites of compounds of Formula I. This invention also includes all tautomers and stereochemical isomers of these compounds.

This invention relates generally to pharmaceutical agents and pharmaceutically acceptable salts thereof useful in the treatment and/or prevention of diseases and disorders associated with the central nervous system. More particularly, the present invention comprises compounds for the treatment of a patient suffering from a disease or disorder ameliorated by inhibition of CK1δ or CK1ε activity through the administration of a series of substituted fused pyridine compounds of Formula I.

When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations to the invention, the scope of which is defined by the appended claims.

DETAILED DESCRIPTION

One embodiment of the present invention is a compound of Formula I as described above.

Another embodiment of compounds of Formula I include wherein each $R^1$ is independently H or $C_{1-4}$alkyl;

Each $R^2$ is independently H, $C_{1-6}$alkyl, —$SO_2C_{1-6}$alkyl, —$SO_2(CH_2)_tC_{3-6}$cycloalkyl, —$C_{1-6}$alkyl-O—$C_{1-6}$alkyl, —C(O)—(O)$_u$—$C_{1-6}$alkyl, —$(CH_2)_t$—$(C_{6-10}$aryl), —C(O)—(O)$_u$—$(CH_2)_t$-(5- to 10-membered heteroaryl), —$(CH_2)_t$—C(O)—$NR^5R^6$, —$(CH_2)_t$-(5- to 10-membered heteroaryl), —$(CH_2)_t$-(4- to 10-membered heterocycloalkyl), or —$(CH_2)_t$-(3- to 10-membered cycloalkyl), wherein said aryl, heteroaryl, cycloalkyl, and heterocycloalkyl of $R^2$ may be substituted with up to two substituents independently selected from halogen, OH, cyano, —$C_{1-6}$alkyl, —C(O)—O—$C_{1-3}$alkyl, or $C_{1-6}$alkyl-O—$C_{1-6}$alkyl, and wherein any alkyl, cycloalkyl, and heterocycloalkyl of $R^2$ may be further substituted with oxo where valency allows;

Each $R^3$ is independently absent, $C_{1-3}$alkyl, oxo, —$NR^5R^6$, or —$OR^5$;

$R^4$ is halogen;

Each $R^5$ is H;

Each $R^6$ is independently H or $C_{1-6}$alkyl;

$R^7$ is H;

n is 1;

Each t is independently 0, 1 or 2;

Each u is independently 0 or 1;

X, Y, and A are as defined in any other embodiment of Formula I;

and pharmaceutically acceptable salts thereof.

The invention also concerns compounds wherein A of Formula I in any embodiment discussed herein is any of the following:

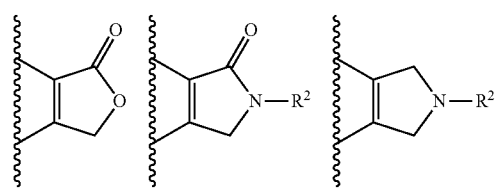

-continued

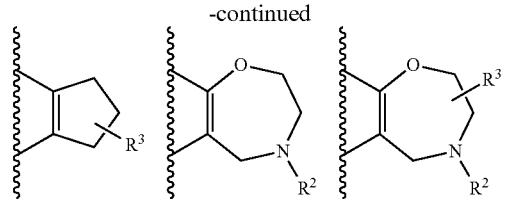

wherein $R^2$ and $R^3$ are as defined for embodiment of Formula I or any group of definitions described herein, with the understanding that there can be as many $R^3$ substituents as valency allows although only one is drawn above for simplicity. Furthermore, when there is no substitution on a carbon of A, then $R^3$ is absent.

Another embodiment of compounds of Formula I includes compounds where A of Formula I is substituted on an available nitrogen by $R^2$ wherein $R^2$ is independently H, —$CH_3$, or $SO_2CH_3$; and where A of Formula I is substituted on an available carbon by $R^3$ wherein $R^3$ is independently absent or oxo. Another embodiment is where A of Formula I is further substituted on at least one carbon with $R^3$ as described herein of any embodiment of Formula I.

Another embodiment of the invention includes compounds of Formula I wherein X is $NR^1$ where $R^1$ is $C_{1-4}$ alkyl or $C_{3-4}$cycloalkyl; Y is $CR^1$ where $R^1$ is H or $CH_3$; A a lactone, lactam, or isoindolinyl substituted as allowed in any embodiment of Formula I; $R^4$ is F, and $R^7$ is H. Using moieties for A, another way to present this embodiment of the invention is wherein X is $NR^1$ where $R^1$ is $C_{1-4}$ alkyl or $C_{3-4}$cycloalkyl; Y is $CR^1$ where $R^1$ is H or $CH_3$; A is

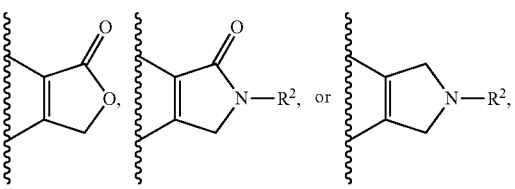

substituted as allowed in any embodiment of Formula I; $R^4$ is F, and $R^7$ is H.

It will be understood that the compounds of Formula I, and pharmaceutically acceptable salts thereof, also include hydrates, solvates and polymorphs of said compounds of Formula I and pharmaceutically acceptable salts thereof, as discussed below.

In one embodiment, the invention also relates to each of the individual compounds described herein as Examples 1 to 52 (including the free bases or pharmaceutically acceptable salts thereof).

In another embodiment the invention relates to any one compound or any group of compounds independently selected from the group consisting of:
6-benzyl-4-[3-(4-fluorophenyl)-1-methyl-1H-pyrazol-4-yl]-5,6-dihydro-7H-pyrrolo[3,4-b]pyridin-7-one;
4-[3-(4-fluorophenyl)-1-methyl-1H-pyrazol-4-yl]-7,8-dihydro-1,7-naphthyridin-6(5H)-one;
4-[3-(4-fluorophenyl)-1-methyl-1H-pyrazol-4-yl]-5,6,7,8-tetrahydro-1,7-naphthyridine;
7-[3-(4-fluorophenyl)-1-methyl-1H-pyrazol-4-yl]-2-methyl[1,3]oxazolo[5,4-b]pyridine;
7-[3-(4-fluorophenyl)-1-methyl-1H-pyrazol-4-yl]-2-methyl[1,3]oxazolo[4,5-b]pyridine;

7-[3-(4-fluorophenyl)-1-methyl-1H-pyrazol-4-yl]-1-methyl-1H-pyrazolo[4,3-b]pyridine;
4-[3-(4-fluorophenyl)-1-methyl-1H-pyrazol-4-yl]-1H-pyrazolo[3,4-b]pyridine;
4-[3-(4-fluorophenyl)-1-methyl-1H-pyrazol-4-yl]-2-methyl-2H-pyrazolo[3,4-b]pyridine;
4-[3-(4-fluorophenyl)-1-methyl-1H-pyrazol-4-yl]-1-methyl-1H-pyrazolo[3,4-b]pyridine;
7-acetyl-4-[3-(4-fluorophenyl)-1-methyl-1H-pyrazol-4-yl]-6,7,8,9-tetrahydro-5H-pyrido[2,3-d]azepine;
4-[3-(4-fluorophenyl)-1-methyl-1H-pyrazol-4-yl]-7-(methylsulfonyl)-6,7,8,9-tetrahydro-5H-pyrido[2,3-d]azepine;
4-[3-(4-fluorophenyl)-1-methyl-1H-pyrazol-4-yl]-6,7,8,9-tetrahydro-5H-pyrido[2,3-d]azepine;
4-[3-(4-fluorophenyl)-1-methyl-1H-pyrazol-4-yl]-5,6,7,8-tetrahydro-1,6-naphthyridine;
ethyl 4-[3-(4-fluorophenyl)-1-methyl-1H-pyrazol-4-yl]-7,8-dihydro-1,6-naphthyridine-6(5H)-carboxylate;
4-[3-(4-fluorophenyl)-1-methyl-1H-pyrazol-4-yl]-7,8-dihydro-1,6-naphthyridin-5(6H)-one; and
4-[3-(4-fluorophenyl)-1-methyl-1H-pyrazol-4-yl]-6-methyl-7,8-dihydro-1,6-naphthyridin-5(6H)-one; or as a pharmaceutically acceptable salt thereof.

In another embodiment, the invention relates to methods for inhibiting casein kinase 1 CK1 delta or CK1 epsilon activity in a patient comprising the administration of a therapeutically effective amount of an inhibitor of casein kinase1 CK1 delta or CK1 epsilon.

In another embodiment, the invention relates to methods of inhibiting casein kinase CK1 delta or CK1 epsilon activity which result in a lengthening of the circadian rhythm period.

In another embodiment, the invention relates to a method of treating or preparation of a medicament to treat a mood disorder or a sleep disorder comprising the administration of a therapeutically effective amount of an inhibitor of casein kinase1 CK1 delta or CK1 epsilon. In one embodiment, the invention relates to a method of treating a sleep disorder. In a further embodiment, the sleep disorder is a circadian rhythm sleep disorder. In yet another embodiment, the circadian rhythm sleep disorder is selected from the group consisting of shift work sleep disorder, jet lag syndrome, advanced sleep phase syndrome and delayed sleep phase syndrome.

In a further embodiment, the invention relates to a method of treating or preparation of a medicament to treat a mood disorder selected from the group consisting of a depressive disorder and a bipolar disorder. In another embodiment of the invention, the depressive disorder is major depressive disorder. In a further embodiment of the invention, the mood disorder is a bipolar disorder. In another embodiment, the bipolar disorder is selected from the group consisting of bipolar I disorder and bipolar II disorder.

In another embodiment the present invention provides methods of treating or preparation of a medicament to treat neurological and psychiatric disorders comprising: administering to a mammal an amount of a compound of Formula I effective in treating such disorders, or a pharmaceutically acceptable salt thereof. Neurological and psychiatric disorders include but are not limited to: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia, AIDS-induced dementia, vascular dementia, mixed dementias, age-associated memory impairment, Alzheimer's disease, Huntington's Chorea, amyotrophic lateral sclerosis, ocular damage, retinopathy, cognitive disorders, including cognitive disorders associated with schizophrenia and bipolar disorders, idiopathic and drug-induced Parkinson's disease, muscular spasms and disorders associated with muscular spasticity including tremors, epilepsy, convulsions, migraine, migraine headache, urinary incontinence, substance tolerance, substance withdrawal, withdrawal from opiates, nicotine, tobacco products, alcohol, benzodiazepines, cocaine, sedatives, and hypnotics, psychosis, mild cognitive impairment, amnestic cognitive impairment, multi-domain cognitive impairment, obesity, schizophrenia, anxiety, generalized anxiety disorder, social anxiety disorder, panic disorder, post-traumatic stress disorder, obsessive compulsive disorder, mood disorders, depression, mania, bipolar disorders, trigeminal neuralgia, hearing loss, tinnitus, macular degeneration of the eye, emesis, brain edema, pain, acute and chronic pain states, severe pain, intractable pain, neuropathic pain, post-traumatic pain, tardive dyskinesia, sleep disorders, narcolepsy, attention deficit/hyperactivity disorder, autism, Asperger's disease, and conduct disorder in a mammal. Accordingly, in one embodiment, the invention provides a method for treating a condition in a mammal, such as a human, selected from the conditions above, comprising administering a compound of Formula I to the mammal. The mammal is preferably a mammal in need of such treatment.

As examples, the invention provides a method for treating or preparation of a medicament to treat attention deficit/hyperactivity disorder, schizophrenia and Alzheimer's Disease.

In another embodiment the present invention provides methods of treating neurological and psychiatric disorders comprising: administering to a patient in need thereof an amount of a compound of Formula I effective in treating such disorders. The compound of Formula I is optionally used in combination with another active agent. Such an active agent may be, for example, an atypical antipsychotic, a cholinesterase inhibitor, Dimebon, or NMDA receptor antagonist. Such atypical antipsychotics include, but are not limited to, ziprasidone, clozapine, olanzapine, risperidone, quetiapine, aripiprazole, paliperidone; such NMDA receptor antagonists include but are not limited to memantine; and such cholinesterase inhibitors include but are not limited to donepezil and galantamine.

The invention is also directed to a pharmaceutical composition comprising a compound of Formula I, and a pharmaceutically acceptable carrier. The composition may be, for example, a composition for treating a condition selected from the group consisting of neurological and psychiatric disorders, including but not limited to: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia, AIDS-induced dementia, vascular dementia, mixed dementias, age-associated memory impairment, Alzheimer's disease, Huntington's Chorea, amyotrophic lateral sclerosis, ocular damage, retinopathy, cognitive disorders, including cognitive disorders associated with schizophrenia and bipolar disorders, idiopathic and drug-induced Parkinson's disease, muscular spasms and disorders associated with muscular spasticity including tremors, epilepsy, convulsions, migraine, migraine headache, urinary incontinence, substance tolerance, substance withdrawal, withdrawal from opiates, nicotine, tobacco products, alcohol, benzodiazepines, cocaine, sedatives, and hypnotics, psychosis, mild cognitive impairment, amnestic cognitive impairment, multi-domain cognitive impairment, obesity, schizophrenia, anxiety, generalized anxiety disorder, social anxiety disorder, panic disorder, post-traumatic stress disorder, obsessive compulsive disorder, mood disorders, depression, mania, bipolar disorders, trigeminal neuralgia, hearing loss, tinnitus, macular degeneration of the eye, emesis, brain edema, pain, acute and chronic pain states, severe pain, intractable pain, neuropathic pain, post-traumatic pain, tardive dyskinesia, sleep disorders, narcolepsy, attention deficit/hyperactivity disorder, autism, Asperger's disease, and conduct disorder in a mammal, comprising administering an effective amount of a compound of formula I or pharmaceutically acceptable salt thereof, and a pharmaceutically acceptable carrier. The composition optionally further comprises an atypical antipsychotic, a cholinesterase inhibitor, Dimebon, or NMDA receptor antagonist. Such atypical antipsychotics include, but are not limited to, ziprasidone, clozapine, olanzapine, risperidone, quetiapine, aripiprazole, paliperidone; such NMDA receptor antagonists include but are not limited to memantine; and such cholinesterase inhibitors include but are not limited to donepezil and galantamine.

The compounds of the present invention are also adapted to therapeutic use as antiproliferative agents (e.g., cancer), anti-tumor (e.g., effect against solid tumors) in mammals, particularly in humans. In particular, the compounds of the present invention are useful in the prevention and treatment of a variety of human hyperproliferative disorders including both malignant and benign abnormal cell growth.

The compounds, compositions and methods provided herein are useful for the treatment of cancer and preparation of a medicament to treat cancer including but are not limited to:

circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue;

respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

gastrointestinal, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma);

bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs;

hematologic, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx;

skin, for example, malignant melanoma, cutaneous melanoma, basal cell carcinoma, squamous cell carcinoma, Karposi's sarcoma, moles dysplastic nevi, lipoma, angioma, dermatofibroma, and keloids;

adrenal glands: neuroblastoma; and cancers involving other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of "cancer" when used herein in connection with the present invention include cancer selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

Still more specifically, examples of "cancer" when used herein in connection with the present invention include cancer selected from lung cancer (NSCLC and SCLC), breast cancer, ovarian cancer, colon cancer, rectal cancer, cancer of the anal region, or a combination of one or more of the foregoing cancers.

In one embodiment of the present invention the non-cancerous conditions include such hyperplastic conditions such as benign hyperplasia of the skin (e.g., psoriasis) and benign hyperplasia of the prostate (e.g., BPH).

As noted above, the compounds of the invention may be used in combination with one or more additional anti-cancer agents which are described below. When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of Formula I, as defined above (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

DEFINITIONS

The term "alkyl" refers to a linear or branched-chain saturated hydrocarbyl substituent (i.e., a substituent obtained from a hydrocarbon by removal of a hydrogen) containing from one to twenty carbon atoms; in one embodiment from one to twelve carbon atoms; in another embodiment, from one to ten carbon atoms; in another embodiment, from one to six carbon atoms; and in another embodiment, from one to four carbon atoms. Examples of such substituents include methyl, ethyl, propyl (including n-propyl and isopropyl), butyl (including n-butyl, isobutyl, sec-butyl and tert-butyl), pentyl, isoamyl, hexyl and the like. In some instances, the number of carbon atoms in a hydrocarbyl substituent (i.e., alkyl, alkenyl, cycloalkyl, aryl, etc.) is indicated by the prefix "$C_{a-b}$," wherein a is the minimum and b is the maximum number of carbon atoms in the substituent. Thus, for example, "$C_{1-6}$alkyl" refers to an alkyl substituent containing from 1 to 6 carbon atoms.

"Alkenyl" refers to an aliphatic hydrocarbon having at least one carbon-carbon double bond, including straight chain, branched chain or cyclic groups having at least one carbon-carbon double bond. Preferably, it is a medium size alkenyl having 2 to 6 carbon atoms. For example, as used herein, the term "$C_{2-6}$alkenyl" means straight or branched chain unsaturated radicals of 2 to 6 carbon atoms, including, but not limited to ethenyl, 1-propenyl, 2-propenyl (allyl), isopropenyl, 2-methyl-1-propenyl, 1-butenyl, 2-butenyl, and the like; optionally substituted by 1 to 5 suitable substituents as defined above such as fluoro, chloro, trifluoromethyl, ($C_1$-$C_6$) alkoxy, ($C_6$-$C_{10}$)aryloxy, trifluoromethoxy, difluoromethoxy or $C_1$-$C_6$alkyl. When the compounds of the invention contain a $C_{2-6}$alkenyl group, the compound may exist as the pure E (entgegen) form, the pure Z (zusammen) form, or any mixture thereof.

"Alkynyl" refers to an aliphatic hydrocarbon having at least one carbon-carbon triple bond, including straight chain, branched chain or cyclic groups having at least one carbon-carbon triple bond. Preferably, it is a lower alkynyl having 2 to 6 carbon atoms. For example, as used herein, the term "$C_{2-6}$alkynyl" is used herein to mean a straight or branched hydrocarbon chain alkynyl radical as defined above having 2 to 6 carbon atoms and one triple bond.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Cycloalkyl may be a single ring, which typically contains from 3 to 6 ring atoms. Examples of cycloalkyl include cyclopropyl, cyclobutyl, cyclopentyl and cyclohexyl. Alternatively, cycloalkyl may be 2 or 3 rings fused together, such as bicyclo[4.2.0]octane and decalinyl and may also be referred to as "bicycloalkyl".

The term "cycloalkyl" also includes substituents that are fused to a $C_6$-$C_{10}$ aromatic ring or to a 5- to 10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or 5-10-membered heteroaromatic ring may be optionally substituted with halogen, $C_{1-6}$alkyl, $C_{3-10}$cycloalkyl, or =O.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_{4-10}$ carbocyclic ring, such as a $C_5$ or a $C_6$ carbocyclic ring, or to a 4- to 10-membered heterocyclic ring, wherein a group having such a fused aryl group as a substituent is bound to an aromatic carbon of the aryl group. When such a fused aryl group is substituted with one more substituents, the one or more substitutents, unless otherwise specified, are each bound to an aromatic carbon of the fused aryl group. The fused $C_{4-10}$ carbocyclic or 4- to 10-membered heterocyclic ring may be optionally substituted with halogen, $C_{1-6}$alkyl, $C_{3-10}$cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

In some instances, the number of atoms in a cyclic substituent containing one or more heteroatoms (i.e., heteroaryl or heterocycloalkyl) is indicated by the prefix "A-B-membered", wherein A is the minimum and B is the maximum number of atoms forming the cyclic moiety of the substituent. Thus, for example, 5- to 8-membered heterocycloalkyl refers to a heterocycloalkyl containing from 5 to 8 atoms, including one or more heteroatoms, in the cyclic moiety of the heterocycloalkyl.

The term "hydrogen" refers to a hydrogen substituent, and may be depicted as —H.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents are attached include, for example, alcohols, enols and phenol.

The term "cyano" (also referred to as "nitrile") means —CN, which also may be depicted:

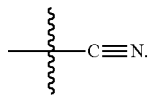

The term "halogen" refers to fluorine (which may be depicted as —F), chlorine (which may be depicted as —Cl), bromine (which may be depicted as —Br), or iodine (which may be depicted as —I). In one embodiment, the halogen is chlorine. In another embodiment, the halogen is fluorine. In another embodiment, the halogen is bromine.

The term "heterocycloalkyl" refers to a substituent obtained by removing a hydrogen from a saturated or partially saturated ring structure containing a total of 4 to 14 ring atoms, wherein at least one of the ring atoms is a heteroatom selected from oxygen, nitrogen, or sulfur. For example, as used herein, the term "4- to 10-membered heterocycloalkyl" means the substituent is a single ring with 4 to 10 total members. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_{6-10}$ aromatic ring or to a 5- to 10-membered heteroaromatic ring, wherein a group having such a fused heterocycloalkyl group as a substituent is bound to a heteroatom of the heterocycloalkyl group or to a carbon atom of the heterocycloalkyl group. When such a fused heterocycloalkyl group is substituted with one or more substituents, the one or more substituents, unless otherwise specified, are each bound to a heteroatom of the heterocycloalkyl group or to a carbon atom of the heterocycloalkyl group. The fused $C_6$-$C_{10}$ aromatic ring or 5- to 10-membered heteroaromatic ring may be optionally substituted with halogen, $C_{1-6}$alkyl, $C_{3-10}$cycloalkyl, $C_{1-6}$alkoxy, or =O.

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include but are not limited to: 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused ring substituents such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single-ring heteroaryls and heterocycloalkyls include but are not limited to furanyl, dihydrofuranyl, tetrahydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, isoxazolinyl, thiazolyl, isothiazolyl, thiazolinyl, isothiazolinyl, thiazolidinyl, isothiazolidinyl, thiadiazolyl, oxathiazolyl, oxadiazolyl (including oxadiazolyl, 1,2,4-oxadiazolyl (also known as "azoximyl"), 1,2,5-oxadiazolyl (also known as "furazanyl"), or 1,3,4-oxadiazolyl), pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), morpholinyl, azepinyl, oxepinyl, thiepinyl, and diazepinyl.

Examples of 2-fused-ring heteroaryls include but are not limited to indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

Examples of 3-fused-ring heteroaryls or heterocycloalkyls include but are not limited to 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl. Other examples of fused-ring heteroaryls include but are not limited to benzo-fused heteroaryls such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothionaphthenyl," or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "heteroaryl" also includes substituents such as pyridyl and quinolinyl that are fused to a $C_{4-10}$ carbocyclic ring, such as a $C_5$ or a $C_6$ carbocyclic ring, or to a 4-10-membered heterocyclic ring, wherein a group having such a fused heteroaryl group as a substituent is bound to an aromatic carbon of the heteroaryl group or to a heteroatom of the heteroaryl group. When such a fused heteroaryl group is substituted with one or more substituents, the one or more substitutents, unless otherwise specified, are each bound to an aromatic carbon of the heteroaryl group or to a heteroatom of the heteroaryl group. The fused $C_{4-10}$ carbocyclic or 4-10-membered heterocyclic ring may be optionally substituted with halogen, $C_{1-6}$ alkyl, $C_{3-10}$ cycloalkyl, or =O.

Additional examples of heteroaryls and heterocycloalkyls include but are not limited to: 6,7-dihydro-5H-pyrrolo[3,4-b]pyridin-5-one, 6,7-dihydro-5H-pyrrolo[3,4-b]pyridyl, furo[3,4-b]pyridin-5(7H)-one, 2,3,4,5-tetrahydropyrido[2,3-f][1,4]oxazepine, 6,7-dihydro-5H-cyclopenta[b]pyridyl, 5,6,7,8-tetrahydro-1,7-naphthyridyl, furo[3,4-b]pyridin-7(5H)-one, 7,8-dihydro-1,7-naphthyridin-6(5H)-one, 5H-pyrrolo[3,4-b]pyridin-7(6H)-one, 7,8-dihydro-1,6-naphthyridin-5(6H)-one, 1H-pyrazolo[3,4-b]pyridyl, 5,6,7,8-tetrahydro-1,6-naphthyridyl, 2H-pyrazolo[4,3-b]pyridyl, 6,7,8,9-tetrahydro-5H-pyrido[2,3-d]azepine, oxazolo[4,5-b]pyridyl, oxazolo[5,4-b]pyridyl, 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzo[1,3]dioxine, benzo[1,4]dioxine, benzopyrrolidinyl, benzopiperidinyl, benzoxolanyl, benzothiolanyl, 4,5,6,7-tetrahydropyrazol[1,5-a]pyridine, benzothianyl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted," a non-hydrogen substituent is in the place of a hydrogen substituent on a carbon or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described such that it "may be substituted" or as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached may form a heterocyclic ring comprising 1 or 2 heteroatoms independently selected from oxygen, nitrogen, or sulfur, wherein said heterocycloalkyl moiety may be optionally substituted. The heterocyclic ring formed from R' and R" together with the nitrogen atom to which they are attached may be partially or fully saturated, or aromatic. In one embodiment, the heterocyclic ring consists of 4 to 10 atoms. In another embodiment, the heterocyclic ring is selected from the group consisting of piperidinyl, morpholinyl, azetidinyl, pyrrolyl, imidazolyl, pyrazolyl, triazolyl, tetrazolyl, isoxazolyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described such that it "may be substituted" or as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, a $C_{1-6}$-prefix on $C_{1-6}$alkylcycloalkyl means that the alkyl moiety of the alkylcycloalkyl contains from 1 to 6 carbon atoms; the $C_{1-6}$-prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If the halogen substitution only occurs on the alkyl moiety, the substituent would be described as "alkoxyhaloalkyl." If the halogen substitution occurs on both the alkyl moiety and the alkoxy moiety, the substituent would be described as "haloalkoxyhaloalkyl."

If substituents are described as being "independently selected" from a group, each substituent is selected independent of the other(s). Each substituent therefore may be identical to or different from the other substituent(s).

As used herein the term "Formula I" may be hereinafter referred to as a "compound(s) of the invention." Such terms are also defined to include all forms of the compound of Formula I, including hydrates, solvates, isomers, crystalline and non-crystalline forms, isomorphs, polymorphs, and metabolites thereof. For example, the compounds of Formula I, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of Formula I containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of Formula I may have asymmetric carbon atoms. The carbon-carbon bonds of the compounds of Formula I may be depicted herein using a solid line (——), a solid wedge (——), or a dotted wedge ( ........ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomena of tautomerism and structural isomerism. For example, the compounds of Formula I may exist in several tautomeric forms, including the enol and imine forms, and the keto and enamine forms, and geometric isomers and mixtures thereof. All such tautomeric forms are included within the scope of compounds of Formula I. Tautomers exist as mixtures of a tautomeric set in solution. In solid form, usually one tautomer predominates. Even though one tautomer may be described, the present invention includes all tautomers of the compounds of Formula I.

The present invention also includes isotopically-labeled compounds, which are identical to those recited in Formula I above, but for the fact that one or more atoms are replaced by an atom having an atomic mass or mass number different from the atomic mass or mass number usually found in nature. Examples of isotopes that may be incorporated into compounds of Formula I include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$ $^{18}F$, and $^{36}Cl$. Certain isotopically-labeled compounds of Formula I, for example those into which radioactive isotopes such as $^3H$ and $^{14}O$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of Formula I may generally be prepared by carrying out the procedures disclosed in the Schemes and/or in the Examples and Preparations below, by substituting an isotopically-labeled reagent for a non-isotopically-labeled reagent.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-benzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronised suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3$^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

In another embodiment, the invention relates to the novel intermediates useful for preparing the compounds of the invention.

GENERAL SYNTHETIC SCHEMES

The compounds of the Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Experimental Procedures and Working Examples

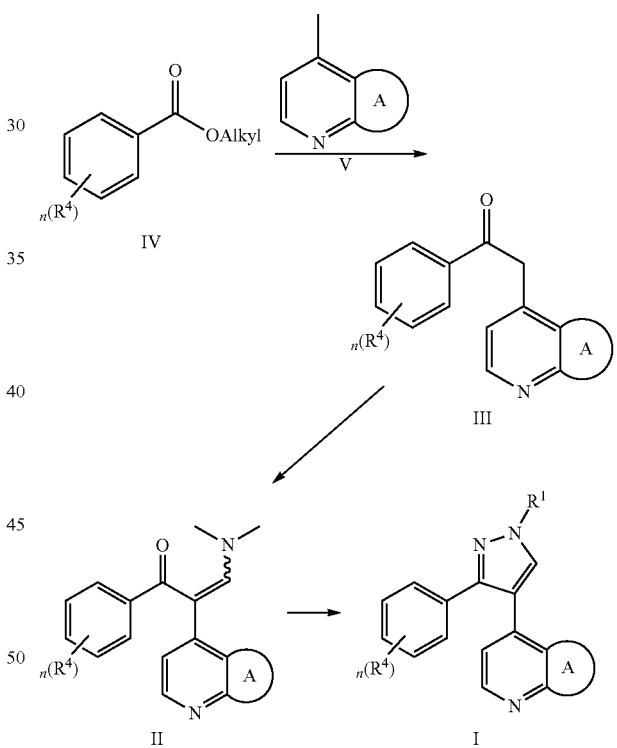

Compounds of Formula I may be synthesized following the general procedure shown in Scheme 1. Picolines of formula V may be treated with suitably strong, non-nucleophilic bases such as LDA, NaHMDS or LiHMDS in tetrahydrofuran (THF) or ethyl ether and then reacted with benzoates of Formula IV to yield ketone III. Vinylogous amide II can be obtained by treating ketone III with Brederecks reagent or DMF-DMA neat or with a non-reactive solvent such as $CH_2Cl_2$. Addition of $R^1$ substituted hydrazines in alcohol solvent such as ethanol (EtOH), isopropanol or methanol (MeOH) at temperatures ranging from rt to 100° C. yields pyrazole of Formula I.

Scheme 2

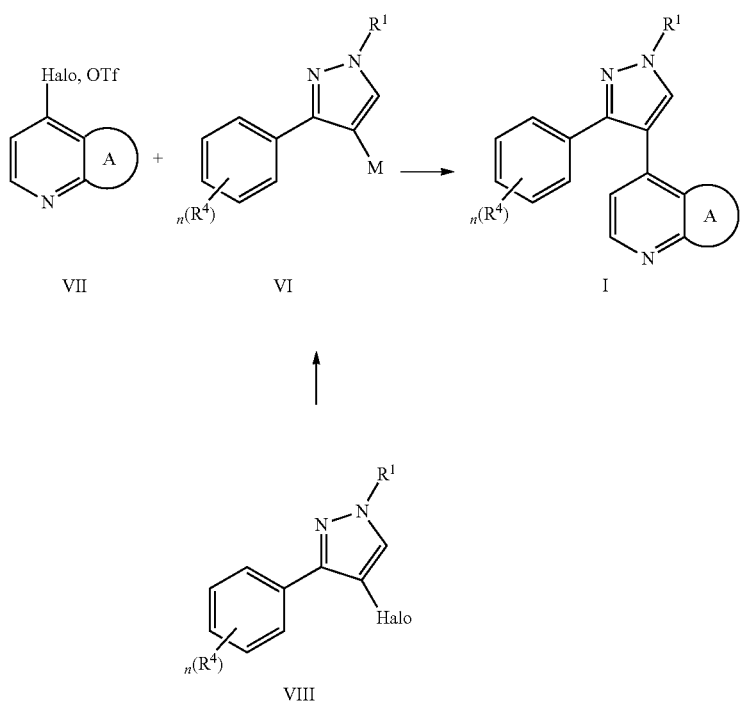

Compounds of Formula I may also be synthesized following the general procedure shown in Scheme 2. When M is a boronic acid or a pinacol borane, generation of intermediate VI may be accomplished first by halogen-metal exchange on halocompound of formula VIII with an alkylmetal reagent such as n-BuLi, sec-BuLi or tert-butyl lithium or alkyl Grignard where isopropyl magnesium chloride-lithium chloride complex is preferred. Treatment of this metallo species with trialkoxyborates or 2-isopropoxy-4,4,5,5-tetramethyl-1,3,2-dioxaborolane affords the corresponding boronic acid or pinacol borane VI. The pinacol borane may also be prepared from the corresponding halide VIII via coupling with bis(pinacolato)diboron in the presence of a palladium catalyst preferably Pd(dppf)Cl$_2$ in the presence of a base such as KF, K$_2$CO$_3$, K$_3$PO$_4$ or preferably Cs$_2$CO$_3$ in a polar solvent such as dimethyl acetamide or preferably dimethylformamide (DMF) at temperatures ranging from 50° C. to 120° C. where 80° C.-100° C. is preferred. The boronic acid or pinacol borane VI may be coupled with halide/triflate VII under standard palladium catalyzed cross-coupling reaction conditions well known to one of ordinary skill in the art to provide the compound of Formula I. [Suzuki, A., Journal of Organometallic Chemistry, 576, 147-169 (1999), Miyaura and Suzuki, Chemical Reviews, 95, 2457-2483 (1995).] More specifically, the aryl iodinate, bromate or triflate of Formula VII is combined with 1 to 3 equivalents of aryl pinacol borane and a suitable base, such as 2 to 5 equivalents of Cs$_2$CO$_3$, in a suitable organic solvent such as DMF. A palladium catalyst is added, such as 0.02 equivalents of tris(dibenzylidineacetone)dipalladium (0), and the reaction mixture is heated to temperatures ranging from 60° C. to 100° C. for 1 to 24 hr. The reaction is not limited to the employment of this solvent, base, or catalyst as many other conditions may be used.

Scheme 3

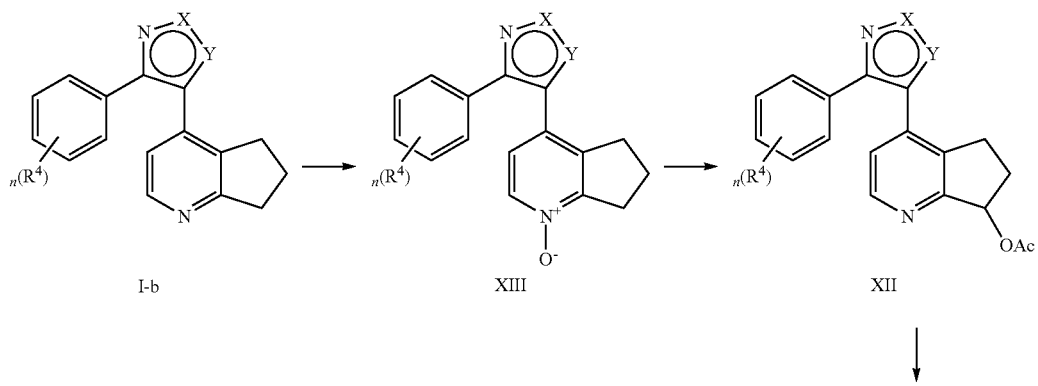

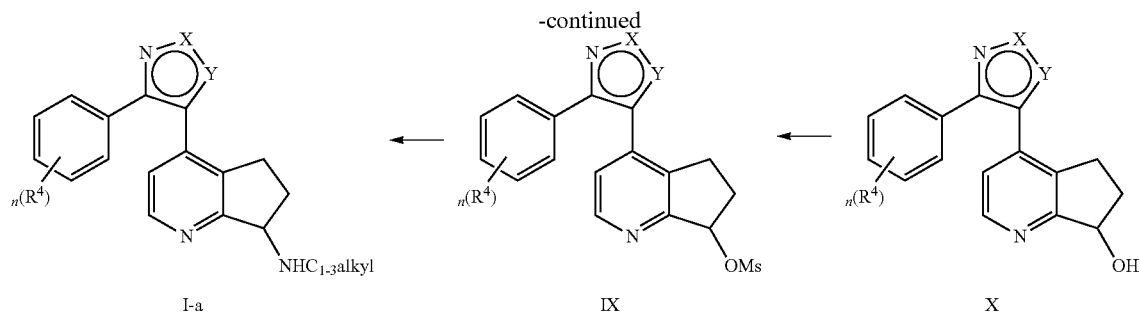

7-Amino-6,7-dihydro-5H-cyclopenta[b]pyridine of Formula I-a may be prepared as described in Scheme 3. Compound I-b (prepared following general procedures described in Schemes 1 or 2) may be converted to N-oxide XIII using oxidizing agents such as hydrogen peroxide in acetic acid or m-chloroperbenzoic acid in suitably inert solvents such as $CH_2Cl_2$. Treatment of XII with acetic anhydride at temperatures ranging from rt to 110° C. where 75° C. to 110° C. is preferred, affords acetate of formula XII. Hydroylsis of XII to give alcohol X may be accomplished with aq. inorganic bases such as sodium or potassium hydroxide or sodium or potassium carbonate and an alcohol co-solvent such as MeOH or EtOH at temperatures ranging from rt to 100° C. Conversion of X to mesylate IX may be done with methanesulfonyl anhydride or methanesulfonyl chloride in solvents such as $CH_2Cl_2$, THF or acetonitrile at temperatures in the range of −20° C. to 50° C. where 0° C. to rt is preferred. Treatment of mesylate IX with an alkylamine in a polar, non-nucleophilic solvent such as THF or dioxane gives I-a.

Scheme 4

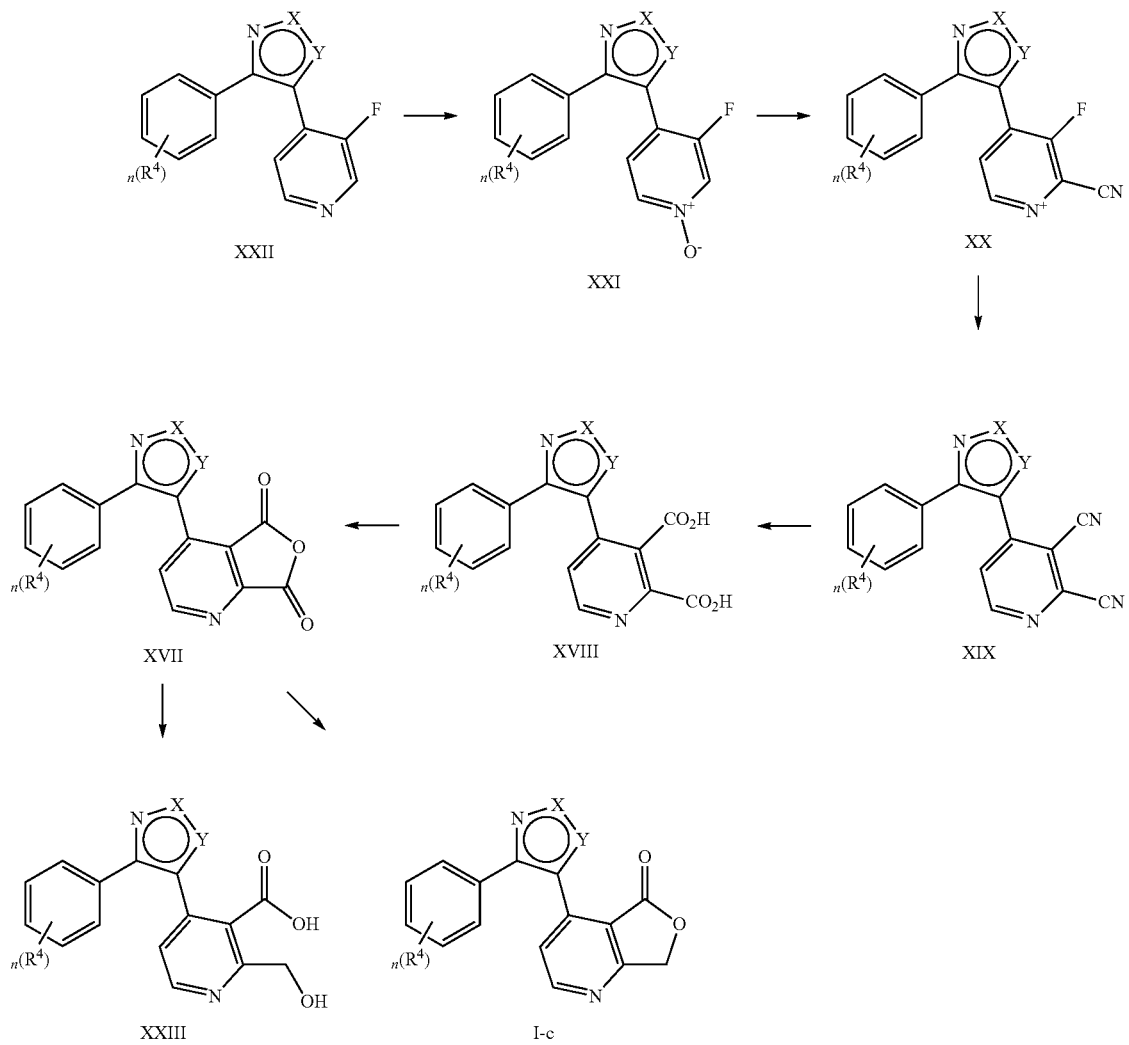

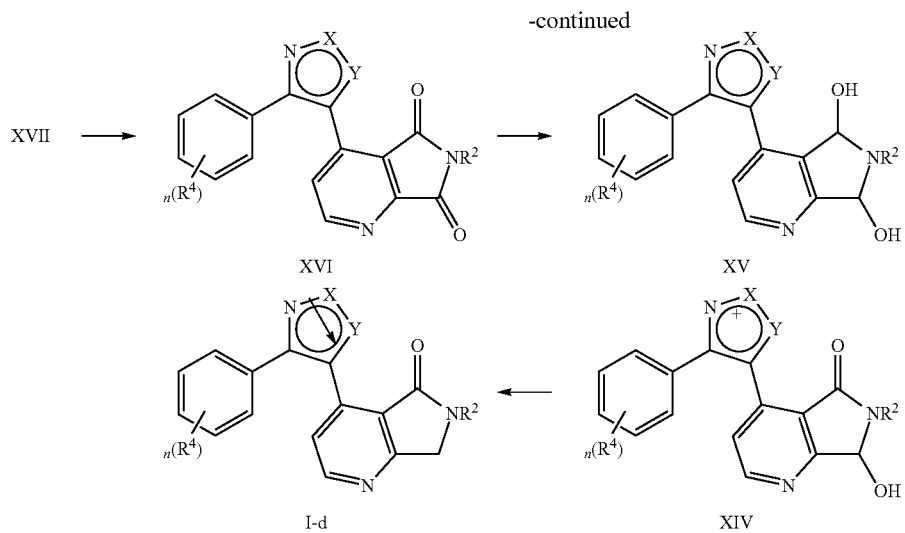

Lactone of Formula I-c and lactam of Formula I-d may be prepared as outlined in Scheme 4. Fluoropyridine XXII (prepared using the general methods described in Schemes 1 and 2) may be converted to N-oxide XXI using the general methods described in the description for Scheme 3. Treatment of XXI with tetramethylsilylcyanide in THF with or without the presence of a catalytic amount of dimethylcarbamoyl chloride at temperatures ranging from 0° C. to solvent reflux affords nitrile of formula XX. Dinitrile XIX may be prepared by treating XX with a cyanide source such as tetraalkylammonium cyanide (tetrabutylammonium cyanide for instance) or potassium or sodium cyanide in THF, dimethyl sulfoxide (DMSO) or DMF at temperatures ranging from rt to 50° C. Conversion of XIX into diacid XVIII is may be accomplished by treatment with aq. sodium or potassium hydroxide, where potassium hydroxide is preferred at temperatures in the 0° C. to 110° C. range where 75° C. to 100° C. is preferred. Anhydride XVII may be obtained by treating diacid XVIII with acetic anhydride neat or with acetic acid as solvent at 75° C. to 100° C. Reduction of XVII with sodium borohydride/ acetic acid to give alcohol-acid XXIII which then cyclizes to yield latone 1-c using acetic acid/acetic anhydride as described by Inoue, et al (Synthesis, 1, 113, 1997). Lactone I-c may also be prepared from the common anhydride intermediate XVII by regioselective reduction with zinc in acetic acid at 25° C. to 100° C. where 50° C. to 80° C. is preferred.

Lactam I-d may be prepared as follows. Reaction of XVII with ammonia or primary amine in acetic acid, with or without a catalytic amount of acetic anhydride at temperatures of 75° C. to 110° C. yields phthalamide of formula XVI. Regioselective reduction of XVI with zinc in acetic acid at 25° C. to 100° C. where 50° C. to 80° C. is preferred affords lactam of Formula I-d. I-d may also be prepared by stepwise reduction of XVI with hydride reagents such as sodium borohydride in alcoholic solvents such as MeOH to yield mixtures of alcohols of formula XIV and XV. These may be separated chromatographically and then XIV may be reduced further to afford I-d using a hydride source such as triethylsilane in a suitable strong acid such as trifluoroacetic acid (TFA) either neat or with $CH_2Cl_2$ as co-solvent. This transformation may be accomplished at from rt to reflux temperatures.

Scheme 5

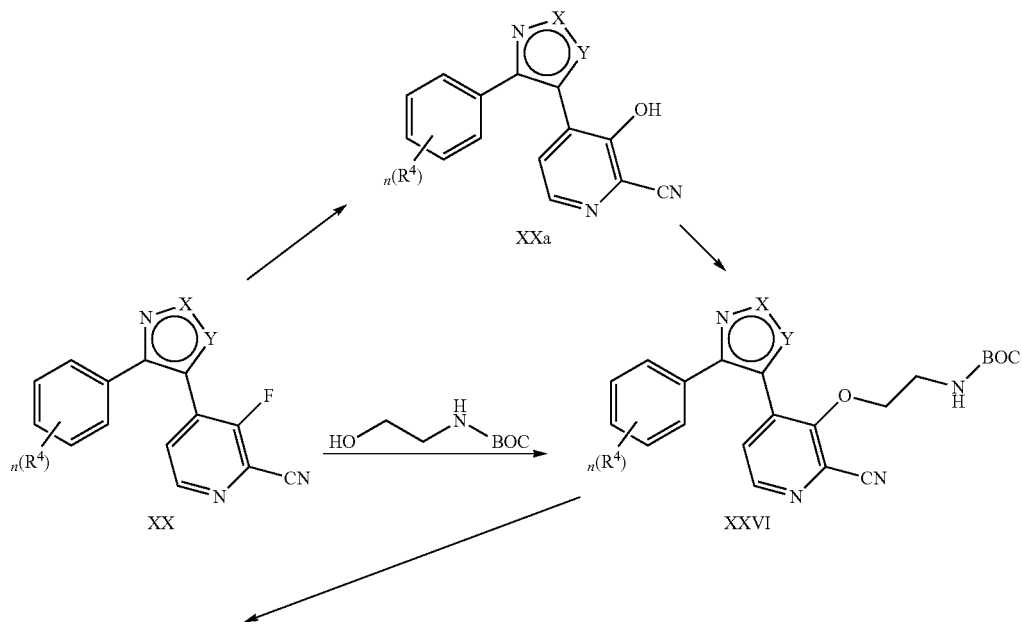

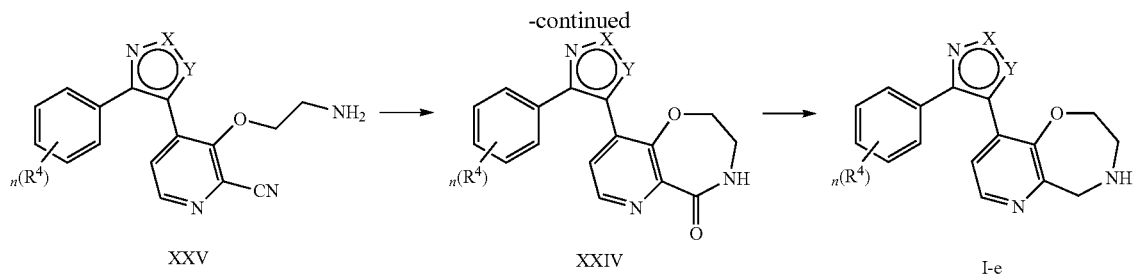

Oxazepine of Formula I-e is prepared as shown in Scheme 5. Fluorocyano compound XX is treated with the anion of N-Boc ethanolamine generated with lithium or sodium hexamethyldisilazide or preferably sodium hydride in a non-nucleophilic, non-reactive solvent such as THF or dioxane at temperatures ranging from 0° C. to 50° C. where 10° C. to 25° C. is preferred, to afford ether XXVI. Compound of formula XXVI may also be prepared by treatment of compound XX with 2-(methylsulfonyl)ethanol and sodium hydride following the procedure described by Ismail, et al. (Syn. Comm, 34, 751, 2004) to give hydroxyl compound XXa which may then be converted to XXVI under standard coupling reaction conditions well known to one of ordinary skill in the art [Mitsunobu, O., Synthesis, 1-28 (1981]. More specifically, the hydroxyaryl compound of Formula XXa is combined with 1 to 2 equivalents of N-Boc ethanolamine, 1 to 2 equivalents of triphenylphosphine and 1 to 2 equivalents of diisopropyldiazocarbxylate in a suitable organic solvent such as THF. The reaction mixture is stirred at temperatures ranging from 0° C. to rt for 1 to 24 hr. The free amine is prepared by removing the Boc group with TFA/CH$_2$Cl$_2$ or HCl/MeOH to afford the acidic salt of XXV. Treatment of XXV with aqueous sodium or potassium hydroxide at 25° C. to 100° C., where 75° C. to 90° C. is preferred, gives lactam XXIV. Reduction of XXIV to yield oxazepine I-e may be accomplished using hydride reducing agents such as lithium aluminum hydride (LAH) or borane in non-reactive solvents such as THF or by using zinc in acetic acid at 50° C. to reflux, where 100° C. is preferred.

Scheme 6

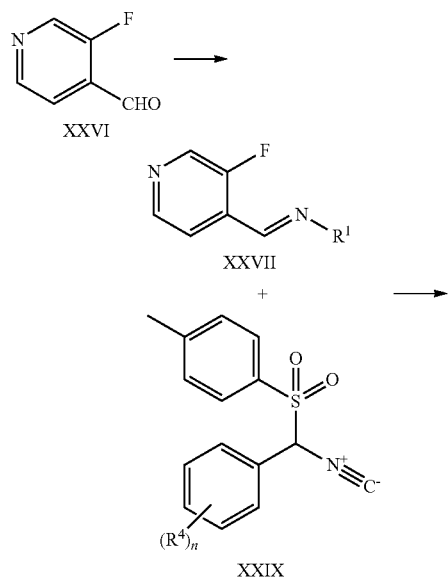

Imidazole of Formula I-f may be prepared as shown in Scheme 6. Imine XXVII may be generated by reaction of aldehyde XXVI and an R$^1$-substituted primary amine in a suitably inert solvent such as diethyl ether or preferably tert-butyl methyl ether at from 0° C. to 50° C., preferably at rt. The toluenesulfonylmethyl isocyanide [tosmic] reagent XXIX is prepared following the two-step general procedure described in the literature (*Organic Syntheses*; Wiley & Sons: New York, 2004; Collect. Vol. 10, p. 692). Imidazole XXVIII is then formed by reacting imine XXVII and tosmic reagent XXIX with a carbonate base such as Na$_2$CO$_3$ or preferably K$_2$CO$_3$ in a suitably polar, inert solvent such as dimethylacetamide, 1-methyl-2-pyrrolidinone (NMP) or preferably DMF at from 0° C. to 50° C., preferably at rt. Intermediate XXVIII may be reacted further to provide compounds of Formula I-f following the general procedures described in Schemes 3-5.

Scheme 7

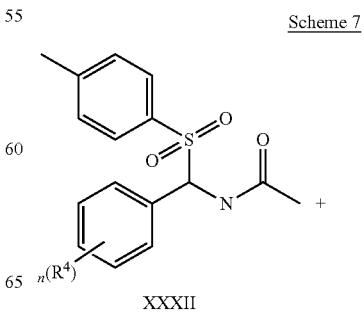

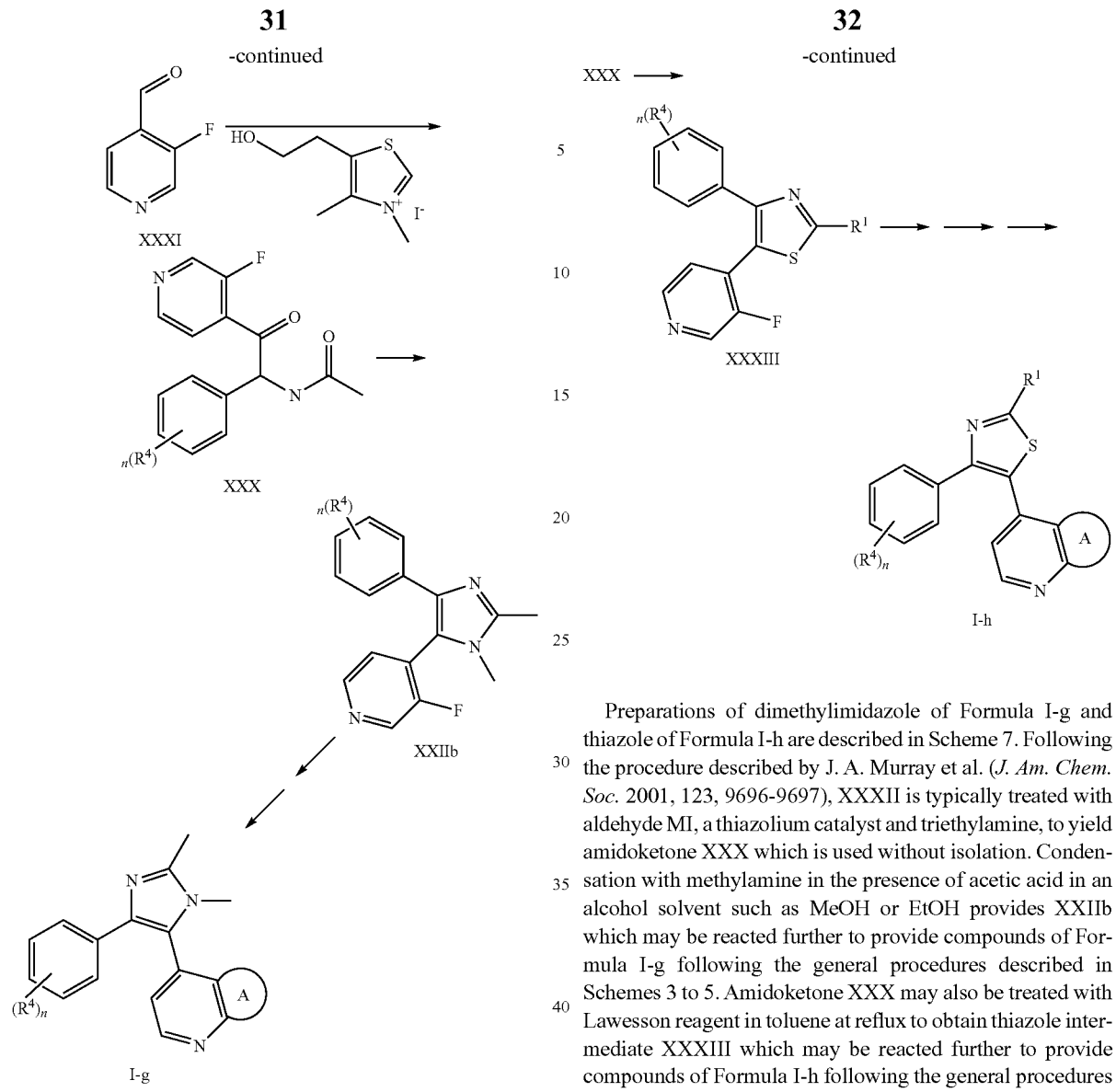

Preparations of dimethylimidazole of Formula I-g and thiazole of Formula I-h are described in Scheme 7. Following the procedure described by J. A. Murray et al. (*J. Am. Chem. Soc.* 2001, 123, 9696-9697), XXXII is typically treated with aldehyde MI, a thiazolium catalyst and triethylamine, to yield amidoketone XXX which is used without isolation. Condensation with methylamine in the presence of acetic acid in an alcohol solvent such as MeOH or EtOH provides XXIIb which may be reacted further to provide compounds of Formula I-g following the general procedures described in Schemes 3 to 5. Amidoketone XXX may also be treated with Lawesson reagent in toluene at reflux to obtain thiazole intermediate XXXIII which may be reacted further to provide compounds of Formula I-h following the general procedures described in Schemes 3 to 5.

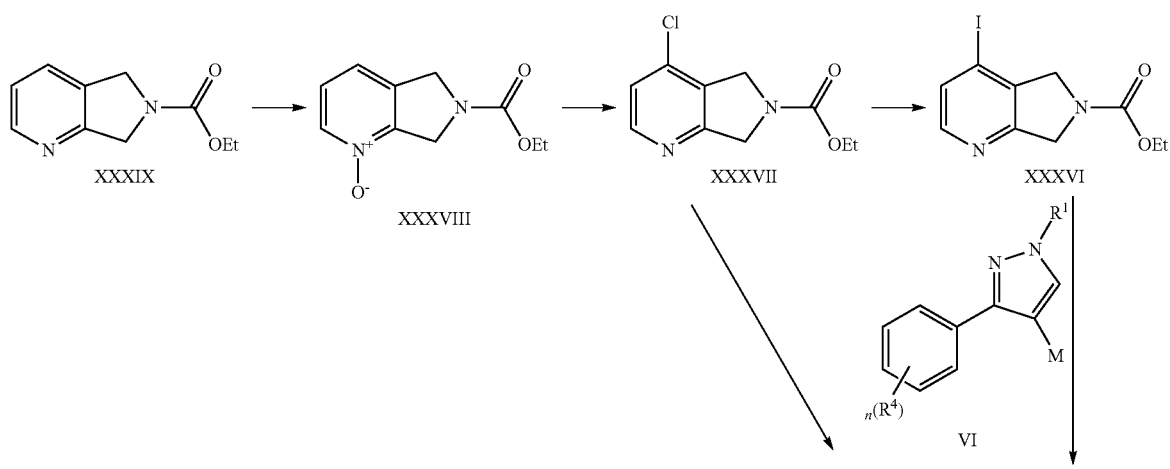

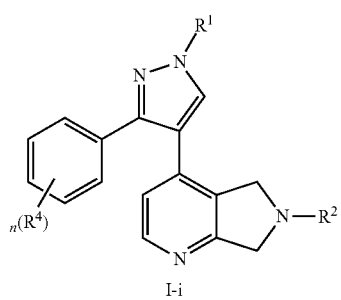

I-i

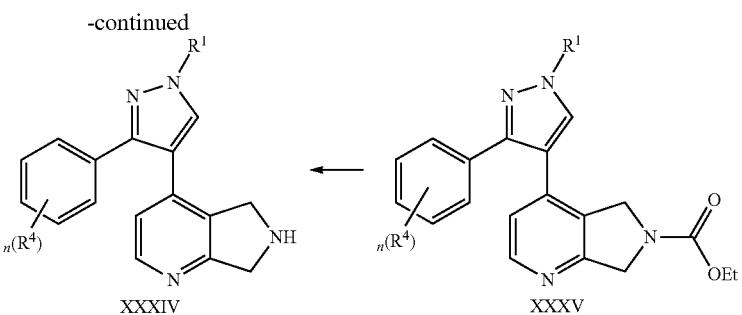

XXXIV        XXXV

Compound of Formula I-i may be prepared as described in Scheme 8. Ethyl 5H-pyrrolo[3,4-b]pyridine-6(7H)-carboxylate XXXIX may be treated with an oxidizing agent such as m-chloroperbenzoic acid or hydrogen peroxide/acetic acid to give N-oxide XXXVIII. Chlorination using phosphorus oxychloride or preferably oxalyl chloride in a suitably polar but inert solvent such as DMF or NMP at temperatures ranging from 0° C. to 50° C. where 0° C. to rt is preferred gives a mixture of 2-chloro and 4-chloro (formula XXXVII) derived products. Intermediate XXXVII may be coupled with metallopyrazole VI following the general procedures described in Scheme 2 to afford compound of formula XXXV. Intermediate XXXVII may also be converted to the corresponding iodide XXXVI by refluxing in acetonitrile with sodium iodide. The iodide XXXVI may also be coupled with metallopyrazole VI following the general procedures described in Scheme 2 to afford compound of formula XXXV. Treatment of carbamate XXXV with aqueous potassium or sodium hydroxide in an alcohol solvent such as EtOH or MeOH at rt to reflux, where reflux is preferred, affords amine XXXIV. This material may be converted into N-alkyl amines, amides and sulfonamides of compounds of Formula I-i. For example, compounds of Formula I-i where $R^2$ is a substituted carbonyl (amide), may be prepared by coupling of substituted carboxylic acids with XXXIV using amide coupling agents where propylphosphonic anhydride (T3P) with triethylamine is preferred in solvents such as THF or ethyl acetate (EtOAc). Likewise compounds of Formula I-i where $R^2$ is a substituted sulfonyl (sulfonamide) may be prepared by treating compound XXXIV with substituted sulfonyl chlorides in non-reactive solvents such as THF or $CH_2Cl_2$ in the presence of a non-nucleophilic base such as diisopropylethylamine or triethylamine.

Scheme 9

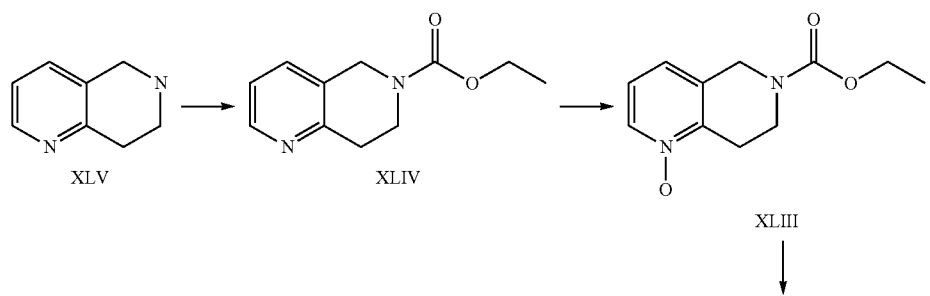

XLV       XLIV       XLIII

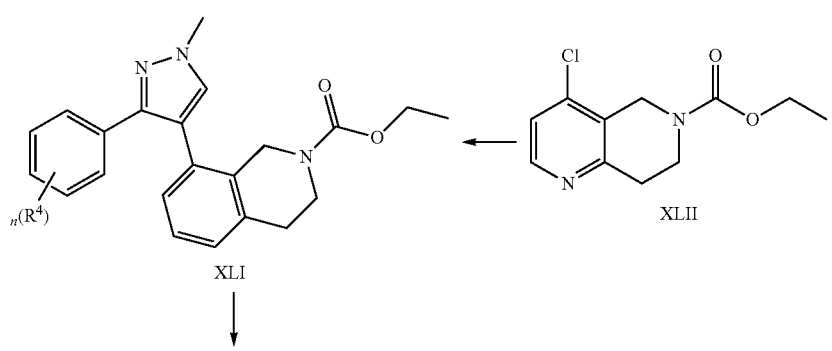

XLI       XLII

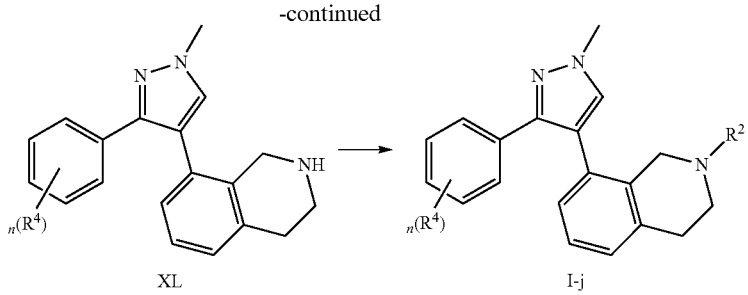

XL → I-j

Compound of Formula I-j may be prepared as shown in Scheme 9. 5,6,7,8-Tetrahydro-1,6-naphthyridine XLV is converted to ethyl carbamate XLIV using ethyl chloroformate and a non-nucleophilic base such as triethylamine in THF or $CH_2Cl_2$. This intermediate may be converted into compound of Formula I-j following the general procedures used to prepare compound I-i as described in Scheme 8.

Scheme 10

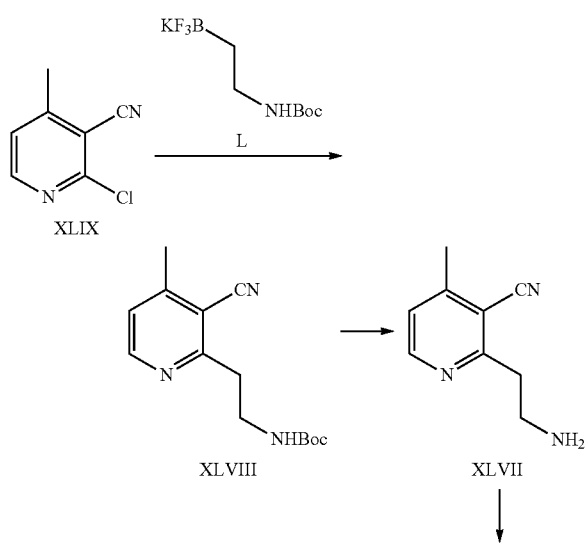

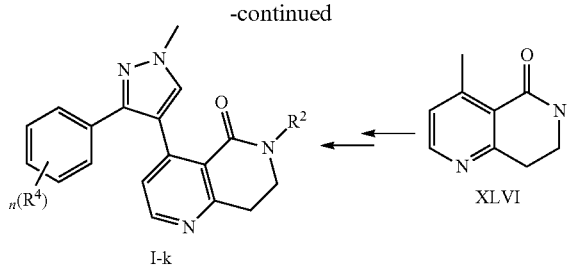

I-k     XLVI

Lactam of Formula I-k is prepared as described in Scheme 10. Chlorocyanopicoline XLIX is treated with 1 to 2 equivalents of potassium trifluoroborate salt L in the presence of 2 to 5 equivalents of $Cs_2CO_3$ and a catalytic amount (0.01 to 0.10 equivalents) of $Pd(dppf)Cl_2$ in a mixture of toluene and water at temperatures from about 75° C. to about 125° C. in a sealed tube or by microwave heating to give compound XLVIII. Removal of the Boc protecting group with TFA, neat or in $CH_2Cl_2$ solution, or with HCl in MeOH or EtOH provides compound XLVII which may then be cyclized to form lactam XLVI by heating in aqueous NaOH from 50° C. to 100° C. Compound XLVI may be converted into compound of Formula I-k following the general procedures detailed in Scheme 1 that were used to prepare compound of Formula I.

Scheme 11

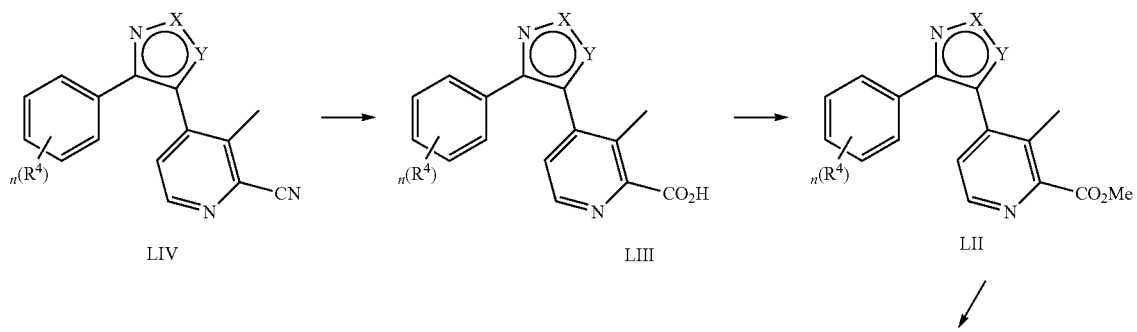

LIV → LIII → LII

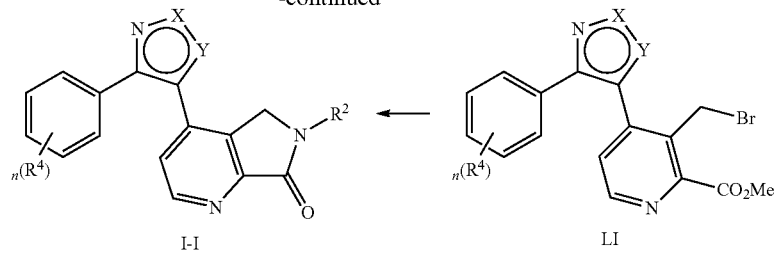

5H-Pyrrolo[3,4-b]pyridin-7(6H)-one of Formula I-l may be prepared as shown in Scheme 11. 2-Cyano-3-methylpyridine of formula LIV (prepared following the general procedures in Scheme 2) is hydrolyzed using aqueous sodium or potassium hydroxide with a MeOH or EtOH as co-solvent at elevated temperatures to afford acid of formula LII. Esterification with MeOH in the presence of a catalytic amount of sulfuric acid at from 50° C. to 100° C. yields compound LII.

This material may be brominated with N-bromosuccinimide in carbon tetrachloride or $CH_2Cl_2$ with a catalytic amount of radical initiator such as benzoyl peroxide or 2'2'-azobis (2-methylpropionitrile) (AIBN) at from 50° C. to 85° C. to give compound LI. Compound I-I may be formed by treating LI with $R^5$-substituted primary amine in a non-reactive polar solvent such as THF or acetonitrile with a non-nucleophilic base such as potassium or sodium carbonate, or preferably diisopropylethyl amine or triethylamine at temperatures from 0° C. to 50° C. where rt is preferred.

Scheme 12

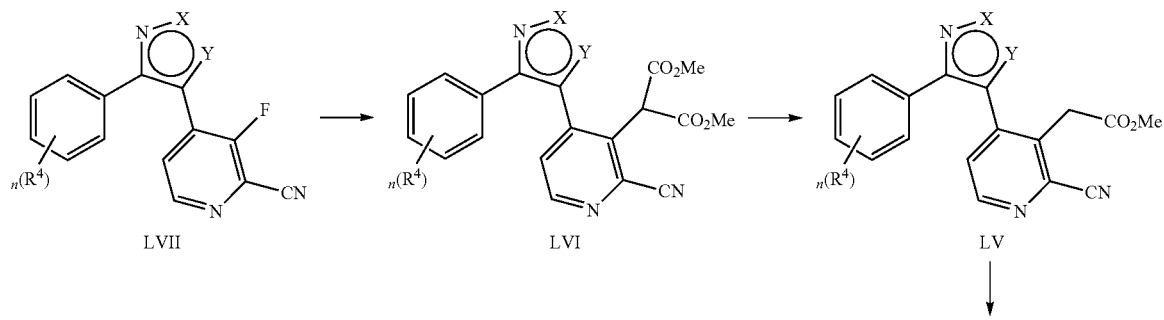

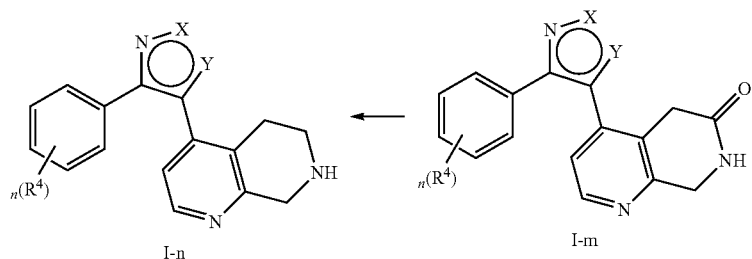

7,8-Dihydro-1,7-naphthyridin-6(5H)-one of Formula I-m and 5,6,7,8-tetrahydro-1,7-naphthyridine of Formula I-n are synthesized as shown in Scheme 12. Compound LVII is reacted with 1 to 1.5 equivalents of sodium dimethylmalonate in a polar solvent such as NMP or DMF at from 50° C. to 110° C. to give diester of formula LVI. Decarboxylation of this material is accomplished by heating between 50° C. and 100° C. with 1 to 1.5 equivalents of lithium chloride in DMSO and 2 equivalents of water to give ester LV. Hydrogenolysis of LV in acetic acid with palladium on activated carbon gives lactam I-m which may be converted to compound of Formula I-n by treatment with hydride reducing agents such as borane-THF complex or lithium aluminum hydride in THF at from rt to reflux.

Scheme 14

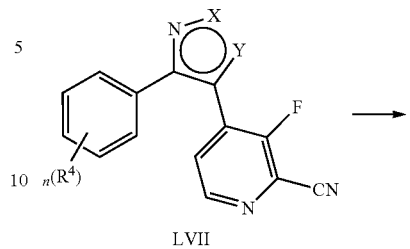

LVII

Scheme 13

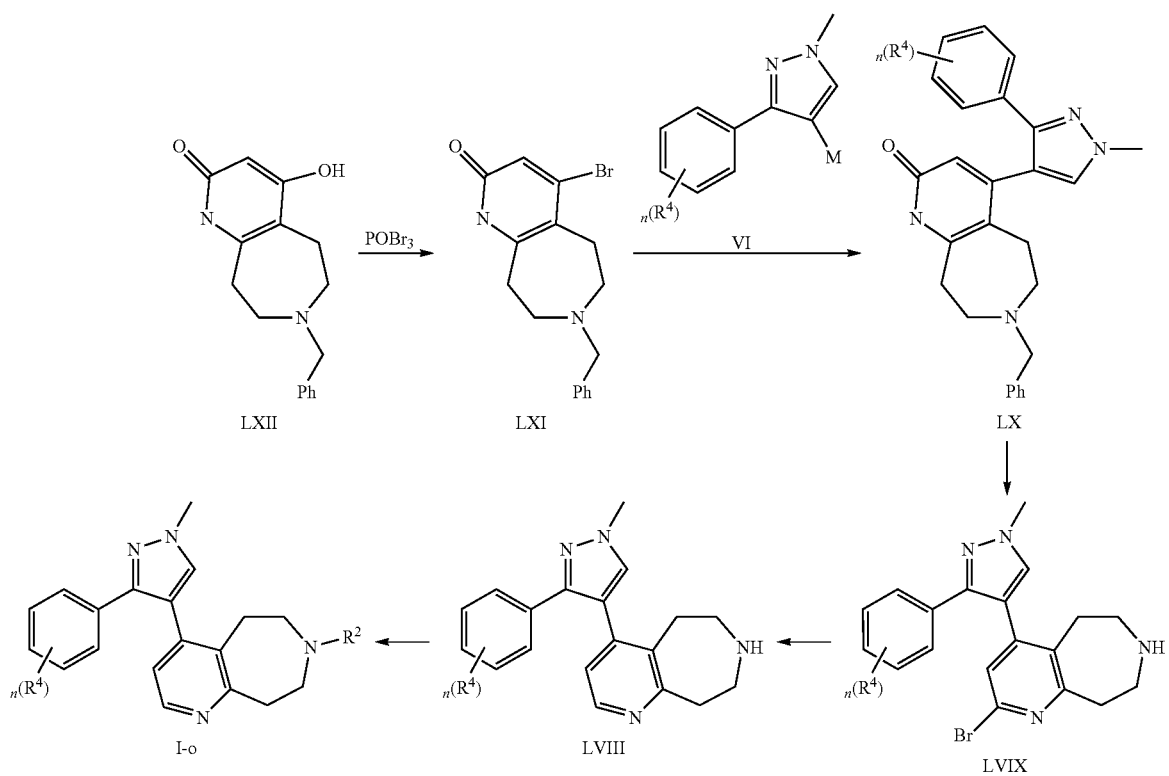

6,7,8,9-Tetrahydro-5H-pyrido[2,3-d]azepine of Formula I-o is prepared as shown in Scheme 13. Compound LXII (prepared following general procedures described in WO 2007140213 substituting N-benzyl-4-piperidone for N-Boc-4-piperidone) is treated with a brominating agent such as phosphorus tribromide or phosphorus oxybromide neat or in a suitably non-reactive solvent such as CH$_2$Cl$_2$ to yield compound LXI. Compound LX may be prepared with bromide LXI and pinacol borane of formula VI following the general procedures shown in Scheme 2. Conversion of LX to bromopyridine LVIX may be accomplished by reaction with a brominating agent such as phosphorus tribromide or phosphorus oxybromide neat or in a suitably non-reactive solvent such as CH$_2$Cl$_2$. Hydrodehalogenation to form compound of formula LVIII is performed by hydrogenation with Raney nickel or palladium on carbon and this material may be further derivatized to give compound of Formula I-o in similar fashion as described in Scheme 8 for the synthesis of compound I-i.

-continued

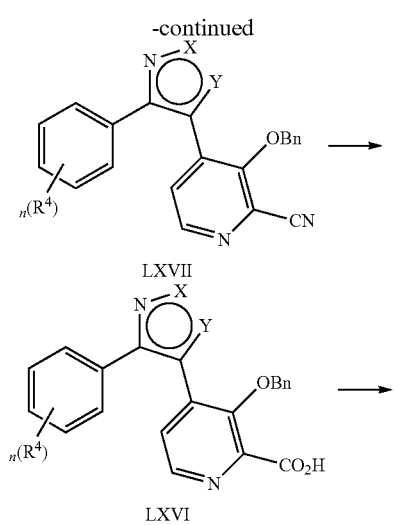

LXVII

LXVI

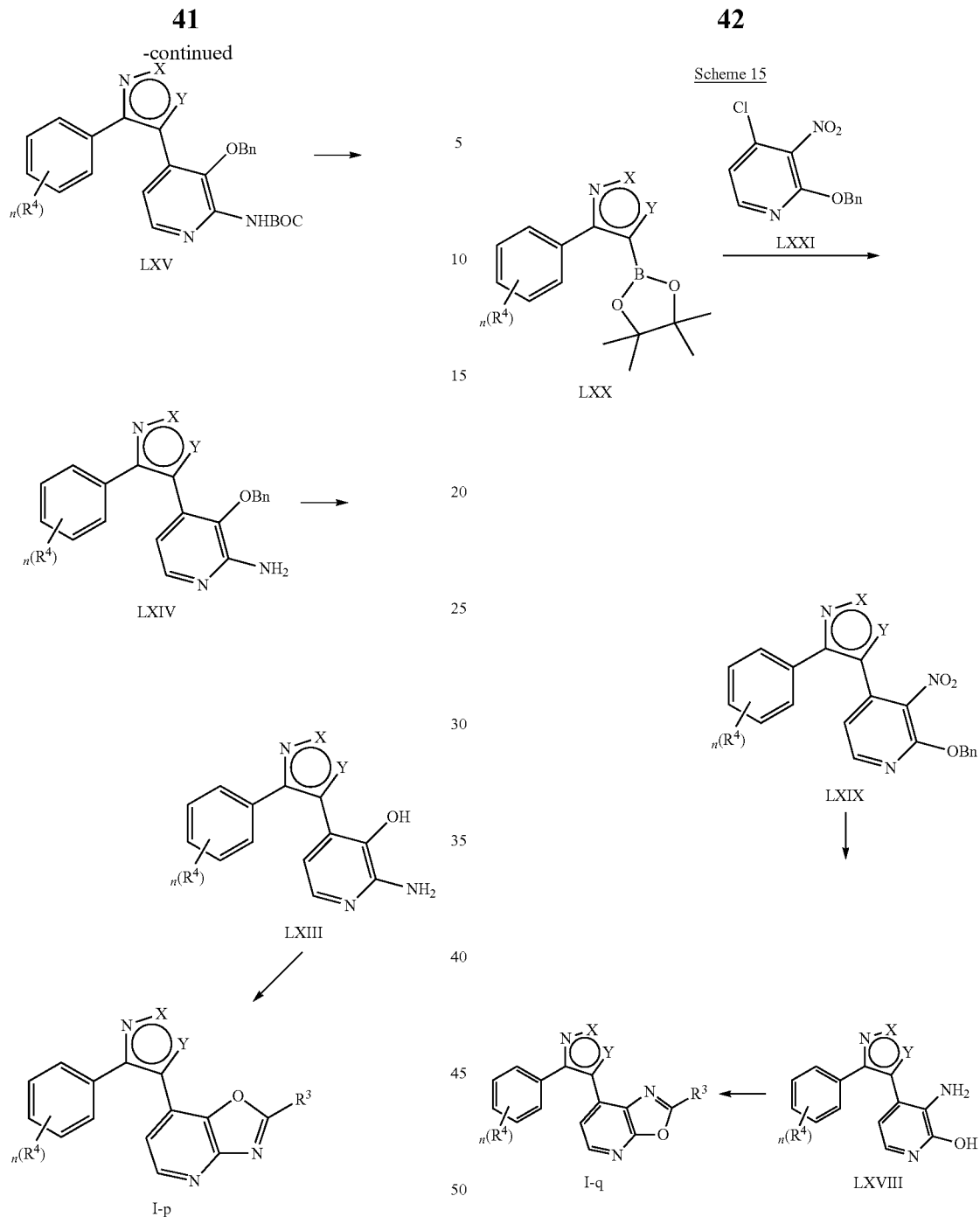

Oxazolo[4,5-b]pyridine of Formula I-p is prepared as shown in Scheme 14. Thus treatment of fluoronitrile compound LVII with sodium benzylate under standard conditions will yield the benzylether LXVII. Hydrolysis of the nitrile to the corresponding acid LXVI may be done using an aqueous solution of inorganic base such as KOH with a suitable solvent such as MeOH or EtOH. Subsequent Curtius rearrangement using diphenylphosphoryl azide in t-butanol affords BOC protected amine LXV. Treatment of LXV with an acid such as HCl or TFA will yield LXIV. Cleavage of the benzylether via hydrogenolysis in the presence of a catalyst like palladium on carbon will yield hydroxy intermediate LXIII. Finally, treatment of LXIII with an appropriately $R^3$ substituted orthoformate as solvent in the presence of an acid such as toluene sulfonic acid will yield the desired target I-p.

The regioisomeric oxazole I-q can be prepared as described in Scheme 15. Suzuki coupling of known chloropyridine LXXI (Bioorg. Med. Chem. Lett. 125 (2003)) with a boronate of type LXX (prepared following the general methods shown in Scheme 2) in the presence of a Pd(0) catalyst such as palladiumtetrakistriphenylphosphine(0) and a base such as potassium fluoride in a solvent such as MeOH at temperatures ranging from rt to 100° C., preferably at reflux, will yield nitro derivative LXIX. Conversion of LXIX to the aminoalcohol LXVIII can be accomplished via hydrogenation in the presence of a suitable catalyst such as Pd on carbon or palladium hydroxide in solvents such as MeOH or EtOH. Finally condensation of LXVII with an appropriately $R^3$ substituted orthoformate as solvent in the presence of an acid such as toluene sulfonic acid will yield the desired target oxazolo[5,4-b]pyridine I-q.

Scheme 16

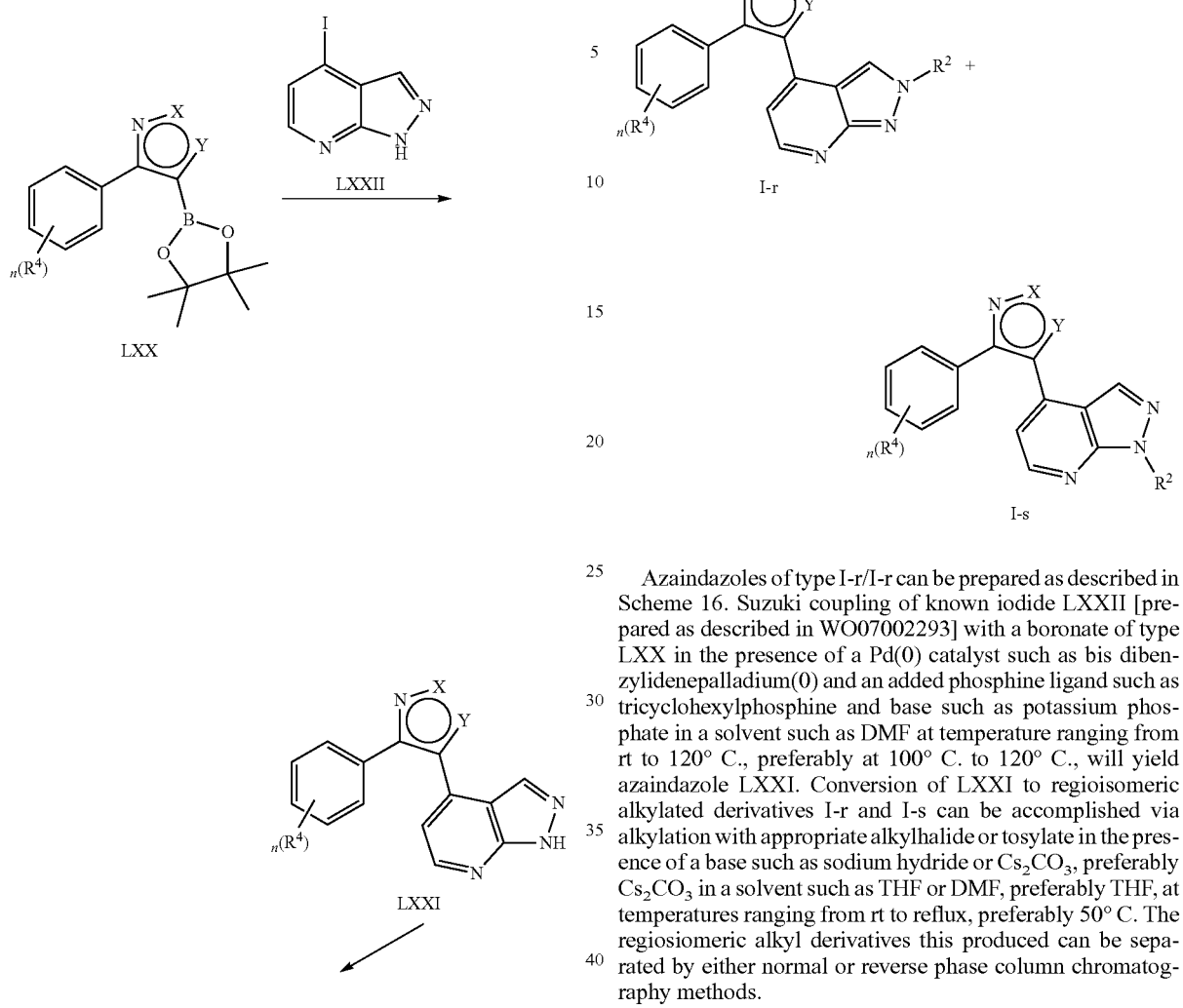

Azaindazoles of type I-r/I-r can be prepared as described in Scheme 16. Suzuki coupling of known iodide LXXII [prepared as described in WO07002293] with a boronate of type LXX in the presence of a Pd(0) catalyst such as bis dibenzylidenepalladium(0) and an added phosphine ligand such as tricyclohexylphosphine and base such as potassium phosphate in a solvent such as DMF at temperature ranging from rt to 120° C., preferably at 100° C. to 120° C., will yield azaindazole LXXI. Conversion of LXXI to regioisomeric alkylated derivatives I-r and I-s can be accomplished via alkylation with appropriate alkylhalide or tosylate in the presence of a base such as sodium hydride or $Cs_2CO_3$, preferably $Cs_2CO_3$ in a solvent such as THF or DMF, preferably THF, at temperatures ranging from rt to reflux, preferably 50° C. The regiosiomeric alkyl derivatives this produced can be separated by either normal or reverse phase column chromatography methods.

Scheme 17

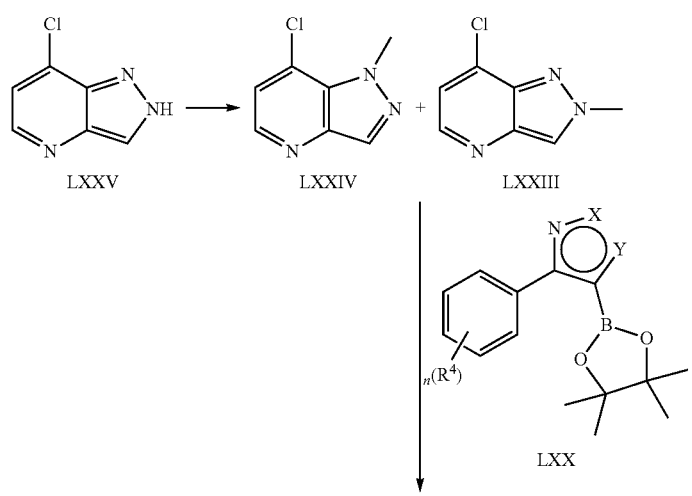

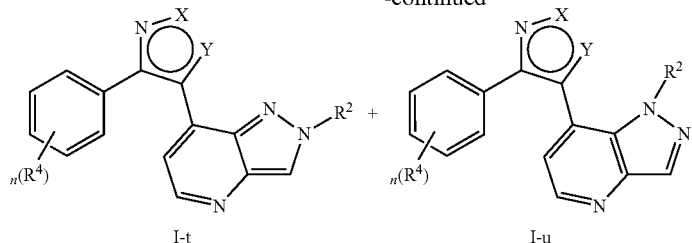

I-t                I-u

Compounds of Formula I-t/I-u can be prepared as described in Scheme 17. Alkylation of the known chloroindazole LXXV (prepared as in EP151962) with appropriate alkylhalide or tosylate in the presence of a base such as sodium hydride or $Cs_2CO_3$, preferably $Cs_2CO_3$ in a solvent such as THF or DMF, preferably THF, at temperatures ranging from rt to reflux, preferably 50° C., will yield regiosiomeric alkyl derivatives LXXIII and LXXIV which can be separated by either normal or reverse phase column chromatography methods. Suzuki coupling of LXXIII and LXXIV with boronates of type LXX in the presence of a Pd(0) catalyst such as bis dibenzylidenepalladium(0) and an added phosphine ligand such as tricyclohexylphosphine and base such as potassium phosphate in a solvent such as DMF at temperature ranging from rt to 120° C., preferably at 100° C. to 120° C., will yield compounds of Formula I-t/I-u.

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. Coupling constants (J values) are reported in Hertz.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate $R_f$'s or retention times (RetT).

EXAMPLES

Example 1

4-(3-(4-fluorophenyl)-1-methyl-1H-pyrazol-4-yl)furo[3,4-b]pyridin-5(7H)-one

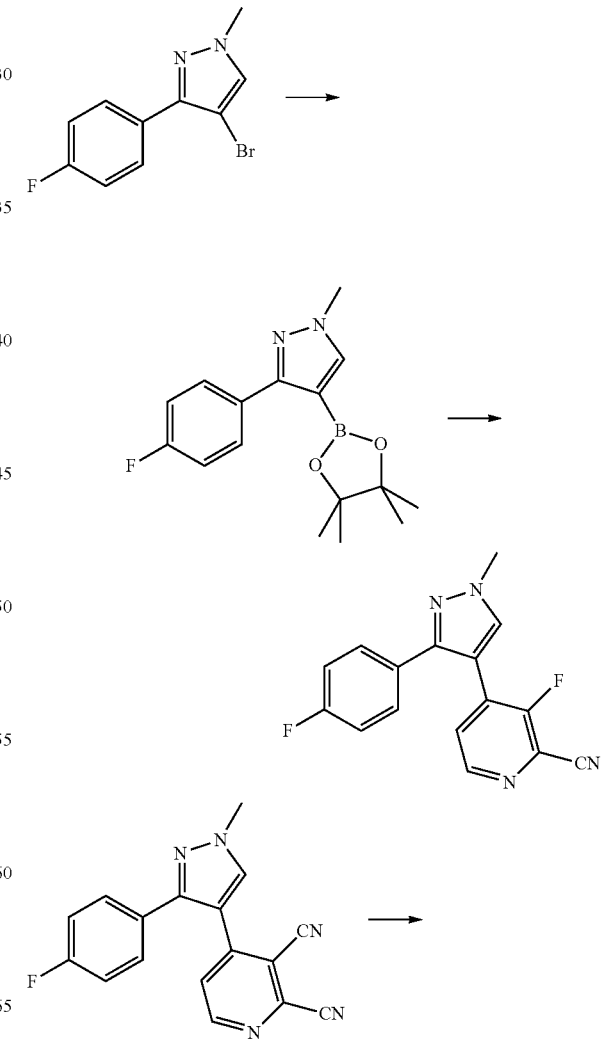

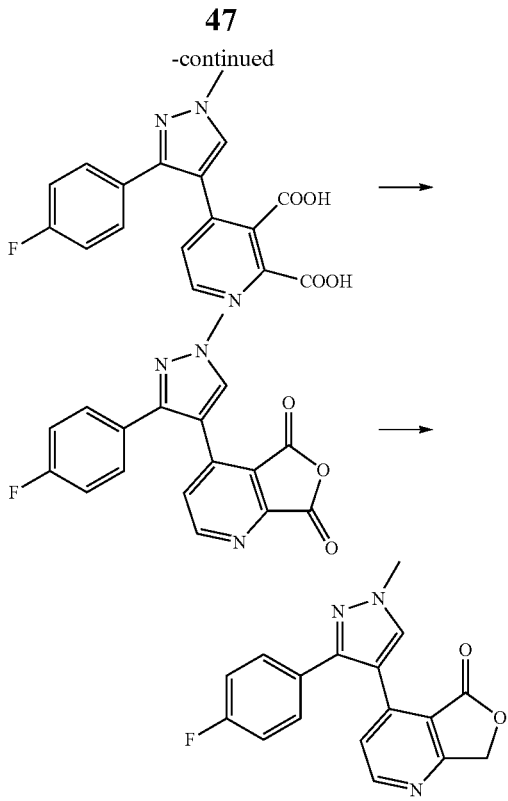

Step 1: Preparation of 3-(4-fluorophenyl)-1-methyl-4-(4,4,5,5-tetramethyl-1,3,2-dioxaborolan-2-yl)-1H-pyrazole A solution of 4-bromo-3-(4-fluorophenyl)-1-methyl-1H-pyrazole (700 g, 2.74 mol) in THF (1.4 L) was cooled to 15° C. and isopropylmagnesium chloride lithium chloride complex (1.3M in THF, 3.8 L, 4.94 mol) was added slowly while maintaining the reaction temperature below 25° C. The mixture was stirred for 3 hr at 20° C. and a 10° C. solution of 2-isopropoxy-4,4,5,5-tetramethyl-1,3,2-dioxaborolane (610 g, 3.28 mol) in THF (1.4 L) was added dropwise while maintaining an internal temperature below 20° C. The resulting green/brown hazy solution as stirred for 1 hr between 10° C. and 20° C. after which time it was cooled to 10° C. Water (5.6 L) cooled to 10° C. was added slowly to the reaction mixture so that the reaction temperature stayed below 25° C. Celite (1.4 kg) was added followed by 2-methyltetrahydrofuran (7 L) and the mixture was stirred for 15 min at 20° C. The mixture was filtered through Celite and the filter pad was rinsed with 2-methyltetrahydrofuran (8 L). The organic phase was separated and washed with brine (5.6 L) then concentrated under vacuum to a low stir volume. The material was diluted with EtOH (3 L) and reconcentrated. This material was re-dissolved in EtOH (3.5 L) and water (4.2 L) was added over 30 min with strong stirring. The resulting slurry was stirred at 15° C. for 1 hr, filtered and washed with 4 volumes of water. The resulting cake was blown dry then further dried in a vacuum oven at 40° C. to yield 0.4 kg (48%) of Ex 1-Step 1 product as a white solid: APCI MS m/z 303.2 (M+1); $^1$H NMR (400 MHz, CDCl$_3$) δ 7.91 (dd, J=8.9, 5.6, 2H), 7.70 (s, 1H), 7.03 (dd, J=8.8, 8.8, 2H), 3.90 (s, 3H), 1.29 (s, 12H).

Step 2: Preparation of 3-fluoro-4-(3-(4-fluorophenyl)-1-methyl-1H-pyrazol-4-yl)picolinonitrile Ex 1-Step 1 product (14.5 g, 48 mmole) and 3-fluoro-4-iodopicolinonitrile (9.92 g, 40.0 mmole) were combined in 100 mL DMF. and treated with Cs$_2$CO$_3$ (19.90 g, 61.2 mmole). The resulting suspension was sparged with nitrogen for 20 min and treated with tris(dibenzylideneacetone)dipalladium(0) (1.51 g, 1.6 mmole) in a single portion. The nitrogen sparging was continued for an additional 20 min, and stirring of the dark suspension was continued for 30 min at rt. The reaction was warmed to 50° C. for 6 hr and was allowed to cool to rt overnight. The thick slurry was added to 150 mL EtOAc, the suspension was diluted with 50 mL 50% saturated aqueous sodium chloride, then treated with DARCO, and stirred 1 hr at rt. The mixture was filtered through celite, the layers were separated, and the organic layer was washed with 3×30 mL 50% saturated aqueous NaCl. The organic layer was dried over anhydrous MgSO$_4$ and was concentrated in vacuo to give 18 g of a pasty orange solid. The solid was dissolved in a minimum amount of CH$_2$Cl$_2$ loaded onto a 100 g SNAP cartridge, and the crude material was eluted over a 340 g SNAP cartridge with a 5-80% EtOAc/heptane gradient over 4.8 L. The appropriate fractions were combined and concentrated. During concentration, a white solid precipitated. This was collected to give 6.93 g (59%) of Ex 1-Step 2 product as a white solid: APCI MS m/z 297.0 (M+1); $^1$H NMR (400 MHz, CDCl$_3$) δ 8.28 (d, J=5.1, 1H), 7.84 (d, J=2.9, 1H), 7.40 (dd, J=5.3, 2.2, 2H), 7.25 (dd, J=5.8, 4.9, 1H), 7.09 (dd, J=8.6, 8.6, 2H), 4.02 (s, 3H).

Step 3: Preparation of 4-(3-(4-fluorophenyl)-1-methyl-1H-pyrazol-4-yl)pyridine-2,3-dicarbonitrile Dissolved Ex 1-Step 2 product (10.00 g, 33.75 mmol) in DMSO (100 mL) with gentle heating. Added potassium cyanide (2.35 g, 35.0 mmol) and heated to 50° C. and stirred. After 2 hr, cooled in an ice bath and added 0.1N aqueous NaOH (50 mL). The resulting slurry was stirred for 5 min, solids were collected, rinsed with water and air dried to yield 10.34 g of Ex 1-Step 3 product as a light cream colored solid: $^1$H NMR (400 MHz, CDCl$_3$) δ 8.56 (d, J=5.2, 1H), 8.02 (s, 1H), 7.33 (dd, J=8.9, 5.2, 2H), 7.24 (d, J=5.5, 1H), 7.06 (dd, J=8.6, 8.6, 2H), 4.02 (s, 3H).

Step 4: Preparation of 4-(3-(4-fluorophenyl)-1-methyl-1H-pyrazol-4-yl)pyridine-2,3-dicarboxylic acid, as a dipotassium salt Heated a mixture of Ex 1-Step 3 product (10.34 g, 34.1 mmol) and aqueous KOH (28.3 g, 504 mmol, dissolved in 100 mL water) at 100° C. for 24 hr. The mixture was cooled in ice to precipitate a thick white solid. The material was warmed back to rt, filtered and air dried to yield 12.47 g (88%) of Ex 1-Step 4 product as a cream colored solid: LCMS m/z 342.1 (M+1).

Step 5: Preparation of 4-[3-(4-fluorophenyl)-1-methyl-1H-pyrazol-4-yl]furo[3,4-b]pyridin-5(7H)-one, as a monohydrochloride Ex 1-Step 4 Product (5.00 g, 12.0 mmol) was slurried with acetic acid (35 mL) and acetic anhydride (12.5 mL) and heated to 110° C. for 3 hrs. The resulting homogeneous mixture was cooled and concentrated, slurried with 50 mL diethyl ether and re-concentrated to yield 4-(3-(4-fluorophenyl)-1-methyl-1H-pyrazol-4-yl)-6-methyl-5H-pyrrolo[3,4-b]pyridine-5,7(6H)-dione as a sticky yellow solid. This material was slurried in THF (70 mL), sodium borohydride (568 mg, 15.0 mmol) was added and acetic acid (1.7 mL, 2.5 mmol) was added dropwise over one minute. After stirring for 90 min, the reaction was concentrated to a thick yellow paste, acetic acid (90 mL) and acetic anhydride (45 mL) were added and the mixture was heated at 110° C. for two hr to give a homogeneous solution. The heat was removed and the mixture was stirred overnight at rt and concentrated. The residue was partitioned between EtOAc and water, the organics were separated organics, and the aqueous phase was re-extracted with EtOAc. The combined extracts were washed with brine, dried (MgSO₄) and concentrated to a thick yellow oil. Purification by silica gel chromatography eluting with 50% EtOAc/heptanes yielded 2.06 g (55%) of Ex 1-Step 5 product as a waxy white solid. This material was dissolved in EtOAc (100 mL) and treated with 1.2 equivalents of 2 N HCl/diethylether to yield 1.91 g of Ex 1-Step 5 product as a yellow solid: MS (APCI) 310.0 m/z (M+1); $^1$H NMR (400 MHz, DMSO-d₆) δ 8.64 (d, J=5.3, 1H), 8.17 (s, 1H), 7.32 (dd, J=8.8, 5.5, 2H), 7.11 (dd, J=9.0, 9.0, 2H), 7.08 (d, J=5.0, 1H), 5.32 (s, 2H), 3.92 (s, 3H).

3-Fluoro-4-(3-(4-fluorophenyl)-1-methyl-1H-pyrazol-4-yl)picolinonitrile (see step 2) was also prepared via the following route:

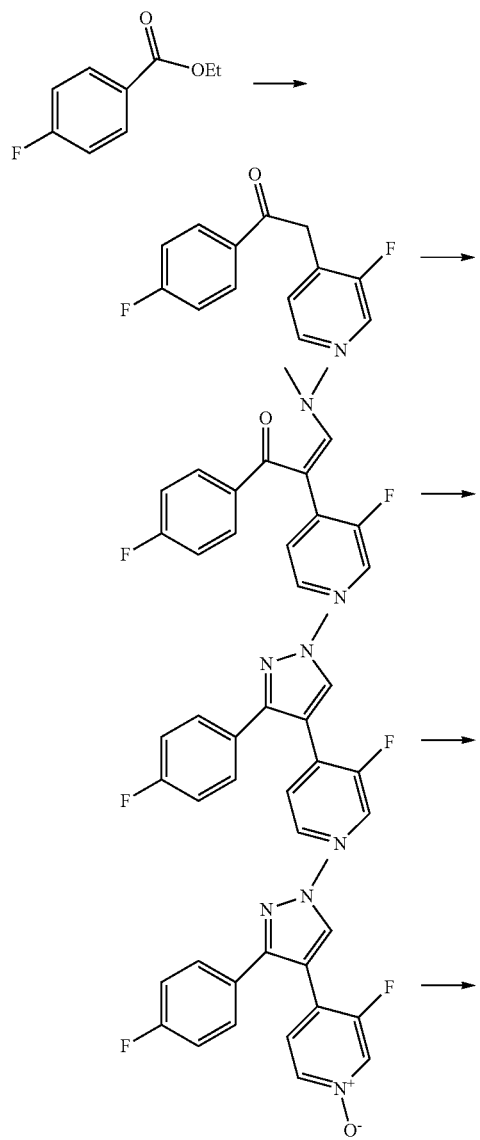

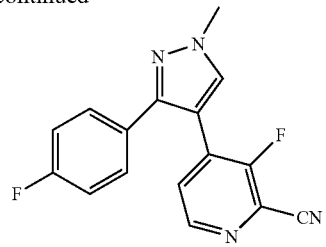

Step 6: Preparation of 1-(4-fluorophenyl)-2-(3-fluoropyridin-4-yl)ethanone

Lithium hexamethyldisilazide (1.0M in THF, 17.9 mL, 17.9 mmol) was cooled to 0° C. and 3-fluoro-4-methylpyridine (1.00 g, 0.926 mmol) in THF (50 mL) was added dropwise, keeping the solution temperature below 5° C. The mixture was then stirred for 1 hour at 0° C. and ethyl 4-fluorobenzoate in THF (50 mL) was added dropwise. The reaction was allowed to warm slowly to rt with stirring overnight. Aqueous ammonium chloride was added and the mixture was poured into EtOAc. The organic phase was separated dried (Na₂SO₄) and concentrated. Silica gel chromatography using a 10-50% EtOAc/heptanes gradient yielded 1.83 g (89%) of Ex 1-Step 6 product as a white solid: LCMS m/z 234.4 (M+1); $^1$H NMR (400 MHz, MeOH-d₄) δ 8.41 (d, J=1.7 1H), 8.32 (d, J=4.8, 1H), 8.14 (dd, J=8.9, 5.4, 2H), 7.38 (dd, J=5.9, 5.1, 1H), 7.25 (dd, J=9.0, 9.0, 2H), 4.52 (s, 2H).

Step 7: Preparation of 3-(dimethylamino)-1-(4-fluorophenyl)-2-(3-fluoropyridin-4-yl)prop-2-en-1-one Ex 1-Step 6 product (1.35 g, 5.79 mmol), dimethylformamide dimethylacetal (0.77 g, 5.79 mmol) and THF (20 mL) were stirred at 80° C. for 2 hr then at 100° C. for one hour and then concentrated to yield 1.6 g of Ex 1-Step 7 product as a yellow oil which was used without purification: LCMS m/z 289.4 (M+1).

Step 8: Preparation of 3-fluoro-4-(3-(4-fluorophenyl)-1-methyl-1H-pyrazol-4-yl)pyridine Ex 1-Step 7 product (1.6 g, 5.55 mmol) was dissolved in EtOH (75 mL) and cooled to 0° C. Methyl hydrazine (0.35 mL, 6.66 mmol) was added dropwise and the mixture was slowly warmed to rt with stirring overnight and then concentrated. LCMS of the crude product showed a mixture of two N-methylpyrazole regiosomers which were separated by silica gel chromatography using a 1:1 mixture of heptanes and 7:2:1 heptane:diethylamine:MeOH for elution. Ex 1-Step 8 product was isolated as a light yellow solid (900 mg, 60%): LCMS m/z 272.5 (M+1); $^1$H NMR (400 MHz, MeOH-d₄) δ 8.41 (d, J=2.5, 1H), 8.20 (d, J=5.1, 1H), 8.01 (d, J=1.7, 1H), 7.39 (dd, J=8.8, 5.3, (2H), 7.19 (dd, J=6.7, 5.1, 1H), 7.09 (dd, J=8.8, 8.8, 2H), 3.98 (s, 3H).

Step 9: Preparation of 3-fluoro-4-(3-(4-fluorophenyl)-1-methyl-1H-pyrazol-4-yl)pyridine 1-oxide Ex 1-Step 8 product (900 mg, 3.32 mmol) was dissolved in CH₂Cl₂ (20 mL) and treated with m-chloroperbenzoic acid (85%, 1.35 g, 6.64 mmol) and stirred at rt for 5 hr. The mixture was concentrated and purified by silica gel chromatography.

The column was flushed with $CH_2Cl_2$ then 0-50% EtOAc/$CH_2Cl_2$ and finally EtOAc, then the desired N-oxide was removed using 20% MeOH/EtOAc with 1% triethylamine. The desired N-oxide was obtained as a yellow oil (1.06 g, quantitative yield): LCMS m/z 288.5 (M+1); $^1$H NMR (400 MHz, MeOH-$d_4$) δ 8.42 (dd, J=5.4, 1.7, 1H), 8.04-8.06 (ddd, J=6.7, 1.8, 0.8, 1H), 8.02 (d, J=2.1, 1H), 7.42 (dd, J=8.8, 5.3, 2H), 7.24 (dd, J=8.7, 6.8, 1H), 7.12 (dd, J=8.7, 8.7, 2H), 3.97 (s, 3H).

Step 10: Preparation of 3-Fluoro-4-(3-(4-fluorophenyl)-1-methyl-1H-pyrazol-4-yl)picolinonitrile Ex 1-Step 9 product (1.06 g, 3.69 mmol), triethylamine (1.03 mL, 7.38 mmol) and trimethylsilyl cyanide (0.615 mL, 4.61 mmol) were stirred in acetonitrile (10 mL) at 70° C. for 3 days. LCMS indicated N-oxide was still present, so an additional 1.5 mL of trimethylsilyl cyanide and 2.5 mL triethylamine were added and the heating was continued for another 24 hr. The mixture was cooled, concentrated and purified by silica gel chromatography using 10-100% EtOAc/heptanes with 1% triethylamine modifier to yield 600 mg (55%) of Ex 1-Step 10 as a yellow solid. Spectral data are consistent with that of the material prepared using the procedure in step 2 above.

Example 2

4-[3-(4-fluorophenyl)-1-methyl-1H-pyrazol-4-yl]-6-methyl-6,7-dihydro-5H-pyrrolo[3,4-b]pyridin-5-one

Step 1: Preparation of 4-(3-(4-fluorophenyl)-1-methyl-1H-pyrazol-4-yl)-6-methyl-5H-pyrrolo[3,4-b]pyridine-5,7(6H)-dione

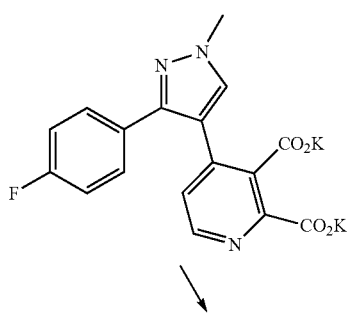

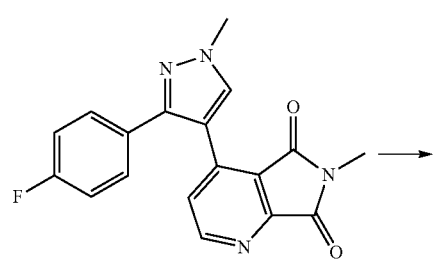

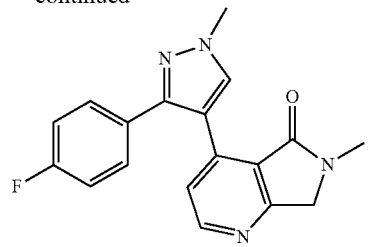

A mixture of Ex 1-Step 4 product (275.29 g, 659.41 mmoles), acetic acid (2.06 L) and acetic anhydride (137.65 mL, 1456 mmol) were heated at 110° C. for 1 hr, cooled to 80° C. and then methylamine (2.0M/THF, 659.41 mL; 567.09 g) was added over 20 min, maintaining the temperature at 80° C. A white smoke was observed during the addition. The reaction was heated to 100° C. overnight and concentrated to approximately 500 mL giving a clear yellow solution. Water (200 mL) was added over 10 min with stirring. Acetic acid (about 100 mL) and an additional 200 mL of water were added to aid stirring. The solids were removed by filtration using a Buchner funnel with cloth and washed with 250 mL water. Air dried for 1 hr then dried in a vacuum oven at 60° C. overnight to yield 206.47 g (93.10%) of Ex 2-Step 1 product as a light yellow solid: LCMS m/z 337.1 (M+1); $^1$H NMR (400 MHz, MeOH-$d_4$) δ 8.59 (d, J=5.4, 1H), 8.26 (s, 1H), 7.42 (dd, J=8.8, 5.3, 2H), 7.25 (d, J=5.3, 1H), 7.10 (dd, J=8.9, 8.9, 2H), 4.02 (s, 3H), 3.15 (s, 3H).

Step 2: Preparation of 4-[3-(4-fluorophenyl)-1-methyl-1H-pyrazol-4-yl]-6-methyl-6,7-dihydro-5H-pyrrolo[3,4-b]pyridin-5-one To a flask equipped with overhead stirring was added Ex 2-Step 1 product (202.00 g, 600.61 mmoles) and zinc dust (<10 micron) (357.04 g, 5.41 moles) followed by acetic acid (2.02 L). The mixture was heated to 105° C. and stirred for 4.5 hr, then cooled to rt. Celite was added to the reaction mixture, and this was filtered to remove the zinc The filter pad was rinsed with EtOAc and the filtrate was concentrated to ~300 mL and 200 mL of water was added. The resulting solid was collected, rinsed with water, and dried under vacuum overnight to give 103.23 g (53%) of Example 2 as a solid: LCMS m/z 323.2 (M+1); $^1$H NMR (400 MHz, CDCl$_3$) δ 8.38 (d, J=5.5, 1H), 8.28 (s, 1H), 7.41 (dd, J=8.8, 5.5, 2H), 7.03 (dd, J=8.6, 8.6, 2H), 6.96 (d, J=5.2, 1H), 4.44 (s, 2H), 4.01 (s, 3H), 3.24 (s, 3H).

Example 3

4-[3-(4-chlorophenyl)-1-methyl-1H-pyrazol-4-yl]-6-methyl-6,7-dihydro-5H-pyrrolo[3,4-b]pyridin-5-one

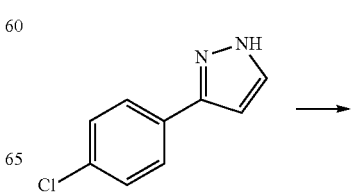

53

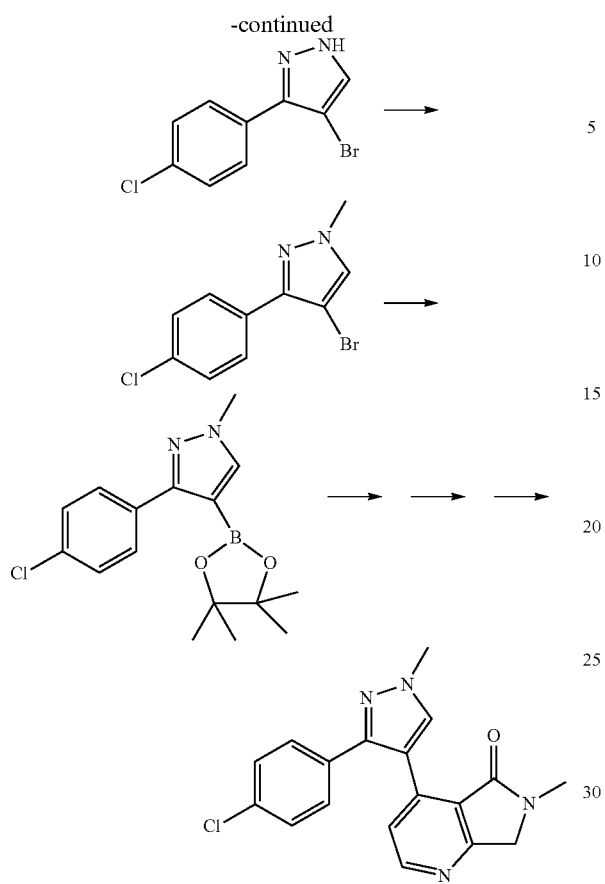

Step 1: Preparation of 4-bromo-3-(4-chlorophenyl)-1H-pyrazole

N-Bromosuccinimide (10.4 g, 56.0 mmol) was added portionwise to a solution of 3-(4-chlorophenyl)-1H-pyrazole (10.0 g, 56.0 mmol) in $CH_2Cl_2$ (140 mL). The mixture was stirred for 10 min, water and an additional portion of $CH_2Cl_2$ were added and the mixture was stirred for 5 min. The organic phase was separated, washed with brine, dried ($MgSO_4$) and concentrated to yield 15.0 g of Ex 3-Step 1 product as a light yellow solid: $^1$H NMR (400 MHz, $CDCl_3$) δ 7.68 (d, J=8.6, 2H), 7.59 (s, 1H), 7.35-7.39 (m, 2H).

Step 2: Preparation of 4-bromo-3-(4-chlorophenyl)-1-methyl-1H-pyrazole $Cs_2CO_3$ (38.0 g, 116.0 mmol) was added to a solution of Ex 3-Step 1 product (15.0 g, 58.0 mmol) in DMF (63 mL). Methyl iodide (3.74 mL, 58.2 mmol) was added and the resulting pink colored solution was stirred at rt for 2 hr. The mixture was concentrated and the residue was partitioned between EtOAc and water. The organic phase was separated and washed with brine, dried ($MgSO_4$) and concentrated. Silica gel chromatography using 40% heptane/$CH_2Cl_2$ yielded 10.1 g (64%) of Ex 3-Step 2 product as a white solid. $^1$H NMR ($CDCl_3$) showed ~5% of the corresponding regioisomer (4-bromo-5-(4-chlorophenyl)-1-methyl-1H-pyrazole). The identities of the two regiosomers were established via NMR NOE (Nuclear Overhauser Effect) experiments. This material was used without further purification. $^1$H NMR (400 MHz, $CDCl_3$) δ 7.80-7.82 (m, 2H), 7.43 (s, 1H), 7.35-7.38 (m, 2H), 3.90 (s, 3H).

54

Preparation of Example 3

Ex 3-Step 2 product was converted to Example 3 following the general procedures outlined in Example 1 (steps 1-5) and then Example 2 (steps 1 and 2): LCMS m/z 339.1 (M+1); $^1$H NMR (400 MHz, $CDCl_3$) δ 8.34 (d, J=5.3, 1H), 8.18 (s, 1H), 7.30-7.33 (m, 2H), 7.23-7.25 (m, 2H), 6.91 (d, J=5.2, 1H), 4.38 (s, 2H), 3.94 (s, 3H), 3.17 (s, 3H).

Example 4

4-[3-(4-fluorophenyl)-1-methyl-1H-pyrazol-4-yl]-6,7-dihydro-5H-pyrrolo[3,4-b]pyridin-5-one

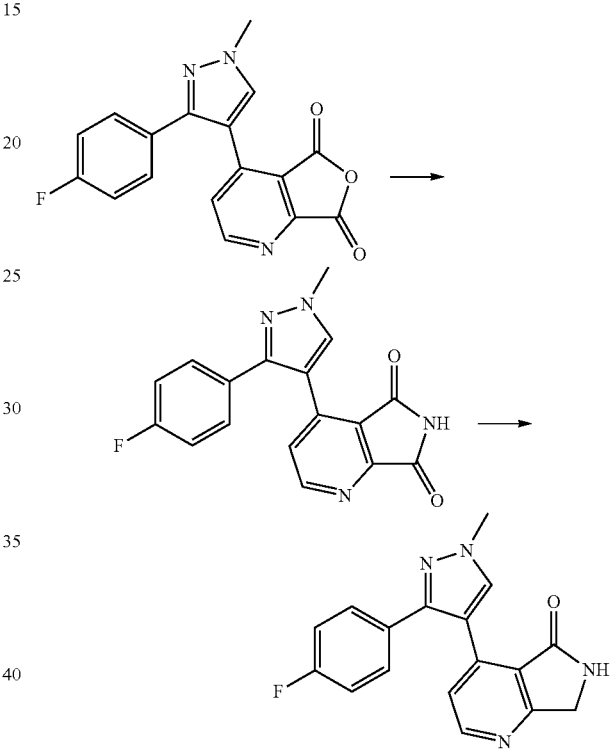

Step 1 Preparation of 4-(3-(4-fluorophenyl)-1-methyl-1H-pyrazol-4-yl)-5H-pyrrolo[3,4-b]pyridine-5,7(6H)-dione 4-(3-(4-fluorophenyl)-1-methyl-1H-pyrazol-4-yl)-6-methyl-5H-pyrrolo[3,4-b]pyridine-5,7(6H)-dione (intermediate from Example 1, step 5, 190 mg, 0.588 mmol) and 28-30% aqueous ammonium hydroxide (4 mL) were heated to a vigorous reflux for 30 min and then concentrated. The residue was dissolved in 1:1 acetic acid/acetic anhydride (20 mL) and heated at 120° C. for 2 hr and concentrated. The residue was dissolve in EtOAc and run through a short silica gel plug to afford 176 mg (92%) of Ex 4-Step 1 product as a white solid which was used without further purification: LCMS m/z 323.1 (M+1); $^1$H NMR (400 MHz, $CDCl_3$) δ 8.63 (d, J=5.2, 1H), 8.15 (s, 1H), 7.37 (dd, J=8.8, 5.5, 2H), 7.17 (d, J=5; 3, 1H), 7.04 (dd, J=8.6, 8.6, 2H), 4.01 (s, 3H).

Step 2

Example 4

Example 4 was prepared in 71% yield from Ex 4-Step 1 product following the general procedure described in Example 2, step 2 using 5 equivalents of zinc dust and heating for 1.5 hr: LCMS m/z 309.1 (M+1); $^1$H NMR (400 MHz, CDCl$_3$) δ 8.40 (d, J=5.4, 1H), 8.21 (s, 1H), 7.37-7.49 (m, 2H), 6.95-7.03 (m, 3H), 6.14 (br s, 1H), 4.74 (s, 2H), 3.98 (s, 3H).

Example 5

6-benzyl-4-[3-(4-fluorophenyl)-1-methyl-1H-pyrazol-4-yl]-6,7-dihydro-5H-pyrrolo[3,4-b]pyridin-5-one

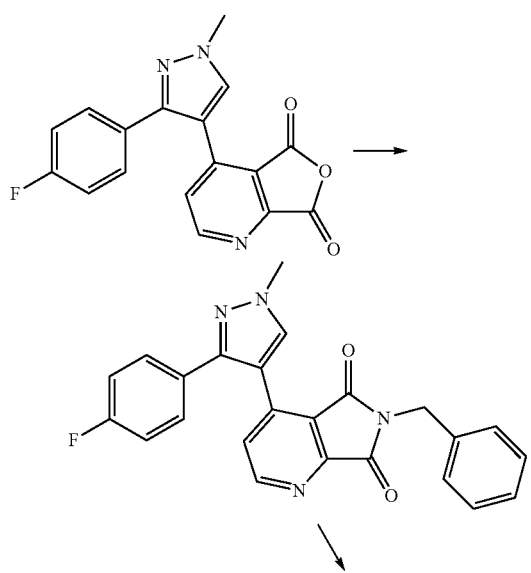

Step 1 Preparation of 6-benzyl-4-(3-(4-fluorophenyl)-1-methyl-1H-pyrazol-4-yl)-5H-pyrrolo[3,4-b]pyridine-5,7(6H)-dione 4-[3-(4-Fluorophenyl)-1-methyl-1H-pyrazol-4-yl]furo[3,4-b]pyridin-5(7H)-one (Example 1, step 5, 472 mg, 1.46 mmol) and benzyl amine (0.167 mL, 1.53 mmol) in acetic acid (4.7 mL) were heated at reflux for 18 hr, cooled and then concentrated to a brown solid. This material was stirred with diethyl ether (20 mL) for 10 min and then filtered to yield 450 mg (75%) of Ex 5-Step 1 product as a tan colored solid: LCMS m/z 413.5 (M+1); $^1$H NMR (400 MHz, CDCl$_3$) δ 8.57 (d, J=5.2, 1H), 8.15 (s, 1H), 7.26-7.42 (m, 7H), 7.13 (d, J=5.3, 1H), 7.01 (dd, J=8.6, 8.6, 2H), 4.87 (s, 2H), 4.00 (s, 3H).

Step 2 Preparation of 6-benzyl-4-[3-(4-fluorophenyl)-1-methyl-1H-pyrazol-4-yl]-6,7-dihydro-5H-pyrrolo[3,4-b]pyridin-5-one Boron trifluoride-diethyl etherate (0.18 mL, 1.45 mmol) was added to a solution of Ex 5-Step 1 product (100 mg, 0.242 mmol) in THF (2.4 mL). After stirring 30 min at rt, borane THF complex (1.0M/THF, 1.21 mL, 1.21 mmol) was added and the mixture was heated to 40° C. overnight. A few drops of 6N HCl were added and the mixture was refluxed for 1 hr, cooled and concentrated. Silica gel chromatography of the resulting material using a 5-10% MeOH/EtOAc gradient yielded 6 mg (6%) of Example 5 as a gum: LCMS m/z 399.5 (M+1); $^1$H NMR (400 MHz, MeOH-d$_4$) δ 8.44 (d, J=5.5, 1H), 8.14 (s, 1H), 7.20-7.36 (m, 7H), 7.12 (d, J=5.2, 1H), 7.03 (dd, J=8.8, 8.8, 2H), 4.72 (s, 2H), 4.33 (s, 2H), 3.96 (s, 3H).

Example 6

6-benzyl-4-[3-(4-fluorophenyl)-1-methyl-1H-pyrazol-4-yl]-6,7-dihydro-5H-pyrrolo[3,4-b]pyridine

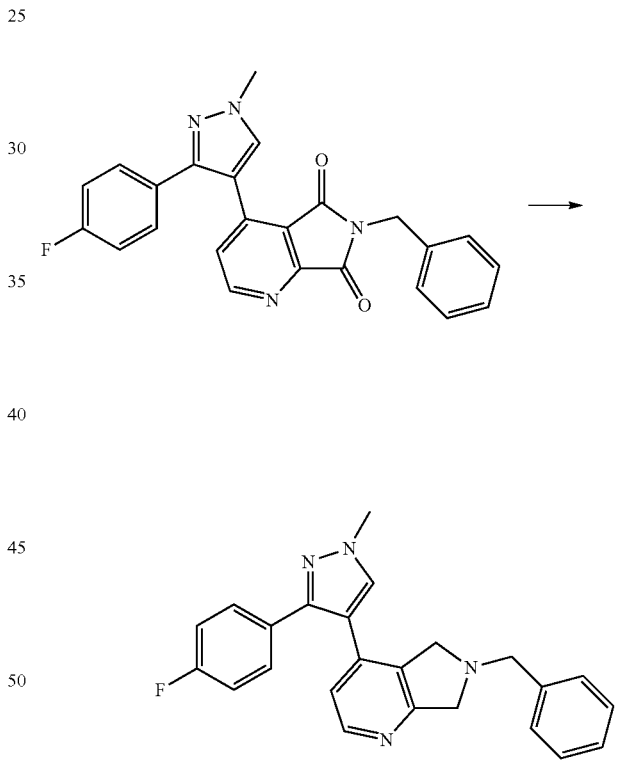

Lithium aluminum hydride (LAH), (1.0 M/THF, 1.10 mL, 1.10 mmol) was added dropwise to a solution of Example 5 (114 mg, 0.276 mmol) in THF (2.8 mL). The mixture was stirred at rt overnight, cooled to 0° C. and quenched with a few drops of saturated aqueous Na$_2$SO$_4$ solution. The reaction was extracted with CH$_2$Cl$_2$ (3×50 mL), filtered (celite), dried over MgSO$_4$ and concentrated. This material was purified on a Phenomenex Phenyl Hexyl column (150×3.0 mm, 5μ) using a 5-100% MeOH/water with 0.1% formic acid gradient to yield 5 mg (5%) of the title compound which was converted to the hydrochloride salt: LCMS m/z 399.5 (M+1); $^1$H NMR (400 MHz, MeOH-d$_4$) δ 8.49 (d, J=4.7, 1H), 8.01 (s, 1H), 7.44-7.52 (m, 5H), 7.32-7.38 (m, 3H), 7.14 (dd, J=8.6, 8.6, 2H), 4.76 (brs, 2H), 4.57 (brs, 2H), 4.31 (br s, 2H), 4.00 (s, 3H).

Example 7

9-[3-(4-fluorophenyl)-1-methyl-1H-pyrazol-4-yl]-2,3,4,5-tetrahydropyrido[2,3-f][1,4]oxazepine

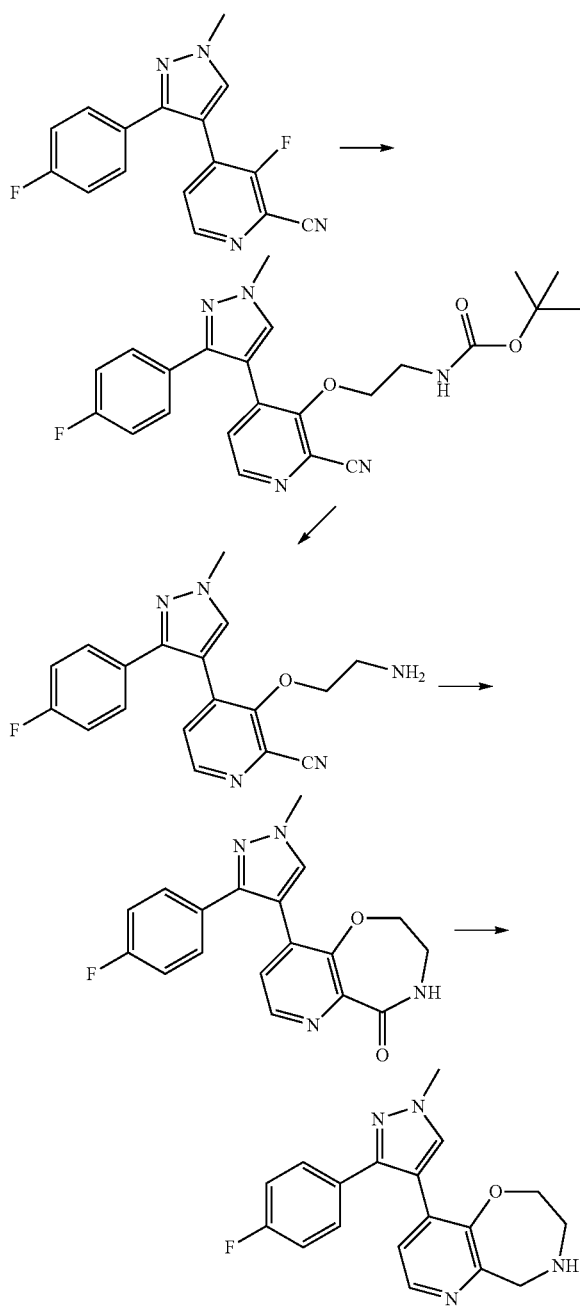

Step 1: Preparation of tert-butyl 2-(2-cyano-4-(3-(4-fluorophenyl)-1-methyl-1H-pyrazol-4-yl)pyridin-3-yloxy)ethylcarbamate 60% Sodium hydride (1.35 g, 33.8 mmol) was added to a solution of N-Boc-ethanolamine (2.62 mL, 16.9 mmol) in THF (85 mL). After stirring 5 min at rt, Example 1-Step 2 product (5.0 g, 17.0 mmol) was added with stirring. The mixture was stirred for 30 min then quenched with saturated aqueous NH$_4$Cl and diluted with EtOAc (100 mL). The organic phase was separated, dried (MgSO$_4$) and concentrated to yield 1.4 g of a viscous oil. Purification by silica gel chromatography using 40-60%% EtOAc/heptane gave 3.35 g (45%) of Ex 7-Step 1 product as a white solid: LCMS m/z 438.6 (M+1); $^1$H NMR (400 MHz, CDCl$_3$) δ 8.17 (d, J=5.1, 1H), 7.76 (s, 1H), 7.30 (dd, J=8.8, 5.5, 2H), 7.14 (d, J=4.9, 1H), 6.95 (dd, J=8.8, 8.8, 2H), 5.01 (br s, 1H), 3.94 (s, 3H), 3.91 (t, J=5.3, 2H), 3.30 (q, J=5.5, 2H), 1.33 (s, 9H).

Step 2: Preparation of 3-(2-aminoethoxy)-4-(3-(4-fluorophenyl)-1-methyl-1H-pyrazol-4-yl)picolinonitrile Ethanolic HCl (1.25 M, 33 mL, 41 mmol) was added to Ex 7-Step 1 product (3.35 g, 7.7 mmol) and the resulting solution was refluxed for 30 min, then concentrated to yield 2.90 g (92%) of Ex 7-Step 2 product, isolated as the di HCl salt as a white solid: MS (APCI) m/z 338.0 (M+1); $^1$H NMR (400 MHz, MeOH-d$_4$) δ 8.33 (d, J=4.9, 1H), 8.16 (s, 1H), 7.42 (dd, J=8.8, 5.3, 2H) 7.38 (d, J=5.1, 1H), 7.10 (dd, J=8.7, 2H); 4.14 (t, J=5.2, 2H), 4.03 (s, 3H), 3.22 (t, J=5.1, 2H).

Step 3: (9-(3-(4-fluorophenyl)-1-methyl-1H-pyrazol-4-yl)-3,4-dihydropyrido[2,3-f][1,4]oxazepin-5(2H)-one Ex 7-Step 2 Product (2.90 g, 7.07 mmol) and 1N aqueous NaOH (29 mL, 29 mmol) were stirred for 2 hr at 85° C. The reaction was cooled to rt and the precipitate was collected, rinsed with water and air dried to yield 1.92 g (80%) of Ex 7-Step 3 product as a light tan colored solid: MS (APCI) m/z (M+1) 338.8; $^1$H NMR (400 MHz, DMSO-d$_6$) δ 8.47 (t, J=6.1, 1H), 8.27 (d, J=4.7, 1H), 7.33 (dd, J=9.0, 5.7, 2H), 7.11-7.17 (m, 3H), 3.89 (s, 3H), 3.84 (t, J=5.3, 2H), 3.15 (dt, J=5.5, 4.7, 2H)

Step 4

Example 7

Lithium aluminum hydride (LAH) (1.0M in THF, 11.4 mL, 11.4 mmol) was added to a solution of Ex 7-Step 3 product (1.92 g, 5.68 mmol) in THF (56 mL) and the resulting mixture was refluxed for 1 hr. After cooling to rt, the excess LAH was quenched with a minimum amount of water and diluted with EtOAc. The resulting slurry was filtered through celite, the filtrate was then concentrated to yield 1.8 g of light yellow solid. Silica gel chromatography with 5% MeOH/CH$_2$Cl$_2$ yielded 650 mg (35%) of Example 7 as a light yellow gum. The di-hydrochloride salt was prepared in EtOAc with 2N HCl/diethyl ether to give 537 mg of light peach colored solid: MS (APCI) m/z 325.0 (M+1); $^1$H NMR (400 MHz, MeOH-d$_4$) δ 8.29 (d, J=5.7, 1H), 8.15 (s, 1H), 7.45 (d, J=5.7, 1H), 7.41 (dd, J=8.8, 5.3, 2H), 7.13 (dd, J=8.9, 8.9, 2H), 4.68 (s, 2H), 4.21-4.24 (m, 2H), 3.99 (s, 3H), 3.66-3.68 (m, 2H).

Example 8

9-[3-(4-fluorophenyl)-1-methyl-1H-pyrazol-4-yl]-2-methyl-2,3,4,5-tetrahydropyrido[2,3-f][1,4]oxazepine

Step 3: Preparation of 9-(3-(4-fluorophenyl)-1-methyl-1H-pyrazol-4-yl)-2-methyl-3,4-dihydropyrido[2,3-f][1,4]oxazepin-5(2H)-one Ex 8-Step 3 product was prepared from ~75% pure Ex 8-Step 2 product following the general procedures described

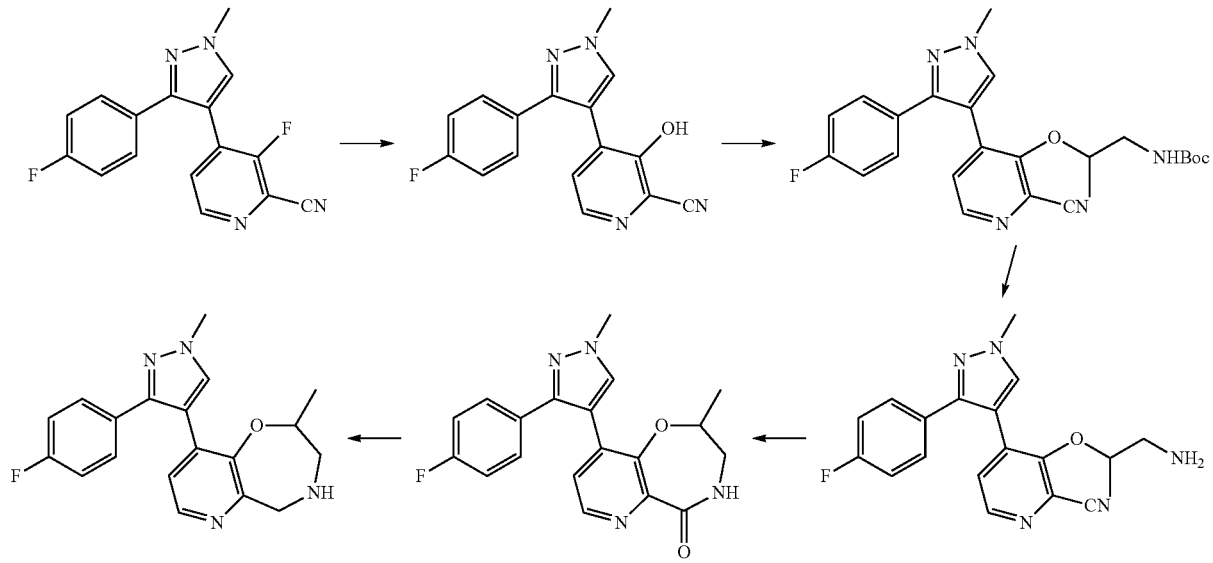

Step 1: Preparation of 4-(3-(4-fluorophenyl)-1-methyl-1H-pyrazol-4-yl)-3-hydroxypicolinonitrile Sodium hydride (60%, 4.05 mg, 10.1 mmol) was added to a 0° C. solution of Example 1, Step 2 product (1.00 g, 3.38 mmol) and 2-(methylsulfonyl)ethanol (629 mg, 5.06 mmol) in THF (20 mL). The mixture was warmed to rt and stirred for 18 hr. Saturated aqueous ammonium chloride solution was added to quench the excess sodium hydride and the mixture was extracted into EtOAc. The organic phase was separated, dried (MgSO$_4$) and concentrated. Silica gel chromatography with a 20% to 100% EtOAc/heptanes gradient gave Ex 8-Step 1 product in quantitative yield: LCMS m/z 295.1 (M+1); $^1$H NMR (400 MHz, CDCl$_3$) δ 8.19 (d, J=4.7, 1H), 7.74 (s, 1H), 7.40 (dd, J=8.8, 5.3, 2H), 7.23 (d, J=4.7, 1H), 7.05 (dd, J=8.6, 8.6, 2H), 4.03 (s, 3H).

Step 2: Preparation of tert-butyl 2-(2-cyano-4-(3-(4-fluorophenyl)-1-methyl-1H-pyrazol-4-yl)pyridin-3-yloxy)propylcarbamate Diisopropyl azodicarboxylate (0.78 mL, 3.70 mmol) was added to an ice cold solution of Ex 8-Step 1 product (990 mg, 3.36 mmol), tert-butyl 2-hydroxypropylcarbamate (590 mg, 3.36 mmol) and triphenylphosphine (1.06 g, 4.04 mmol). The mixture was stirred at rt for 3 hr. The reaction was loaded onto silica gel and purified by chromatography using a 10-60% EtOAc/heptanes gradient to yield 1.48 g of ~75% pure Ex 8-Steph 2 product as a yellow gum which was used without further purification: LCMS m/z 452.2 (M+1).

in Example 6 (steps 2 and 3): LCMS m/z 353.2 (M+1); $^1$H NMR (400 MHz, CDCl$_3$) δ 8.39 (d, J=4.9, 1H), 7.72 (s, 1H), 7.41 (dd, J=8.8, 5.4, 2H), 7.35 (br t, J=6.7, 1H), 7.20 (d, J=4.9, 1H), 7.04 (dd, J=8.6, 8.6, 2H), 4.31-4.38 (m, 1H), 4.02 (s, 3H), 3.40 (ddd, J=15.6, 6.4, 3.7, 1H), 3.14 (ddd, J=15.6, 6.1, 6.1, 1H), 1.15 (d, J=6.4, 3H).

Step 4

Example 8

Zinc dust (121 mg, 1.84 mmol) and Ex 8-Step 3 product (130 mg, 0.37 mmol) were stirred in acetic acid (10 mL) at 110° C. for 18 hr. LCMS showed a mixture of the title compound and its N-acetyl derivative (1-(9-(3-(4-fluorophenyl)-1-methyl-1H-pyrazol-4-yl)-2-methyl-2,3-dihydropyrido[2,3-f][1,4]oxazepin-4(5H)-yl)ethanone). The reaction was cooled to 25° C. and filtered (celite) with acetic acid rinse. The filtrate was concentrated, then 6N HCl (5 mL) and MeOH (6 mL) were added and the mixture was refluxed for 20 hr. The reaction was concentrated, re-dissolved in 3:1 chloroform/isopropyl alcohol and washed with saturated aqueous K$_2$CO$_3$, water and brine then dried (MgSO$_4$) and concentrated. Chromatography using a 100% CH$_2$Cl$_2$ to 10% MeOH/CH$_2$Cl$_2$ gradient yielded 83 mg (66%) of Example 8 as a racemic mixture. The enantiomers were separated by chiral HPLC (Chiralpak AD-H, 4.6 mm×25 cm; mobile phase 85/15 carbon dioxide/EtOH; flow 2.5 mL/min; modifier 0.2% isopropyl amine). Enantiomer #1: RetT=5.30 min; LCMS m/z 339.2 (M+1); $^1$H NMR (400 MHz, CDCl$_3$) δ 8.05 (d, J=5.1, 1H), 7.69 (s, 1H), 7.43 (dd, J=8.9, 5.4, 2H), 7.02 (dd, J=8.8, 8.8, 2H), 6.94 (d, J=5.1, 1H), 4.20 (AB quartet, J$_{AB}$=15.0, Δv$_{AB}$=13.4, 2H), 4.00 (s, 3H), 3.72-3.76 (m, 1H), 3.17 (dd, J=14.0, 1.9, 1H), 2.95 (dd, J=14.3, 4.7, 1H), 1.12 (d, J=6.4, 3H).

Enantiomer #2: RetT=5.84 min; LCMS m/z 339.2 (M+1); ¹H NMR same as for enantiomer #1.

Example 9

9-[3-(4-fluorophenyl)-1-methyl-1H-pyrazol-4-yl]-3-methyl-2,3,4,5-tetrahydropyrido[2,3-f][1,4]oxazepine

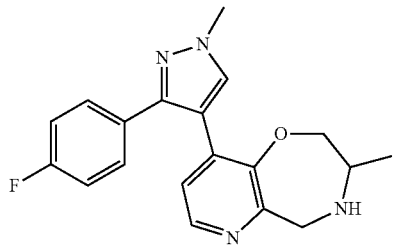 [SMILES: CC1COc2c(-c3cn(C)nc3-c3ccc(F)cc3)ccnc2CN1]

Example 9 was prepared following the same general procedures described in Example 7, substituting tert-butyl 1-hydroxypropan-2-ylcarbamate for tert-butyl 2-hydroxypropylcarbamate in step 2 and the enantiomers were separated by chiral HPLC (Chiralpak AD-H, 10 mm×250 cm; mobile phase 80/20 carbon dioxide/EtOH; flow 10 mL/min; modifier 0.2% isopropyl amine): Enantiomer #1: RetT=4.30 min; LCMS m/z 339.2 (M+1); ¹H NMR (400 MHz, CDCl₃) δ 8.06 (d, J=4.8, 1H), 7.65 (s, 1H), 7.41 (dd, J=8.8, 5.5, 2H), 7.03 (dd, J=8.8, 8.8, 2H), 6.93 (d, J=5.1, 1H), 4.30 (s, 2H), 4.07 (dd, J=11.9, 2.5, 1H), 4.00 (s, 3H), 3.25-3.30 (m, 1H), 3.17-3.22 (m, 2H), 1.04 (d, J=6.5, 3H).

Enantiomer #2: RetT=4.73 min; LCMS m/z 339.2 (M+1); ¹H NMR same as for enantiomer #1.

Example 10

4-[3-(4-fluorophenyl)-1-methyl-1H-pyrazol-4-yl]-6-(methylsulfonyl)-6,7-dihydro-5H-pyrrolo[3,4-b]pyridine

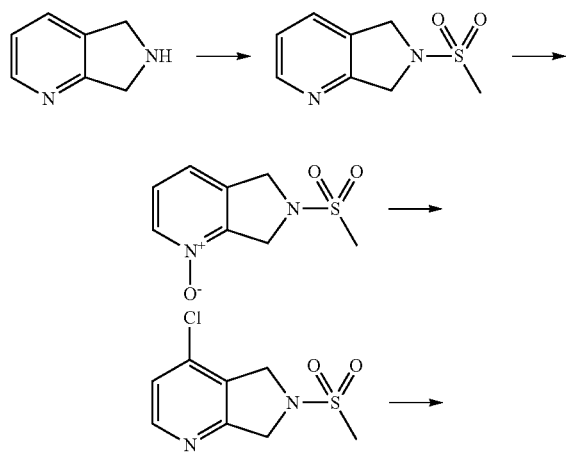

-continued

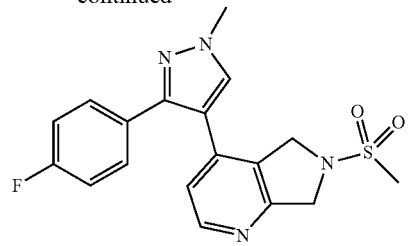

Step 1: Preparation of 6-(methylsulfonyl)-6,7-dihydro-5H-pyrrolo[3,4-b]pyridine

Methanesulfonyl chloride (0.97 mL, 12.4 mmol) was added dropwise to a −10° C. solution of diisopropyl-ethylamine (5.16 mL, 31.1 mmol) and 6,7-dihydro-5H-pyrrolo[3,4-b]pyridine (2.0 g, 10.0 mmol) in CH₂Cl₂ (20 mL). The mixture was stirred overnight at rt diluted with CH₂Cl₂ (300 mL) and washed with saturated aqueous sodium bicarbonate. The organic phase was separated, dried (MgSO₄) and filtered through a short silica gel pad with EtOAc rinse. The filtrate was concentrated to yield 2.15 g (quantitative) of Ex 10-Step 1 product as a solid which was used without further purification: LCMS m/z 199.2 (M+1); ¹H NMR (400 MHz, CDCl₃) δ 8.54 (d, J=4.9, 1H), 7.61 (d, J=7.8, 1H), 7.25 (dd, J=7.8, 5.1, 1H), 4.75 (AB quartet, $J_{AB}$=2.1, $\Delta v_{AB}$=7.8, 4H), 2.94 (s, 3H).

Step 2: Preparation of 6-(methylsulfonyl)-6,7-dihydro-5H-pyrrolo[3,4-b]pyridine 1-oxide Ex 10-Step 2 product was prepared in 95% yield as a white solid from Ex 10-Step 1 product following the general procedure described in Example 1, Step 9: LCMS m/z 215.01 (M+1); ¹H NMR (400 MHz, CDCl₃) δ 8.16 (d, J=6.5, 1H), 7.29 (dd, J=7.5, 7.5, 1H), 7.18 (d, J=7.8, 1H), 4.82-4.89 (m, 4H), 2.96 (s, 3H).

Step 3: Preparation of 4-chloro-6-(methylsulfonyl)-6,7-dihydro-5H-pyrrolo[3,4-b]pyridine Oxalyl chloride (0.415 mL, 4.67 mmol) was added dropwise to a 0° C. suspension of Ex 10-Step 2 product (500 mg, 2.33 mmol) in DMF (40 mL). The resulting mixture was warmed to rt and stirred for 18 hr. Water was added slowly to quench the excess oxalyl chloride and the mixture was extracted into CH₂Cl₂ (250 mL). The extract was washed with brine, dried (MgSO₄) and concentrated to yield a brown gum which was then purified by silica gel chromatography using a 100% heptanes to 50% EtOAc/heptanes gradient. 2-Chloro-6-(methylsulfonyl)-6,7-dihydro-5H-pyrrolo[3,4-b]pyridine (76 mg, 14%) eluted from the column first followed by Ex 10-Step 3 product (240 mg, 44%, white solid): ¹H NMR (400 MHz, CDCl₃) δ 8.45 (d, J=5.5, 1H), 7.26 (d partially obscured by residual CHCl₃ peak, 1H), 4.80 (br s, 4H), 2.97 (s, 3H).

Step 4

Example 10

Ex 10-Step 3 Product (100 mg, 0.43 mmol), Ex 1-Step 1 product, (156 mg, 0.516 mmol), LiOH (30.9 mg, 1.29 mmol) and dichloro 1,1'-bis(diphenylphosphino)ferrocene palladium (II) (35.1 mg, 0.043 mmol) were combined as solids and degassed by evacuating and back filling with nitrogen gas (3 times). DMF (30 mL) was added and the mixture was heated for 2 hr at 100° C. Following cooling to rt, EtOAc was added and the mixture was filtered (celite) with EtOAc rinse. The filtrate was washed with water and brine, dried (MgSO$_4$) and concentrated. Silica gel chromatography using a 40-80% EtOAc/heptanes gradient afforded 102 mg (64%) of Example 10 as a light brown solid: LCMS m/z 373.1 (M+1); $^1$H NMR (400 MHz, MeOH-d$_4$) δ 8.47 (d, J=6.4, 1H), 8.28 (s, 1H), 7.42-7.48 (m, 3H), 7.15 (dd, J=8.8, 8.8, 2H), 4.96-4.97 (m, 2H), 4.77-4.79 (m, 2H), 4.02 (s, 3H), 3.00 (s, 3H).

Example 11

6-(ethylsulfonyl)-4-[3-(4-fluorophenyl)-1-methyl-1H-pyrazol-4-yl]-6,7-dihydro-5H-pyrrolo[3,4-b]pyridine

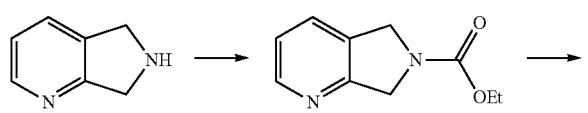

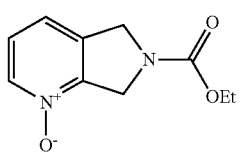

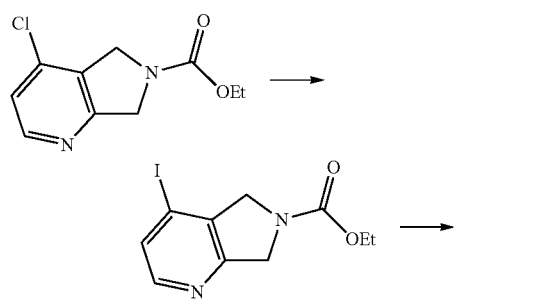

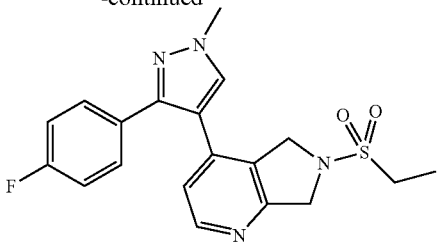

Step 1: Preparation of ethyl 4-chloro-5H-pyrrolo[3,4-b]pyridine-6(7H)-carboxylate Ex 11-Step 1 product was prepared using the general procedures described in Example 10 (steps 1-3) substituting ethylchloroformate for methanesulfonyl chloride in step 1. The material was obtained as a pink solid: MS (APCI) m/z 226.9 (M+1); $^1$H NMR shows a mixture of rotamers (400 MHz, CDCl$_3$) δ 8.43 (d, J=5.4, 1H), 7.23-7.26 (m, 1H), 4.75-4.85 (m, 4H), 4.26 (q, J=7.1, 2H), 1.31-1.36 (overlapping triplets, J=7.2, 3H total). This material was converted to the HCl salt for use in the next step.

Step 2: Preparation of ethyl 4-iodo-5H-pyrrolo[3,4-b]pyridine-6(7H)-carboxylate

Sodium iodide (3.93 g, 26.2 mmol) and Ex 11-Step 1 product, hydrochloride salt (step 1, 2.30 g, 8.74 mmol) in acetonitrile (20 mL) were refluxed for 3 days. The reaction mixture was cooled, concentrated and partitioned between CH$_2$Cl$_2$ and saturated aqueous sodium bicarbonate. The phases were separated and the aqueous phase was re-extracted twice with CH$_2$Cl$_2$ (total volume 750 mL). The solution was passed through a plug of silica gel (0.5") layered with celite (0.5") using 1:1 EtOAc/CH$_2$Cl$_2$ for elution to yield 1.98 g (71%) of Ex 11-Step 2 product as a brown solid: $^1$H NMR shows a ~1:1 mixture of rotamers (400 MHz, CDCl$_3$) δ 8.08-8.11 (overlapping doublets, 1H total), 7.61 (br d, J=5.3, 1H), 4.89/4.84 (br singlets, 2H total), 4.68/4.64 (br singlets, 2H total), 4.23-4.29 (overlapping quartets, 2H total), 1.32-1.37 (overlapping triplets, 3H total).

Step 3: Preparation of ethyl 4-(3-(4-fluorophenyl)-1-methyl-1H-pyrazol-4-yl)-5H-pyrrolo[3,4-b]pyridine-6(7H)-carboxylate Ex 11-Step 3 product was prepared as a light brown solid in 68% yield following the general procedure described in Example 10 (step 4) using ethyl 4-iodo-5H-pyrrolo[3,4-b]pyridine-6(7H)-carboxylate in place of 4-chloro-6-(methylsulfonyl)-6,7-dihydro-5H-pyrrolo[3,4-b]pyridine and 2 equivalents of cesium fluoride instead of LiOH: LCMS m/z 367.2.1 (M+1); $^1$H NMR (400 MHz, MeOH-d$_4$) δ ~1:1 mixture of rotamers, 8.47-8.50 (2 overlapping doublets, 1H), 8.28 (br s, 1H), 7.44-7.52 (m, 3H), 7.15-7.19 (2 overlapping doublets, 2H), 4.97/5.00 (br singlets, 2H), 4.77/4.80 (br singlets, 2H), 4.20-4.27 (2 overlapping quartets, 2H), 4.05 (br s, 3H), 1.30-1.35 (2 overlapping triplets, 3H).

Step 4: Preparation of 4-(3-(4-fluorophenyl)-1-methyl-1H-pyrazol-4-yl)-6,7-dihydro-5H-pyrrolo[3,4-b]pyridine Aqueous KOH (10M, 10.3 mL, 103 mmol), Ex 11-Step 3 product (1.51 g, 4.12 mmol), MeOH (15 mL) and water (15 mL) were heated at 90° C. for 18 hr. After cooling to rt, water (10 mL) was added and the mixture was extracted twice with 3:1 chloroform/isopropanol. The extracts were concentrated to afford 1.2 g (99%) of Ex 11-Step 4 product as a pink solid: MS (APCI) m/z 295.0.1; (M+1); $^1$H NMR (400 MHz, CDCl$_3$) δ 8.34 (d, J=5.3, 1H), 7.47 (s, 1H), 7.39 (dd, J=9.0, 5.5, 2H), 7.02 (dd, J=8.8, 8.8, 2H), 6.94 (d, J=5.3, 1H), 4.28 (br s, 2H), 3.97 (br s, 2H).

Step 5

Example 11 as, HCl Salt

Ethanesulfonyl chloride (24 μL, 0.26 mmol) was added to a solution of Ex 11-Step 4 product (75 mg, 0.26 mmol) and triethylamine (106 μL, 0.77 mmol) in CH$_2$Cl$_2$ (8 mL). After stirring for 5 min, the reaction was diluted with CH$_2$Cl$_2$ and washed with saturated aqueous sodium bicarbonate, dried (Na$_2$SO$_4$) and concentrated to yield 89 mg (91%) of Example 11 which was converted into a hydrochloride salt: LCMS m/z 387.1 (M+1); $^1$H NMR (400 MHz, CDCl$_3$) δ 8.43 (d, J=5.0, 1H), 7.51 (s, 1H), 7.38 (dd, J=8.2, 5.6, 2H), 7.02-7.06 (m, 3H), 4.76 (br s, 2H), 4.46 (br s, 2H), 4.02 (s, 3H), 3.00 (q, J=7.5, 2H), 1.34 (t, J=7.3, 3H).

Example 12

6-(cyclopropylsulfonyl)-4-[3-(4-fluorophenyl)-1-methyl-1H-pyrazol-4-yl]-6,7-dihydro-5H-pyrrolo[3,4-b]pyridine

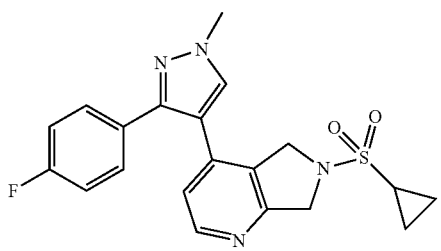 [SMILES: Cn1cc(-c2ccnc3c2CN(S(=O)(=O)C2CC2)C3)c(-c2ccc(F)cc2)n1]

Example 12 was prepared following the general procedure described in Example 11, step 5, substituting cyclopropanesulfonyl chloride for ethanesulfonyl chloride to yield the hydrochloride salt in 88% yield: LCMS m/z 399.1 (M+1); $^1$H NMR (400 MHz, MeOH-d$_4$) mixture of rotamers, 8.54 (br s, 1H), 8.31 (brs, 1H), 7.57 (br s, 1H), 7.47 (br s, 2H), 7.19 (br s, 2H), 5.06 (br s, 2H), 4.79 (br s, 2H), 4.05 (br s, 3H), 2.70 (br s, 1H), 1.14 (br s, 2H), 1.06 (br s, 2H).

Example 13

4-[3-(4-fluorophenyl)-1-methyl-1H-pyrazol-4-yl]-6-propionyl-6,7-dihydro-5H-pyrrolo[3,4-b]pyridine

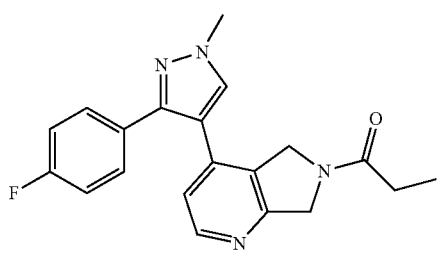 [SMILES: CCC(=O)N1Cc2nccc(-c3cn(C)nc3-c3ccc(F)cc3)c2C1]

Triethylamine (142 μL, 1.02 mmol), propionic acid (22.9 μL, 0.31 mmol) and propylphosphonic anhydride (T3P) solution (50% wt, 360 μL, 0.60 mmol) were added to a solution of Example 11 (75 mg, 0.26 mmol) in EtOAc (4 mL). The resulting slurry was stirred at rt for 2 hr then diluted with CH$_2$Cl$_2$, washed with saturated aqueous K$_2$CO$_3$, dried (Na$_2$SO$_4$) and concentrated. The residue was redissolved in EtOAc and treated with excess 2N HCl in diethyl ether to yield 113 mg of the hydrochloride salt of Example 12 as a solid in quantitative yield: LCMS m/z 351.1 (M+1); $^1$H NMR (400 MHz, MeOH-d$_4$) mixture of rotamers, 8.52 (br d, J=6.3, 1H), 8.32/8.36 (singlets, 1H), 7.45-7.54 (m, 3H), 7.15-7.21 (m, 2H), 4.98/5.03/5.20 (3 br singlets, 4H total), 4.06/4.07 (singlets, 3H total), 2.43-2.52 (m, 2H), 1.16-1.21 (2 overlapping triplets, 3H).

Examples 14-22

Examples 14 to 22 in Table 1 were prepared following the general procedure outlined in Example 13, where R$^2$ is from:

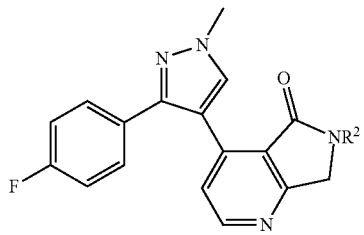

TABLE 1

| Ex No | R$^2$ | IUPAC NAME | LCMS m/z (M+1) | $^1$H-NMR |
|---|---|---|---|---|
| 14 | —C(O)—CH$_3$ | 6-acetyl-4-[3-(4-fluorophenyl)-1-methyl-1H-pyrazol-4-yl]-6,7-dihydro-5H-pyrrolo[3,4-b]pyridine, HCl salt | 337.2 | (MeOH-d4) ~1.5:1 mixture of rotamers, 8.44-8.47 (m, 1H), 8.22/8.29 (singlets, 1H), 7.40-7.46 (m, 3H), 7.10-7.18 (m, 2H), 4.95/5.13 (br singlets, 4H), 4.01/4.03 (singlets, 3H), 2.14/2.17 (singlets, 3H) |
| 15 | -C(O)-CH$_2$-cyclopropyl | 6-(cyclopropylacetyl)-4-[3-(4-fluorophenyl)-1-methyl-1H-pyrazol-4-yl]-6,7-dihydro-5H-pyrrolo[3,4-b]pyridine, HCl salt | 377.2 | (MeOH-d4) ~1.5:1 mixture of rotamers, 8.51/8.49 (2 doublets, J = 6.2, 1H total), 8.32/8.28 (singlets, 1H total), 7.44-7.53 (m, 3H), 7.14-7.21 (m, 2H), 5.01/5.15 (br singlets, 2H), 4.91/4.82 (br singlets, 2H), 4.05/4.06 (singlets, 3H), 3.47-3.49 and 3.12-31.4 (multiplets, 1H total), 2.36 and 2.42 (2 doublets, J = 6.9, 2H total), 0.56-0.62 (m, 2H), 0.19-0.26 (m, 2H). |

TABLE 1-continued

| Ex No | R² | IUPACNAME | LCMS m/z (M + 1) | ¹H-NMR |
|---|---|---|---|---|
| 16 | (C(O)-tetrahydrofuran-3-yl) | 4-[3-(4-fluorophenyl)-1-methyl-1H-pyrazol-4-yl]-6-(tetrahydrofuran-3-ylcarbonyl)-6,7-dihydro-5H-pyrrolo[3,4-b]pyridine, HCl salt | 393.2 | (MeOH-d4) ~1.5:1 mixture of rotamers, 8.50-8.53 (m, 1H), 8.36/8.30 (singlets, 1H), 7.44-7.56 (m, 3H), 7.15-7.21 (m, 2H), 5.28/5.02 (br singlets, 4H total), 4.06/4.05 (singlets, 3H total), 3.82-4.03 (m, 4H), 3.40 (br s, 1H), 2.07-2.15 (m, 2H). |
| 17 | (C(O)-CH₂-OCH₃) | 4-[3-(4-fluorophenyl)-1-methyl-1H-pyrazol-4-yl]-6-(methoxyacetyl)-6,7-dihydro-5H-pyrrolo[3,4-b]pyridine, HCl salt | 367.2 | (MeOH-d4) ~1:1 mixture of rotamers, 8.47-8.55 (m, 1H), 8.28-8.35 (m, 1H), 7.37-7.56 (m, 3H), 7.14-7.21 (m, 2H), 5.22/5.08/4.95/4.91 (br singlets, 4H total), 4.25/4.21 (br singlets, 2H total), 4.07/4.06 (singlets, 3H), 3.47/3.45 (singlets, 3H). |
| 18 | C(O)—CH(CH₃)₂ | 4-[3-(4-fluorophenyl)-1-methyl-1H-pyrazol-4-yl]-6-isobutyryl-6,7-dihydro-5H-pyrrolo[3,4-b]pyridine, HCl salt | 365.2 | (MeOH-d4) ~1:1 mixture of rotamers, 8.47-8.59 (m, 1H), 8.37/8.31 (br singlets, 1H total), 7.55-7.60 (m, 1H), 7.41-7.54 (m, 2H), 7.13-7.25 (m, 2H), 5.28/5.02/4.98 (br singlets, 4H total), 4.07/4.06 (singlets, 3H), 2.85 (br singlet, 1H), 1.20/1.15 (br doublets, J = 6.4, 6H). |
| 19 | (C(O)-tetrahydro-2H-pyran-4-yl) | 4-[3-(4-fluorophenyl)-1-methyl-1H-pyrazol-4-yl]-6-(tetrahydro-2H-pyran-4-ylcarbonyl)-6,7-dihydro-5H-pyrrolo[3,4-b]pyridine, HCl salt | 407.2 | (MeOH-d4) ~1.5:1 mixture of rotamers, 8.48-8.59 (m, 1H), 8.37/8.30 (br singlets, 1H total), 7.57-7.64 (m, 1H), 7.40-7.53 (m, 2H), 7.11-7.24 (m, 2H), 5.31/5.01/4.95/4.91 (br singlets, 4H total), 4.08/4.05 (singlets, 3H total), 3.95-4.04 (m, 2H), 3.45-3.60 (m, 2H), 2.7-2.95 (m, 1H), 1.55-1.90 (m, 4H). |
| 20 | (C(O)-CH₂-pyrimidin-2-yl) | 4-[3-(4-fluorophenyl)-1-methyl-1H-pyrazol-4-yl]-6-(pyrimidin-2-ylacetyl)-6,7-dihydro-5H-pyrrolo[3,4-b]pyridine | 415.2 | (CDCl3) ~1.5:1 mixture of rotamers, 8.73/8.67 (2 doublets, J = 5.1, 2H total), 8.48/8.35 (2 doublets, J = 5.1, 1H total), 7.56/7.49 (singlets, 1H total), 7.34-7.39 (m, 2H), 7.18-7.23 (m, 1H), 6.96-7.08 (m, 3H), 4.98/4.90 (br singlets, 2H total), 4.78/4.55 (br singlets, 2H total), 4.18/4.01 (singlets, 2H total), 4.00/3.96 (singlets, 3H total). |
| 21 | (C(O)-cyclopropyl) | 6-(cyclopropylcarbonyl)-4-[3-(4-fluorophenyl)-1-methyl-1H-pyrazol-4-yl]-6,7-dihydro-5H-pyrrolo[3,4-b]pyridine, HCl salt | 363.2 | (MeOH-d4) ~1.5:1 mixture of rotamers, 8.49-8.51 (overlapping doublets, 1H), 8.37/8.27 (singlets, 1H), 7.44-7.53 (m, 3H), 7.14-7.21 (m, 2H), 5.37/5.15/5.02/4.83 (broad singlets, 4H total), 4.04/4.06 (singlets, 3H), 1.88-1.95 (m, 1H), 0.93-1.00 (m, 4H). |
| 22 | (C(O)-O-CH₂-phenyl) | benzyl 4-[3-(4-fluorophenyl)-1-methyl-1H-pyrazol-4-yl]-5,7-dihydro-6H-pyrrolo[3,4-b]pyridine-6-carboxylate | 429.2 | (DMSO-d6) ~1:1 mixture of rotamers, 8.39-8.43 (2 overlapping doublets, 1H total), 8.21/8.25 (singlets, 1H), 7.33-7.43 (m, 7H), 7.16-7.22 (m, 2H), 7.05/7.01 (2 doublets, J = 5.6, 1H total), 5.17/5.14 (singlets, 2H total), 4.80/4.71 (singlets, 2H total), 4.64/4.62 (singlets, 2H total), 3.96/3.94 (singlets, 3H total) |

Example 23

4-[3-(4-fluorophenyl)-1-methyl-1H-pyrazol-4-yl]-6,7-dihydro-5H-cyclopenta[b]pyridine -continued

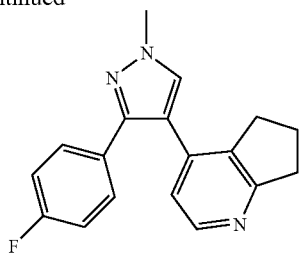

4-Chloro-6,7-dihydro-5H-cyclopenta[b]pyridine (350 mg, 2.28 mmol), Ex 1 Step 1 product (688 mg, 2.28 mmol), K₂CO₃ (661 mg, 4.78 mmol), 1,1-bis(diphenylphosphino) ferrocene palladium dichloride (84 mg, 0.144 mmol) in DMF (5 mL) were placed in a microwave vial and microwaved at 150° C. for 10 min. The reaction mixture was diluted with CH₂Cl₂ (10 mL) and water (5 mL). The layers were separated and the aqueous phase was extracted again with CH₂Cl₂. The combined organic phases were dried over MgSO₄, filtered and concentrated to yield a brown solution. Chromatography on 40 g of silica gel eluting with 9:1, 4:1 and 1:1 heptane: EtOAc yielded Example 23 as a light brown oil that solidified on standing (290 mg, 43%). LCMS m/z 294.5 (M+1). ¹H NMR (400 MHz, CDCl₃) δ 8.23 (d, J=5.3, 1H), 7.45 (s, 1H), 7.36 (dd, J=9.8, 5.4, 2H), 6.97 (dd, J=8.8, 8.8, 2H), 6.85 (d, J=5.1, 1H), 3.98 (s, 3H), 3.00 (t, J=7.6, 2H), 2.59 (t, J=7.3, 2H), 1.93-2.02 (m, 2H).

Example 24

4-[3-(4-fluorophenyl)-1-methyl-1H-pyrazol-4-yl]-6,7-dihydro-5H-cyclopenta[b]pyridin-7-ol Step 1: Preparation of 4-(3-(4-fluorophenyl)-1-methyl-1H-pyrazol-4-yl)-6,7-dihydro-5H-cyclopenta[b]pyridine 1-oxide 4-[3-(4-fluorophenyl)-1-methyl-1H-pyrazol-4-yl]-6,7-dihydro-5H-cyclopenta[b]pyridine was converted to the N-oxide following the general procedure described in Example 1, step 9. Silica gel chromatography using a 9:1 to 4:1 mixture of EtOAc/MeOH afforded 54% of Ex 24-Step 1 product as a yellow solid: LCMS m/z 310.5 (M+1); ¹H NMR (400 MHz, CDCl₃) δ 7.97 (d, J=6.6, 1H), 7.45 (s, 1H), 7.35 (dd, J=8.9, 5.4, 2H), 7.00 (dd, J=8.7, 8.7, 2H), 6.89 (d, J=6.6, 1H), 3.97 (s, 3H), 3.17 (t, J=7.6, 2H), 2.67 (t, J=7.6, 2H), 2.02-2.09 (m, 2H).

Step 2: Preparation of 4-(3-(4-fluorophenyl)-1-methyl-1H-pyrazol-4-yl)-6,7-dihydro-5H-cyclopenta[b]pyridin-7-yl acetate Ex 24-Step 1 Product (155 mg, 0.50 mmol) was heated at 105° C. in acetic anhydride (10 mL) overnight. The mixture was cooled, diluted with CH₂Cl₂ and washed with saturated aqueous sodium bicarbonate. The organic phase was dried (MgSO₄) and concentrated to give a brown oil. Silica gel chromatography using a 10%-90% EtOAc/heptanes gradient yielded 109 mg (62%) of Ex 24-Step 2 product as a white solid: LCMS m/z 352.5 (M+1); ¹H NMR (400 MHz, CDCl₃) δ 8.41 (d, J=5.1, 1H), 7.49 (s, 1H), 7.36 (dd, J=8.2, 5.4, 2H), 6.95-7.04 (m, 3H), 6.11 (dd, J=7.2, 5.3, 1H), 3.99 (s, 3H), 2.69-2.79 (m, 1H), 2.49-2.59 (m, 2H), 2.13 (s, 3H), 1.89-1.97 (m, 1H).

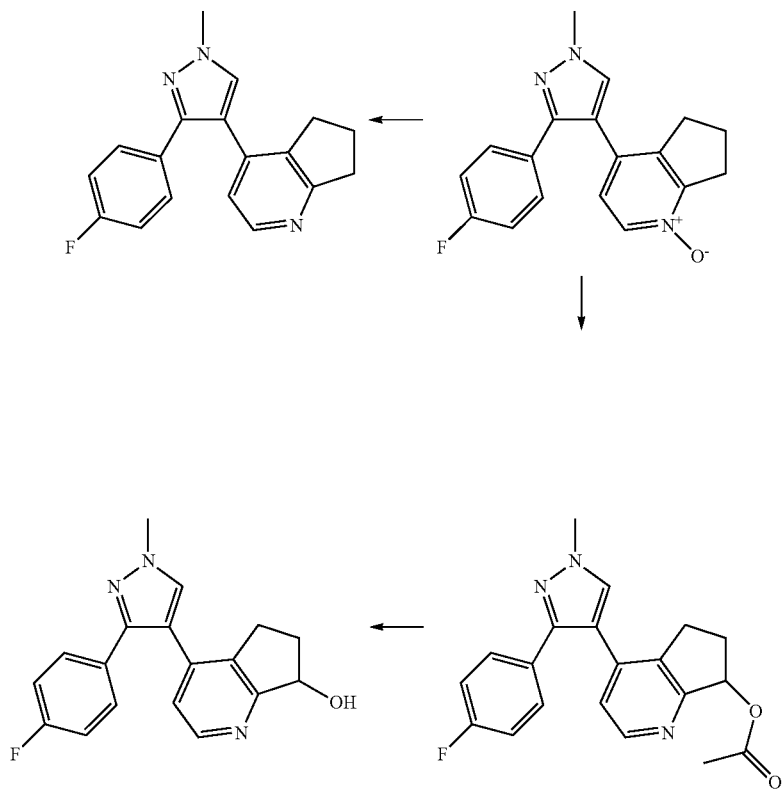

Step 3

Example 24

Partially dissolved Ex 24-Step 2 product (105 mg, 0.299 mmol) in 1.5 mL of MeOH. Added 1.5 mL of 10% aqueous $K_2CO_3$ solution and stirred at rt for 3 days. Concentrated the reaction, re-dissolved in EtOAc and washed with saturated sodium bicarbonate solution and brine. Dried over $Na_2SO_4$, filtered and concentrated to yield Example 24 as a brown solid (95 mg, quantitative yield) LCMS m/z 310.5 (M+1); $^1$H NMR (400 MHz, $CDCl_3$) δ 8.33 (d, J=5.1, 1H), 7.48 (s, 1H), 7.32-7.39 (m, 2H), 6.95-7.01 (m, 3H), 5.19 (dd, J=7.0, 7.0, 1H), 3.98 (s, 3H), 3.76 (br s, 1H), 2.70-2.79 (m, 1H), 2.40-2.52 (m, 2H), 1.86-1.97 (m, 2H).

Example 25

4-[3-(4-fluorophenyl)-1-methyl-1H-pyrazol-4-yl]-N-methyl-6,7-dihydro-5H-cyclopenta[b]pyridin-7-amine

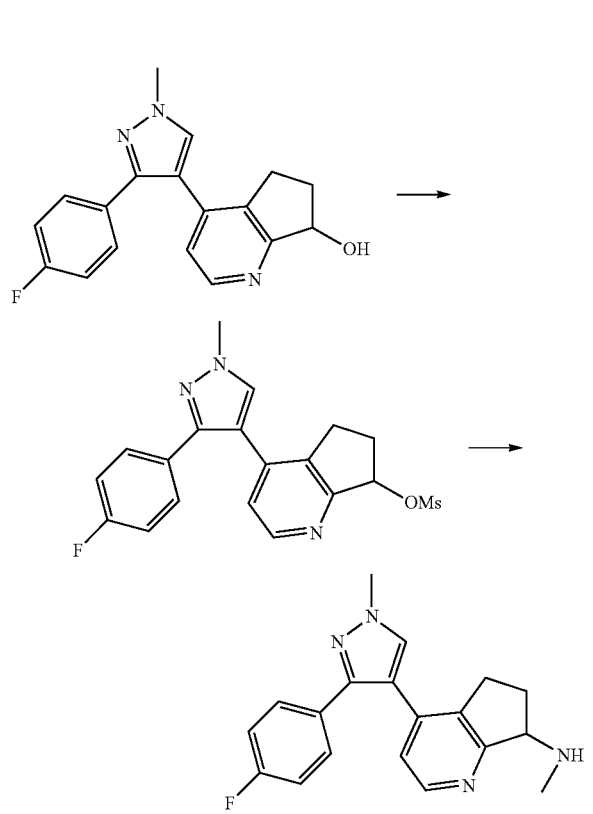

Example 23 (50 mg, 0.16 mmol) in $CH_2Cl_2$ (2 mL) was cooled to 0° C. Triethylamine (0.027 mL, 0.194 mmol) was added followed by methanesulfonyl chloride (0.013 mL, 0.170 mmol). The resulting mixture was stirred at 0° C. for 30 min. LCMS showed starting alcohol was still present so additional portions of triethylamine and methanesulfonyl chloride were added and stirring was continued until LCMS indicated the starting material was consumed. Water was added and the organic phase was separated, dried and concentrated to afford crude 4-(3-(4-fluorophenyl)-1-methyl-1H-pyrazol-4-yl)-6,7-dihydro-5H-cyclopenta[b]pyridin-7-yl methanesulfonate (62 mg, 99%) as a purple solid. THF (1 mL) was added to his crude mesylate followed by 1 mL of methylamine (2M in THF, 2 mmol) to give a brown solution. The reaction was stirred for 16 hours at rt and then purified by silica gel chromatography. Elution with 1:3, 1:1, and 1:3 heptane/EtOAc then EtOAc and 95:5 EtOAc/MeOH afforded 12 mg of 4-[3-(4-fluorophenyl)-1-methyl-1H-pyrazol-4-yl]-6,7-dihydro-5H-cyclopenta[b]pyridin-7-ol. Further elution with 95:5 EtOAc/2M ammonia in MeOH yielded 11 mg of a brown gum, which was dissolved in EtOAc and treated with excess 4M HCl/dioxane and stirred for 10 minutes. Filtration yielded Example 25 as a grey solid dihydrochloride salt (6 mg, 9%): LCMS m/z 323.5 (M+1); $^1$H NMR (400 MHz, MeOH-$d_4$) δ 8.43 (d, J=5.5, 1H), 8.01 (s, 1H), 7.37 (dd, J=9.0, 5.8, 2H), 7.26 (d, J=5.5, 1H), 7.08 (dd, J=8.6, 8.6, 2H), 4.76-4.82 (m, 1H), 3.99 (s, 3H), 2.92-2.99 (m, 1H), 2.84 (s, 3H), 2.73-2.81 (m, 1H), 2.58-2.67 (m, 1H), 2.06-2.15 (m, 1H).

Examples 26-52

Examples 26 to 52 were prepared by the following protocol

Method

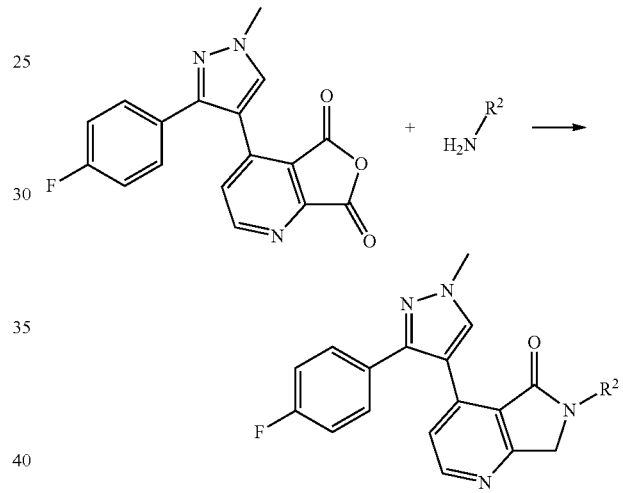

A solution of 4-[3-(4-fluoro-phenyl)-1-methyl-1H-pyrazol-4-yl]-furo[3,4-b]pyridine-5,7-dione (0.1 mmol) in acetic acid (0.1 mL) was added to a vial containing the appropriate amine (0.1 mmol). The vial was heated to 120° C. for 10 min, at which time zinc powder was added and the vial was heated to 110° C. for 7 hr, then shaken at rt for 16 hr. The reaction solution was filtered through an empty SPE cartridge to remove the zinc powder, washed with EtOAc, and concentrated down. The residue was dissolved in DMSO (1 mL) and purified by reversed-phase HPLC (Column: Waters Atlantis $C_{18}$ 4.6×50 mm, 5 μm; Mobile phase A: 0.05% TFA in water (v/v); Mobile phase B: 0.05% TFA in acetonitrile (v/v); Gradient: 5% to 95% B).

$R^2$ in Table 2 below is based on:

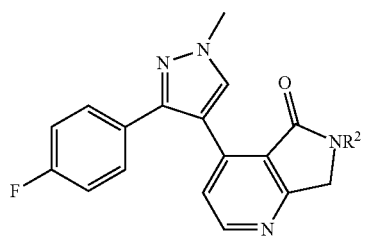

TABLE 2

| Ex# | R² | IUPAC NAME | Ret. Time (min) [HPLC in footnotes] | Calc'd Exact Mol. Wt. | Mass spec, Observed ion m/z (M + 1) or (M + 2)/2 |
|---|---|---|---|---|---|
| 26 | 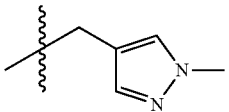 [SMILES: *Cc1cnn(C)c1] | 4-[3-(4-fluorophenyl)-1-methyl-1H-pyrazol-4-yl]-6-[(1-methyl-1H-pyrazol-4-yl)methyl]-6,7-dihydro-5H-pyrrolo[3,4-b]pyridin-5-one | 2.32 | 402.1604 | 403.1109 |
| 27 | 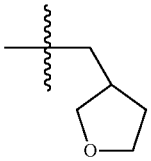 [SMILES: *CC1CCOC1] | 4-[3-(4-fluorophenyl)-1-methyl-1H-pyrazol-4-yl]-6-(tetrahydrofuran-3-ylmethyl)-6,7-dihydro-5H-pyrrolo[3,4-b]pyridin-5-one | 2.34 | 392.1649 | 393.1183 |
| 28 | 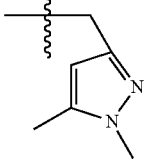 | 6-[(1,5-dimethyl-1H-pyrazol-3-yl)methyl]-4-[3-(4-fluorophenyl)-1-methyl-1H-pyrazol-4-yl]-6,7-dihydro-5H-pyrrolo[3,4-b]pyridin-5-one | 2.48 | 416.1761 | 417.1566 |
| 29 | —(CH₂)₃—O—CH₃ | 4-[3-(4-fluorophenyl)-1-methyl-1H-pyrazol-4-yl]-6-(3-methoxypropyl)-6,7-dihydro-5H-pyrrolo[3,4-b]pyridin-5-one | 2.4 | 380.1649 | 381.148 |
| 30 | —(CH₂)₂—O-t-Butyl | 6-(2-tert-butoxyethyl)-4-[3-(4-fluorophenyl)-1-methyl-1H-pyrazol-4-yl]-6,7-dihydro-5H-pyrrolo[3,4-b]pyridin-5-one | 2.81 | 408.1962 | 409.1731 |
| 31 | 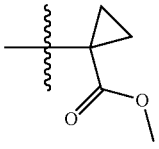 [SMILES: *C1(C(=O)OC)CC1] | methyl 1-{4-[3-(4-fluoro-phenyl)-1-methyl-1H-pyrazol-4-yl]-5-oxo-5,7-dihydro-6H-pyrrolo[3,4-b]pyridin-6-yl}cyclopropanecarboxylate | 2.51 | 406.1441 | 407.1035 |
| 32 | 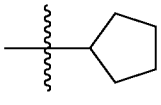 | 6-cyclopentyl-4-[3-(4-fluorophenyl)-1-methyl-1H-pyrazol-4-yl]-6,7-dihydro-5H-pyrrolo[3,4-b]pyridin-5-one | 2.85 | 376.17 | 377.1632 |
| 33 | 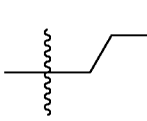 | 4-[3-(4-fluorophenyl)-1-methyl-1H-pyrazol-4-yl]-6-[2-(1-methyl-1H-pyrazol-4-yl)ethyl]-6,7-dihydro-5H-pyrrolo[3,4-b]pyridin-5-one | 2.35 | 416.1761 | 417.1064 |
| 34 | —CH₂CH₃ | 6-ethyl-4-[3-(4-fluorophenyl)-1-methyl-1H-pyrazol-4-yl]-6,7-dihydro-5H-pyrrolo[3,4-b]pyridin-5-one | 2.41 | 336.1386 | 337.1468 |
| 35 | 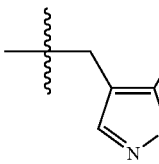 | 6-[(1,5-dimethyl-1H-pyrazol-4-yl)methyl]-4-[3-(4-fluorophenyl)-1-methyl-1H-pyrazol-4-yl]-6,7-dihydro-5H-pyrrolo[3,4-b]pyridin-5-one | 2.34 | 416.1761 | 417.1088 |

TABLE 2-continued

| Ex# | R² | IUPAC NAME | Ret. Time (min) [HPLC in footnotes] | Calc'd Exact Mol. Wt. | Mass spec, Observed ion m/z (M + 1) or (M + 2)/2 |
|---|---|---|---|---|---|
| 36 | (tetrahydro-2H-pyran-4-yl) | 4-[3-(4-fluorophenyl)-1-methyl-1H-pyrazol-4-yl]-6-(tetrahydro-2H-pyran-4-yl)-6,7-dihydro-5H-pyrrolo[3,4-b]pyridin-5-one | 2.37 | 392.1649 | 393.1505 |
| 37 | —CH₂-cyclopropyl | 6-(cyclopropylmethyl)-4-[3-(4-fluorophenyl)-1-methyl-1H-pyrazol-4-yl]-6,7-dihydro-5H-pyrrolo[3,4-b]pyridin-5-one | 2.67 | 362.1543 | 363.1586 |
| 38 | (3-methyl-1,2,4-oxadiazol-5-yl)ethyl | 4-[3-(4-fluorophenyl)-1-methyl-1H-pyrazol-4-yl]-6-[2-(3-methyl-1,2,4-oxadiazol-5-yl)ethyl]-6,7-dihydro-5H-pyrrolo[3,4-b]pyridin-5-one | 2.44 | 418.1554 | 419.107 |
| 39 | —CH₂-i-propyl | 4-[3-(4-fluorophenyl)-1-methyl-1H-pyrazol-4-yl]-6-isobutyl-6,7-dihydro-5H-pyrrolo[3,4-b]pyridin-5-one | 2.75 | 364.17 | 365.1593 |
| 40 | —CH₂CH₂CN | 3-{4-[3-(4-fluorophenyl)-1-methyl-1H-pyrazol-4-yl]-5-oxo-5,7-dihydro-6H-pyrrolo[3,4-b]pyridin-6-yl}propanenitrile | 2.32 | 361.1339 | 362.1238 |
| 41 | (3-cyanobenzyl) | 3-({4-[3-(4-fluorophenyl)-1-methyl-1H-pyrazol-4-yl]-5-oxo-5,7-dihydro-6H-pyrrolo[3,4-b]pyridin-6-yl}methyl)benzonitrile | 2.82 | 423.1495 | 424.0765 |
| 42 | —(CH₂)₂—O—CH₃ | 4-[3-(4-fluorophenyl)-1-methyl-1H-pyrazol-4-yl]-6-(2-methoxyethyl)-6,7-dihydro-5H-pyrrolo[3,4-b]pyridin-5-one | 2.35 | 366.1492 | 367.1418 |
| 43 | —CH₂—C(O)—N(CH₃)₂ | 2-{4-[3-(4-fluorophenyl)-1-methyl-1H-pyrazol-4-yl]-5-oxo-5,7-dihydro-6H-pyrrolo[3,4-b]pyridin-6-yl}-N,N-dimethylacetamide | 2.18 | 393.1601 | 394.1341 |
| 44 | (1R,2S)-2-(methoxymethyl)cyclopentyl | 4-[3-(4-fluorophenyl)-1-methyl-1H-pyrazol-4-yl]-6-[(1R,2S)-2-(methoxymethyl)cyclopentyl]-6,7-dihydro-5H-pyrrolo[3,4-b]pyridin-5-one | 2.75 | 420.1962 | 421.1434 |
| 45 | (1R,5S,6r)-3-oxabicyclo[3.1.0]hex-6-yl | 4-[3-(4-fluorophenyl)-1-methyl-1H-pyrazol-4-yl]-6-[(1R,5S,6r)-3-oxabicyclo[3.1.0]hex-6-yl]-6,7-dihydro-5H-pyrrolo[3,4-b]pyridin-5-one | 2.37 | 390.1492 | 391.1226 |

TABLE 2-continued

| Ex# | R² | IUPAC NAME | Ret. Time (min) [HPLC in footnotes] | Calc'd Exact Mol. Wt. | Mass spec, Observed ion m/z (M + 1) or (M + 2)/2 |
|---|---|---|---|---|---|
| 46 | (2-oxotetrahydrofuran-3-yl) | 4-[3-(4-fluorophenyl)-1-methyl-1H-pyrazol-4-yl]-6-[(3S)-2-oxotetrahydrofuran-3-yl]-6,7-dihydro-5H-pyrrolo[3,4-b]pyridin-5-one | 2.34 | 392.1285 | 393.0993 |
| 47 | (1R)-1-methylbutyl | 4-[3-(4-fluorophenyl)-1-methyl-1H-pyrazol-4-yl]-6-[(1R)-1-methylbutyl]-6,7-dihydro-5H-pyrrolo[3,4-b]pyridin-5-one | 2.94 | 378.1856 | 379.1638 |
| 48 | bicyclo[1.1.1]pent-1-yl | 6-bicyclo[1.1.1]pent-1-yl-4-[3-(4-fluorophenyl)-1-methyl-1H-pyrazol-4-yl]-6,7-dihydro-5H-pyrrolo[3,4-b]pyridin-5-one | 2.88 | 374.1543 | 375.1468 |
| 49 | —CH₂—C(O)O-i-propyl | isopropyl {4-[3-(4-fluorophenyl)-1-methyl-1H-pyrazol-4-yl]-5-oxo-5,7-dihydro-6H-pyrrolo[3,4-b]pyridin-6-yl}acetate | 2.67 | 408.1598 | 409.1731 |
| 50 | pyridin-3-ylmethyl | 4-[3-(4-fluorophenyl)-1-methyl-1H-pyrazol-4-yl]-6-(pyridin-3-ylmethyl)-6,7-dihydro-5H-pyrrolo[3,4-b]pyridin-5-one | 1.94 | 399.1495 | 400.1359 |
| 51 | —(CH₂)₃—O—Et | 6-(3-ethoxypropyl)-4-[3-(4-fluorophenyl)-1-methyl-1H-pyrazol-4-yl]-6,7-dihydro-5H-pyrrolo[3,4-b]pyridin-5-one | 3.73 | 394.1805 | 395.1689 |
| 52 | (6-methylpyridin-3-yl)methyl | 4-[3-(4-fluorophenyl)-1-methyl-1H-pyrazol-4-yl]-6-[(6-methylpyridin-3-yl)methyl]-6,7-dihydro-5H-pyrrolo[3,4-b]pyridin-5-one | 1.97 | 413.1652 | 414.1193 |

Kinase Assay.

The CK1δ kinase assay was performed in a 40 μl final volume in buffer containing 50 mM Tris, pH 7.5, 10 mM MgCl₂, 1 mM dithiothreitol, 100 μg/mL BSA with 10 μM ATP, 2 nM CK1δ wild type, and 42 μM peptide substrate PLSRTLpSVASLPGL (Flotow et al., 1990) in the presence of 1 μl of CK1δ inhibitor or 4% DMSO. The reaction was incubated for 85 min at 25° C.; detection was carried out as described for the Kinase-Glo Assay (Promega). Luminescent output was measured on the Perkin Elmer Envision plate reader (PerkinElmer, Waltham, Mass.).

The CK1ε kinase assay was performed in a 40-μl final volume in buffer containing 50 mM Tris, pH 7.5, 10 mM MgCl₂, 1 mM dithiothreitol, 100 μg/mL BSA with 10 μM ATP, 2.5 nM CKI ε wild type, and 42 μM peptide substrate PLSRTLpSVASLPGL (Flotow et al., 1990) in the presence of 1 μl of CKI ε inhibitor or 4% DMSO. The reaction was incubated for 70 min at 25° C.; detection was carried out as described for the Kinase-Glo Assay (Promega). Luminescent output was measured on the Perkin Elmer Envision plate reader (PerkinElmer, Waltham, Mass.).

CK1 WCA HCS Nuclear Translocation Assay.

Cos 7 cells were maintained at 37° C. in 5% CO₂ in Dulbecco's Modified Eagle Medium (Gibco 11995) supplemented with 10% fetal bovine serum. Log-phase cells were dislodged with 5 min treatment of TrypLE Express (Gibco 12605) and viable cell count was determined with Cedex cell counter. Cells were diluted in DMEM medium to a density of 1.5e5 viable cells/mL in ⅔ of the final volume of final transfected cell mix. Cells were cotransfected with two plasmid DNAs, mouse Per3-GFP (green fluorescent protein) in pd2EGFP-N1 vector and human CKI in pcDNA4/hisA vector (for CK1Epsilon at a ratio of 1:5 respectively; for CK1δ at a ratio of 1:11 respectively), using Lipofectamine 2000 reagent (Invitrogen) according to the manufacturer's recommendations. The transfection mix contained approximately 0.83 µg/mL of DNA and 6 µL/mL of Lipofectamine 2000, in a total of ⅓ of the final transfection volume in Opti-MEM I medium (Invitrogen). After 20 min at rt, the cell mix was combined with the DNA transfection mix, per manufacturer instructions. 50 µL of the transfected cell suspension was dispensed per well by multidrop dispenser into Greiner 384-well Cellcoat (PDL) plates (Greiner #781946).

Compounds were solubilized in 100% DMSO, diluted with Opti-MEM I to a 4× concentration before addition to plated cells. After overnight exposure at 37° C. in a $CO_2$ incubator, cells were fixed by the addition of 12% paraformaldehyde (Electron Microscopy Sciences, Hatfield, Pa.) in phosphate-buffered saline (PBS) with 20% sucrose to a final concentration of 4%, and then the cells were incubated for 30 min at rt. Fixative was removed, and cells were washed with PBS and then stained with 0.4 µg/ml Hoechst dye (Invitrogen) in blocking buffer containing 4% goat serum (Vector Labs s-1000) and 0.1% TritonX (Sigma T8787) for 1 h. Cells were washed again with PBS and stored at 4° C. in PBS or scanned immediately with the Cellomics ArrayScan VTI. CKIδ dependent nuclear localization of the GFP-tagged mPer3 protein was quantitated using the Cellomics ArrayScan VTI system utilizing the Cytoplasm to Nucleus translocation bioapplication to calculate the Nuclear-Cytoplasmic Intensity difference. Inhibitors of CK1 δ/ε were tested across a dose response curve to evaluate their ability to inhibit mPer3-GFP translocation to the nucleus. Cells with a total intensity of mPER3:GFP expression equal to or greater than 20,000 are included in analysis.

Table 3 provides biological data for Examples 1 to 52.

TABLE 3

| Example | CK1 δ IC50 (nM) | CK1 ε:IC50 (nM) | CK1 δ WCA EC50 (nM) | CK1 ε WCA EC50 (nM) |
|---|---|---|---|---|
| 1 | 7.91 | 26.9 | 59.8 | 355 |
| 2 | 7.9 | 35.5 | 52.6 | 313 |
| 3 |  |  | 78.2 | 343 |
| 4 | 13.9 | 72.7 | 122 | 684 |
| 5 | 6.05 | 39 | 16.4 |  |
| 6 | 61 | 292 | 204 |  |
| 7 | 6.01 | 27.6 | 39.2 | 291 |
| 8 |  |  | 47 | 217 |
| 9 |  |  | 199 | 834 |
| 10 | 3.11 | 10.8 | 13.5 | 62.4 |
| 11 |  |  | 103 | 668 |
| 12 |  |  | 202 | 882 |
| 13 |  |  | 16.2 | 124 |
| 14 |  |  | 40.2 | 150 |
| 15 |  |  | 12.6 | 75.4 |
| 16 |  |  | 38.1 | 218 |
| 17 |  |  | 47.5 | 210 |
| 18 |  |  | 39.5 | 195 |
| 19 |  |  | 54.8 | 566 |
| 20 |  |  | 84.7 | 361 |
| 21 |  |  | 18.3 | 82.3 |
| 22 |  |  | 51.6 | 275 |
| 23 | 25.4 | 157 | 214 |  |
| 24 | 28.5 | 149 | 266 |  |
| 25 | 17.4 | 83.7 | 59.8 |  |
| 26 | 22.6 | 123 | 125 |  |
| 27 | 35.3 | 210 | 369 |  |
| 28 | 15.7 | 86.4 | 66.4 |  |
| 29 | 26.2 | 131 | 217 |  |
| 30 | 27.7 | 149 | 159 |  |
| 31 | 48.1 | 187 | 304 |  |
| 32 | 8.93 | 40.8 | 84.9 |  |
| 33 | >75.5 | >230 | 232 |  |
| 34 | 12.4 | 61.5 | 99 | 468 |
| 35 | 23.3 | 130 | 104 |  |
| 36 | >195 | >516 | 224 |  |
| 37 | 12.9 | 82.5 | 74.1 |  |
| 38 | 18.6 | 92 | 71.4 |  |
| 39 | 49.5 | 241 | 188 |  |
| 40 | 11.1 | 47.1 | 53.7 |  |
| 41 | 20.5 | 108 | 65.5 |  |
| 42 | 67.3 | 386 | 623 |  |
| 43 | 93.2 | 512 | 564 |  |
| 44 | 70.8 | 342 | 437 |  |
| 45 | 19.5 | 87 | 167 |  |
| 46 | 68.7 | 384 | 1430 |  |
| 47 | >160 | >423 | 89.7 |  |
| 48 | 18.4 | 80.7 | 130 |  |
| 49 | 108 | 496 | 506 |  |
| 50 | 21.3 | 145 | 83.6 |  |
| 51 | 14.6 | 63.8 | 129 |  |
| 52 | 19 | 127 | 60.7 |  |

We claim:

1. A compound of Formula I:

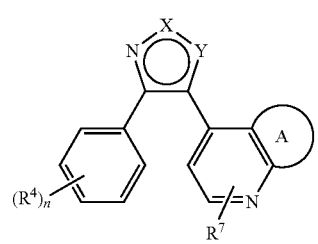

wherein X and Y are independently =N—, —NR$^1$—, CR$^1$, or —S—, provided that at least one of X and Y is CR$^1$;

Ring A is a 4- to 7-membered cycloalkyl or heterocloalkyl or a 5- to 6-membered heteroaryl, wherein up to 2 carbon atoms are replaced with a heteroatom selected from =N—, —NR$^2$—, —O—, —S and any remaining carbon atom may be substituted with R$^3$ as valency allows;

Each R$^1$ is independently H, $C_{1-4}$alkyl, $C_{3-6}$cycloalkyl, —CF$_3$, —(CH$_2$)$_{1-3}$CF$_3$, 4- to 10-membered heterocycloalkyl, wherein said heterocycloalkyl may be substituted with up to two substituents independently selected from halogen, OH, oxo, cyano, $C_{1-6}$alkyl, or $C_{1-6}$alkyl-O—$C_{1-6}$alkyl;

Each R$^2$ is independently H, $C_{1-6}$alkyl, $C_{4-10}$-bicycloalkyl, —(CH$_2$)$_t$—CN, —SO$_2$C$_{1-6}$alkyl, —SO$_2$(CH$_2$)$_t$C$_{3-6}$cycloalkyl, —C$_{1-6}$alkyl-O—C$_{1-6}$alkyl, —C$_{1-6}$alkyl-C(O)O—C$_{1-6}$alkyl, —C$_{3-6}$cycloalkyl-C(O)O—C$_{1-6}$alkyl, —C(O)—(O)$_u$—C$_{1-6}$alkyl, —C(O)—C$_{1-6}$alkyl-O—C$_{1-6}$alkyl, —C(O)—(O)$_u$—(CH$_2$)$_t$—(C$_{6-10}$aryl), —(CH$_2$)$_t$—(C$_{6-10}$aryl), —C(O)—(O)$_u$—(CH$_2$)$_t$-(5- to 10-membered heteroaryl), —(CH$_2$)$_t$—C(O)—NR$^5$R$^6$, —(CH$_2$)$_t$-(5- to 10-membered heteroaryl), —C(O)—(O)$_u$—(CH$_2$)$_t$-(3- to 10-membered heterocycloalkyl), —(CH$_2$)$_t$-(4- to 10-membered heterocycloalkyl), —C(O)—(O)$_u$—(CH$_2$)$_t$-(3- to 10-membered cycloalkyl), or —(CH$_2$)$_t$-(3- to 10-membered cycloalkyl), wherein said aryl, heteroaryl, cycloalkyl, and heterocycloalkyl of $R^2$ may be substituted with up to two substituents independently selected from halogen, OH, cyano, $C_{1-6}$alkyl, or $C_{1-6}$alkyl-O—$C_{1-6}$alkyl, and wherein any alkyl, cycloalkyl, and heterocycloalkyl of $R^2$ may be further substituted with oxo where valency allows;

Each $R^3$ is independently absent, $C_{1-3}$alkyl, halogen, oxo, —$NR^5R^6$, or —$OR^5$;

Each $R^4$ is independently halogen, —$CF_3$, $C_{1-3}$alkyl, —$(CH_2)_t$—$C_{3-4}$cycloalkyl, —$(CH_2)_t$—O—$C_{1-3}$alkyl, —$(CH_2)_t$-cyano, or —$(CH_2)_t$-hydroxy;

Each $R^5$ is independently H or $C_{1-6}$alkyl;
Each $R^6$ is independently H or $C_{1-6}$alkyl;
$R^7$ is H, halogen, or $C_{1-3}$alkyl;
n is 0, 1, or 2;
Each t is independently 0, 1 or 2; and
Each u is independently 0 or 1;
or a pharmaceutically acceptable salt thereof.

2. The compound of claim 1, or a pharmaceutically acceptable salt thereof, wherein each $R^1$ is independently H or $C_{1-4}$alkyl;

Each $R^2$ is independently H, $C_{1-6}$alkyl, —$SO_2C_{1-6}$alkyl, —$SO_2(CH_2)_t C_{3-6}$cycloalkyl, —$C_{1-6}$alkyl-O—$C_{1-6}$alkyl, —C(O)—(O)$_u$—$C_{1-6}$alkyl, —$(CH_2)_t$—$(C_{6-10}$aryl), —C(O)—(O)$_u$—$(CH_2)_t$-(5- to 10-membered heteroaryl), —$(CH_2)_t$—C(O)—$NR^5R^6$, —$(CH_2)_t$-(5- to 10-membered heteroaryl), —$(CH_2)_t$-(4- to 10-membered heterocycloalkyl), or —$(CH_2)_t$-(3- to 10-membered cycloalkyl), wherein said aryl, heteroaryl, cycloalkyl, and heterocycloalkyl of $R^2$ may be substituted with up to two substituents independently selected from halogen, OH, cyano, —$C_{1-6}$alkyl, —C(O)—O—$C_{1-3}$alkyl, or $C_{1-6}$alkyl-O—$C_{1-6}$alkyl, and wherein any alkyl, cycloalkyl, and heterocycloalkyl of $R^2$ may be further substituted with oxo where valency allows;

Each $R^3$ is independently absent, $C_{1-3}$alkyl, oxo, —$NR^5R^6$, or —$OR^5$;
$R^4$ is halogen;
Each $R^5$ is H;
Each $R^6$ is independently H or $C_{1-6}$alkyl;
$R^7$ is H;
n is 1;
Each t is independently 0, 1 or 2; and
Each u is independently 0 or 1.

3. The compound of claim 1, or a pharmaceutically acceptable salt thereof, wherein A is any one of the following:

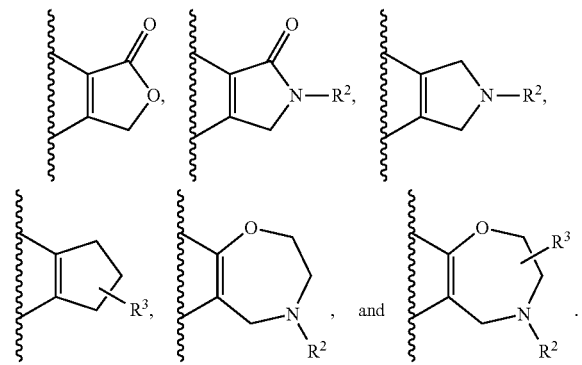

4. The compound of claim 3, or a pharmaceutically acceptable salt thereof, wherein $R_2$ is independently H, —$CH_3$, or $SO_2CH_3$; and $R^3$ is independently absent or oxo.

5. The compound of claim 1, or a pharmaceutically acceptable salt thereof, wherein X is $NR^1$ and said $R^1$ off of N is $C_{1-4}$ alkyl or $C_{3-4}$cycloalkyl;
Y is $CR^1$ and said $R^1$ off of C is H or $CH_3$;
$R^4$ is F;
A is

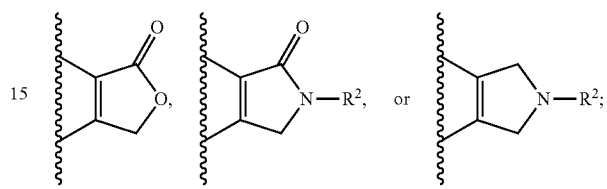

and $R^7$ is H.

6. The compound of claim 1, or a pharmaceutically acceptable salt thereof, wherein the compound is selected from:
4-(3-(4-fluorophenyl)-1-methyl-1H-pyrazol-4-yl)furo[3,4-b]pyridin-5(7H)-one;
4-[3-(4-fluorophenyl)-1-methyl-1H-pyrazol-4-yl]-6-methyl-6,7-dihydro-5H-pyrrolo[3,4-b]pyridin-5-one;
4-[3-(4-fluorophenyl)-1-methyl-1H-pyrazol-4-yl]-6,7-dihydro-5H-pyrrolo[3,4-b]pyridin-5-one;
6-benzyl-4-[3-(4-fluorophenyl)-1-methyl-1H-pyrazol-4-yl]-6,7-dihydro-5H-pyrrolo[3,4-b]pyridin-5-one;
9-[3-(4-fluorophenyl)-1-methyl-1H-pyrazol-4-yl]-2,3,4,5-tetrahydropyrido[2,3-f][1,4]oxazepine;
9-[3-(4-fluorophenyl)-1-methyl-1H-pyrazol-4-yl]-2-methyl-2,3,4,5-tetrahydropyrido[2,3-f][1,4]oxazepine;
9-[3-(4-fluorophenyl)-1-methyl-1H-pyrazol-4-yl]-3-methyl-2,3,4,5-tetrahydropyrido[2,3-f][1,4]oxazepine;
4-[3-(4-fluorophenyl)-1-methyl-1H-pyrazol-4-yl]-6-(methylsulfonyl)-6,7-dihydro-5H-pyrrolo[3,4-b]pyridine;
6-(ethylsulfonyl)-4-[3-(4-fluorophenyl)-1-methyl-1H-pyrazol-4-yl]-6,7-dihydro-5H-pyrrolo[3,4-b]pyridine;
4-[3-(4-fluorophenyl)-1-methyl-1H-pyrazol-4-yl]-6-propionyl-6,7-dihydro-5H-pyrrolo[3,4-b]pyridine;
4-[3-(4-fluorophenyl)-1-methyl-1H-pyrazol-4-yl]-N-methyl-6,7-dihydro-5H-cyclopenta[b]pyridin-7-amine;
4-[3-(4-fluorophenyl)-1-methyl-1H-pyrazol-4-yl]-6-[(1-methyl-1H-pyrazol-4-yl)methyl]-6,7-dihydro-5H-pyrrolo[3,4-b]pyridin-5-one;
4-[3-(4-fluorophenyl)-1-methyl-1H-pyrazol-4-yl]-6-(tetrahydrofuran-3-ylmethyl)-6,7-dihydro-5H-pyrrolo[3,4-b]pyridin-5-one;
6-[(1,5-dimethyl-1H-pyrazol-3-yl)methyl]-4-[3-(4-fluorophenyl)-1-methyl-1H-pyrazol-4-yl]-6,7-dihydro-5H-pyrrolo[3,4-b]pyridin-5-one;
6-cyclopentyl-4-[3-(4-fluorophenyl)-1-methyl-1H-pyrazol-4-yl]-6,7-dihydro-5H-pyrrolo[3,4-b]pyridin-5-one;
6-ethyl-4-[3-(4-fluorophenyl)-1-methyl-1H-pyrazol-4-yl]-6,7-dihydro-5H-pyrrolo[3,4-b]pyridin-5-one;
6-[(1,5-dimethyl-1H-pyrazol-4-yl)methyl]-4-[3-(4-fluorophenyl)-1-methyl-1H-pyrazol-4-yl]-6,7-dihydro-5H-pyrrolo[3,4-b]pyridin-5-one;
6-(cyclopropylmethyl)-4-[3-(4-fluorophenyl)-1-methyl-1H-pyrazol-4-yl]-6,7-dihydro-5H-pyrrolo[3,4-b]pyridin-5-one;
4-[3-(4-fluorophenyl)-1-methyl-1H-pyrazol-4-yl]-6-[2-(3-methyl-1,2,4-oxadiazol-5-yl)ethyl]-6,7-dihydro-5H-pyrrolo[3,4-b]pyridin-5-one;

3-{4-[3-(4-fluorophenyl)-1-methyl-1H-pyrazol-4-yl]-5-oxo-5,7-dihydro-6H-pyrrolo[3,4-b]pyridin-6-yl}propanenitrile;

3-({4-[3-(4-fluorophenyl)-1-methyl-1H-pyrazol-4-yl]-5-oxo-5,7-dihydro-6H-pyrrolo[3,4-b]pyridin-6-yl}methyl)benzonitrile;

4-[3-(4-fluorophenyl)-1-methyl-1H-pyrazol-4-yl]-6-[(1R,5S,6r)-3-oxabicyclo[3.1.0]hex-6-yl]-6,7-dihydro-5H-pyrrolo[3,4-b]pyridin-5-one;

6-bicyclo[1.1.1]pent-1-yl-4-[3-(4-fluorophenyl)-1-methyl-1H-pyrazol-4-yl]-6,7-dihydro-5H-pyrrolo[3,4-b]pyridin-5-one;

4-[3-(4-fluorophenyl)-1-methyl-1H-pyrazol-4-yl]-6-(pyridin-3-ylmethyl)-6,7-dihydro-5H-pyrrolo[3,4-b]pyridin-5-one;

6-(3-ethoxypropyl)-4-[3-(4-fluorophenyl)-1-methyl-1H-pyrazol-4-yl]-6,7-dihydro-5H-pyrrolo[3,4-b]pyridin-5-one; and 4-[3-(4-fluorophenyl)-1-methyl-1H-pyrazol-4-yl]-6-[(6-methylpyridin-3-yl)methyl]-6,7-dihydro-5H-pyrrolo[3,4-b]pyridin-5-one.

7. A compound that is 4-(3-(4-fluorophenyl)-1-methyl-1H-pyrazol-4-yl)furo[3,4-b]pyridin-5(7H)-one or a pharmaceutically acceptable salt thereof.

8. A pharmaceutical composition comprising a compound of claim 1 or a pharmaceutically acceptable salt thereof, and a pharmaceutically acceptable carrier.

9. A pharmaceutical composition comprising a compound of claim 6 or a pharmaceutically acceptable salt thereof, and a pharmaceutically acceptable carrier.

10. A pharmaceutical composition comprising a compound of claim 7 or a pharmaceutically acceptable salt thereof, and a pharmaceutically acceptable carrier.

* * * * *